(12) United States Patent
Patolsky et al.

(10) Patent No.: US 11,275,078 B2
(45) Date of Patent: Mar. 15, 2022

(54) METHOD AND SYSTEM FOR SENSING

(71) Applicant: Ramot at Tel-Aviv University Ltd., Tel-Aviv (IL)

(72) Inventors: Fernando Patolsky, Rehovot (IL); Vadim Krivitsky, Bney-Ayish (IL); Marina Zverzhinetsky, Rishon-LeZion (IL)

(73) Assignee: Ramot at Tel-Aviv University Ltd., Tel-Aviv (IL)

(*) Notice: Subject to any disclaimer, the term of this patent is extended or adjusted under 35 U.S.C. 154(b) by 777 days.

(21) Appl. No.: 16/060,038

(22) PCT Filed: Dec. 8, 2016

(86) PCT No.: PCT/IL2016/051320
§ 371 (c)(1),
(2) Date: Jun. 7, 2018

(87) PCT Pub. No.: WO2017/098518
PCT Pub. Date: Jun. 15, 2017

(65) Prior Publication Data
US 2019/0200923 A1 Jul. 4, 2019

Related U.S. Application Data

(60) Provisional application No. 62/264,913, filed on Dec. 9, 2015, provisional application No. 62/264,944, filed on Dec. 9, 2015.

(51) Int. Cl.
*A61B 5/1473* (2006.01)
*G01N 33/50* (2006.01)
(Continued)

(52) U.S. Cl.
CPC ........ *G01N 33/5005* (2013.01); *A61B 5/1473* (2013.01); *A61B 5/4866* (2013.01);
(Continued)

(58) Field of Classification Search
CPC ........ A61B 5/00; A61B 5/1473; A61B 5/4866; A61B 5/6847; A61B 5/6833;
(Continued)

(56) References Cited

U.S. PATENT DOCUMENTS

| 3,935,071 A | 1/1976 | Bergmeyer et al. |
| 7,619,290 B2 | 11/2009 | Lieber et al. |

(Continued)

FOREIGN PATENT DOCUMENTS

| CN | 103323516 | 9/2013 |
| EP | 1669748 | 6/2006 |

(Continued)

OTHER PUBLICATIONS

Krivitsky, et al. "A Chemically-Sensitive Nanowire Sensor Array for Sensing of H2O2 and pH in Physiological Solutions." Proceedings from the 17th International Conference on Miniaturized Systems for Chemistry and Life Sciences, Freiburg, Germany, Oct. 27-31, 2013; pp. 805-807 (Year: 2013).*

(Continued)

*Primary Examiner* — Eric J Messersmith

(57) ABSTRACT

A sensing element comprises a transistor having a gate electrode, a source electrode, a gate electrode and a semiconductor nanostructure connecting between the source and the gate electrodes. The semiconductor nanostructure is modified by a functional moiety covalently attached thereto. A voltage source is connected to the gate electrode. A controller controls a gate voltage applied by the voltage source to the gate electrode such as to reverse a redox reaction occurring when the moiety contacts a redox reactive agent.

20 Claims, 32 Drawing Sheets

(51) Int. Cl.
*G01N 27/414* (2006.01)
*H01L 23/532* (2006.01)
*H01L 29/06* (2006.01)
*A61B 5/00* (2006.01)
*H01L 29/16* (2006.01)
*B82Y 15/00* (2011.01)
*H01L 51/00* (2006.01)
*H01L 51/05* (2006.01)

(52) U.S. Cl.
CPC .......... *A61B 5/6833* (2013.01); *A61B 5/6847* (2013.01); *G01N 27/4145* (2013.01); *G01N 27/4146* (2013.01); *H01L 23/532* (2013.01); *H01L 29/06* (2013.01); *H01L 29/0673* (2013.01); *H01L 29/16* (2013.01); *B82Y 15/00* (2013.01); *H01L 51/0049* (2013.01); *H01L 51/0545* (2013.01); *H01L 51/0558* (2013.01)

(58) Field of Classification Search
CPC ............. G01N 27/414; G01N 33/5005; G01N 27/4146; G01N 27/4145; H01L 29/06; H01L 29/16; H01L 29/0673; H01L 23/532; H01L 51/0558; H01L 51/0049; H01L 51/0545; B82Y 15/00
See application file for complete search history.

(56) References Cited

U.S. PATENT DOCUMENTS

| | | | |
|---|---|---|---|
| 7,632,234 | B2 | 12/2009 | Manda et al. |
| 8,232,584 | B2* | 7/2012 | Lieber .................... A61B 5/418 257/253 |
| 10,274,456 | B2 | 4/2019 | Patolsky et al. |
| 2007/0227906 | A1* | 10/2007 | Boussaad ........... G01N 33/5438 205/777.5 |
| 2007/0264634 | A1* | 11/2007 | Bock ..................... C12Q 1/001 435/6.11 |
| 2009/0124025 | A1 | 5/2009 | Hamilton et al. |
| 2010/0022012 | A1 | 1/2010 | Lieber et al. |
| 2010/0093019 | A1 | 4/2010 | Ditcham et al. |
| 2010/0140110 | A1 | 6/2010 | Kim et al. |
| 2010/0256344 | A1 | 10/2010 | Thompson et al. |
| 2010/0325073 | A1 | 12/2010 | Haick |
| 2011/0233059 | A1 | 9/2011 | Grundig et al. |
| 2016/0258899 | A1 | 9/2016 | Patolsky et al. |
| 2016/0290957 | A1* | 10/2016 | Ram ..................... C12Q 1/6825 |
| 2017/0181669 | A1* | 6/2017 | Lin ........................ A61B 5/145 |
| 2018/0088079 | A1* | 3/2018 | Lieber ............... G01N 27/4146 |
| 2018/0372678 | A1 | 12/2018 | Patolsky et al. |
| 2019/0234900 | A1 | 8/2019 | Patolsky et al. |
| 2020/0088678 | A1* | 3/2020 | Yang ..................... C12Q 1/006 |

FOREIGN PATENT DOCUMENTS

| | | |
|---|---|---|
| EP | 1806414 | 7/2007 |
| GB | 2294808 | 5/1996 |
| JP | 2005-077210 | 3/2005 |
| JP | 2009-540798 | 11/2009 |
| JP | 2010-515887 | 5/2010 |
| JP | 2012-511156 | 5/2012 |
| WO | WO 2004/034025 | 4/2004 |
| WO | WO 2005/004204 | 1/2005 |
| WO | WO 2008/027078 | 3/2008 |
| WO | WO 2008/030395 | 3/2008 |
| WO | WO 2008/083446 | 7/2008 |
| WO | WO 2009/104180 | 8/2009 |
| WO | WO 2010/115143 | 10/2010 |
| WO | WO 2011/000443 | 1/2011 |
| WO | WO 2012/082494 | 6/2012 |
| WO | WO 2012/137207 | 10/2012 |
| WO | WO 2015/059704 | 4/2015 |
| WO | WO 2017/098517 | 6/2017 |
| WO | WO 2017/098518 | 6/2017 |

OTHER PUBLICATIONS

Supplementary European Search Report and the European Search Opinion dated Jul. 11, 2019 From the European Patent Office Re. Application No. 16872559.6. (10 Pages).
Supplementary European Search Report and the European Search Opinion dated Jul. 10, 2019 From the European Patent Office Re. Application No. 16872558.8. (12 Pages).
Elnathan et al. "Biorecognition Layer Engineering: Overcoming Screening Limitations of Nanowire-Based FET Devices", Nano Letters, XP055366864, 12(10): 5245-5254, Published Online Sep. 10, 2012.
Gao et al. "General Strategy for Biodetection in High Ionic Strength Solutions Using Transistor-Based Nanoelectronic Sensors", Nano Letters, XP055317106, 15(3): 2143-2148, Published Online Feb. 9, 2015.
Hwang et al. "Biodegradable Elastomers and Silicon Nanomembranes/Nanoribbons for Stretchable, Transient Electronics, and Biosensors", Nano Letters, XP055601726, 15(5): 2801-2808, Published Online Feb. 23, 2015.
Kim et al. "Direct Label-Free Electrical Immunodetection in Human Serum Using A Flow-Through-Apparatus Approach With Integrated Field-Effect Transistors", Biosensors and Bioelectronics, XP029490340, 25(7): 1767-1773, Available Online Dec. 29, 2009.
Rajan et al. "Performance Limitations for Nanowire/Nanoribbon Biosensors", Wiley Interdisciplinary Reviews: Nanomedicine and Nanobiotechnology, XP055593106, 5(6): 629-645, Published Online Jul. 29, 2013.
Ramachandran et al. "A Rapid, Multiplexed, High-Throughput Flow-Through Membrane Immunoassay: A Convenient Alternative to ELISA", Diagnostics, XP055549823, 3(2): 244-260, Published Online Apr. 2, 2013.
Requisition by the Examiner dated May 11, 2020 From the Innovation, Science and Economic Development Canada, Canadian Intellectual Property Office Re. Application No. 2,927,332. (7 Pages).
Tey et al. "Nanotubes-/Nanowires-Based, Microfluidic-Integrated Transistors for Detecting Biomolecules", Microfluidics and Nanofluidics, 9(6): 1185-1214, Dec. 2010.
Official Action dated Mar. 27, 2020 from the US Patent and Trademark Office Re. U.S. Appl. No. 16/297,665. (41 pages).
Notice of Reasons for Rejection dated Aug. 11, 2020 From the Japan Patent Office Re. Application No. 2018-530022. (3 Pages).
Official Action dated Jul. 5, 2019 From the US Patent and Trademark Office Re. U.S. Appl. No. 16/060,423. (19 pages).
Communication Pursuant to Article 94(3) EPC dated May 9, 2017 From the European Patent Office Re. Application No. 14796555.2. (6 Pages).
Communication Pursuant to Article 94(3) EPC dated Feb. 20, 2018 From the European Patent Office Re. Application No. 14796555.2. (6 Pages).
International Preliminary Report on Patentability dated May 6, 2016 From the International Bureau of WIPO Re. Application No. PCT/IL2014/050921.
International Search Report and the Written Opinion dated Feb. 23, 2015 From the International Searching Authority Re. Application No. PCT/IL2014/050921.
International Search Report and the Written Opinion dated Mar. 26, 2017 From the International Searching Authority Re. Application No. PCT/IL2016/051319. (12 Pages).
International Search Report and the Written Opinion dated Mar. 29, 2017 From the International Searching Authority Re. Application No. PCT/IL2016/051320. (12 Pages).
Notice of Eligibility for Grant and Examination Report dated Jun. 11, 2018 From the Intellectual Property Office of Singapore, IPOS Re. Application No. 11201602976X. (7 Pages).
Official Action dated Jul. 5, 2018 From the US Patent and Trademark Office Re. U.S. Appl. No. 15/030,886. (54 pages).
Search Report and Written Opinion dated Sep. 21, 2016 From the Intellectual Property Office of Singapore Re. Application No. 11201602976X.

(56) References Cited

OTHER PUBLICATIONS

Written Opinion dated Sep. 6, 2017 From the Intellectual Property Office of Singapore, IPOS Re. Application No. 11201602976X. (8 Pages).
Chen et al. "Label-Free Cytokine Micro- and Nano-Biosensing Towards Personalized Medicine of Systemic Inflammatory Disorders", Advanced Drug Delivery Reviews, 95: 90-103, Available Online Sep. 15, 2015. p. 4, r-h col., 1st Para, Fig.3.
Chen et al. "Silicon Nanowire Filed-Effect Transistor-Based Biosensors for Biomedical Diagnosis and Cellular Recording Investigation", Nano Today, 6(2): 131-154, Available Online Mar. 8, 2011.
Clavaguera et al. "Sup-PPM Detection of Nerve Agents Using Chemically Functionalized Silicon Nanoribbon Field-Effect Transistors", Angewandte Chemie International Edition, 49(24): 4063-4066, Jun. 2010.
Cui et al. "Nanowire Nanosensors for Highly Sensitive and Selective Detection of Biological and Chemical Species", Science, 293(5533): 1289-1292, Aug. 17, 2001.
De et al. "Integrated Label-Free Silicon Naonowire Sensor Arrays for (Bio)Chemical Analysis", The Analyst, XP055168035, 138(11): 3221-3229, Jan. 2013. Fig.2, figs.1-3, Abstract, p. 4, 2nd col.
Duan et al. "Intracellular Recordings of Action Potentials by An Extracellular Nanoscale Field-Effect Transistor", Nature Nanotechnology, 7(3): 174-179, Published Online Dec. 18, 2011.
Garcia et al. "Enhanced Determination of Glucose by Microchip Electrophoresis With Pulsed Amperometric Detection", Analytica Chimica Acta, 508(1): 1-9, Apr. 15, 2004.
Garcia-Perez et al. "Metabolic Fingerprinting With Capillary Electrophoresis", Journal of Chromatography A, 1204(2): 130-139, Available Online Jul. 12, 2008.
Griffin et al. "Metabolic Profiles of Cancer Cells", Nature Reviews Cancer, 4(7): 551-561, Jul. 2004.
Holcomb et al. "Electrode Array Detector for Microchip Capillary Electrophoresis", The Analyst, 134(3): 486-492, Published Online Dec. 3, 2008.
Hsiung et al. "Multiplex Reatl-Time Monitoring of Cellular Metabolic Activity Using A Redox-Reactive Nanowire Biosensor", 17th International Conference on Miniaturized Systems for Chemistry and Life Sciences, Freiburg, Germany, Oct. 27-31, 2013, XP055167304, p. 1959-1961, Oct. 2013.
Huang et al. "Real-Time and Label-Free Detection of the Prostate-Specific Antigen in Human Serum by A Polycrystalline Silicon Nanowire Field-Effect Transistor Biosensor", Analytical Chemistry, 85(16): 7912-7918, Jul. 11, 2013. p. 7914, r-h col., 1st Para, Figs.3b, 4b, 6.
Jeykumari et al. "Covalent Modification of Multiwalled Carbon Nanotubes with Neutral Red for the Fabrication of an Amperometric Hydrogen Peroxide Sensor", Nanotechnology 18(125501): 1-10, 2007.
Kleps et al. "Investigation of Silver-, Meso- and Nanoporous Silicon Composite Layers for Biomedical Applications", Romanian Journal of Information Science and Technology, 10(1): 97-111, 2007.
Kosaka et al. "Detection of Cancer Biomarkers in Serum Using A Hybrid Mechanical and Optoplasmonic Nanosensor", Nature Nanotechnology, 9(12): 1047-1053, Published Online Nov. 2, 2014.
Kraly et al. "Review: Microfluidic Applications in Metabolomics and Metabolic Profiling", Analytica Chimica Acta, 653(1): 23-35, Available Online Sep. 1, 2009.
Krivitsky et al. "Antigen-Dissociation From Antibody-Modified Nanotransistor Sensor Arrays as A Direct Biomarker Detection Method in Unprocessed Biosamples", Nano Letters, 16(10): 6272-6281, Aug. 31, 2016.
Krivitsky et al. "Si Nanowires Forest-Based On-Chip Biomolecular Filtering, Separation and Preconcentration Devices: Nanowires Do It All", Nano Letters, 12(9): 4748-4756, Aug. 2, 2012.
Li et al. "Sequence-Specific Label-Free DNA Sensors Based on Silicon Nanowires", Nano Lelters, 4(2): 245-247, Published on Web Jan. 8, 2004.

Lin et al. "Microscale LC-MS-NMR Platform Applied to the Identification of Active Cyanobacterial Metabolites", Analytical Chemistry, 80(21): 8045-8054, Nov. 1, 2008.
Lu et al. "A Nano-Ni Based Ultrasensitive Nonenzymatic Electrochemical Sensor for Glucose: Enhancing Sensitivity Through A Nanowire Array Strategy", Biosensors and Bioelectronics, 25(1): 218-223, Published Online Jul. 7, 2009.
Lu et al. "Enzyme-Functionalized Gold Nanowires for the Fabrication of Biosensors", Bioelectrochemistry, 71(2): 211-216, Published Online Jun. 14, 2007.
Lu et al. "Label-Free and Rapid Electrical Detection of hTSH With CMOS-Compatible Silicon Nanowire Transistor Arrays", ACS Applied Materials & Interfaces, 6(22): 20378-20384, Oct. 22, 2014. Figs.4a, 4b, Table 1, p. 20381,1-h col., Last Para.
Marx "Tracking Metastasis and Tricking Cancer", Nature, 494(7435): 131-136, Feb. 7, 2013.
McAlpine et al. "Highly Ordered Nanowire Arrays on Plastic Substrates for Ultrasensitive Flexible Chemical Sensors", Nature Materials, 6(5): 379-384, May 2007.
Mohanty et al. "Field Effect Transistor Nanosensor for Breast Cancer Diagnostics", ArXiv Preprint ArXiv, 1401.1168: 1-25, Jan. 6, 2014. p. 5, Section B, p. 10, 2nd Para, p. 14, 3rd Para.
Mu et al. "Silicon Nanowire Field-Effect Transistors—A Versatile Class of Potentiometric Nanobiosensors", IEEE Access, 3: 287-302, Apr. 22, 2015. p. 293, 1-h col., 4th Para, p. 290, r-h col., 1st Para.
Munoz-Pinedo et al. "Cancer Metabolism: Current Perspectives and Future Directions", Cell Death and Disease, 3(1): e248-1-e248-10, Published Online Jan. 12, 2012.
Noor et al. "Silicon Nanowires as Field-Effect Transducers for Biosensor Development: A Review", Analytica Chimica Acta, 825: 1-25, Available Online May 15, 2014.
Northen et al. "Clathrate Nanostructures for Mass Spectrometry", Nature, 449(7165): 1033-1037, Oct. 25, 2007.
Patolsky "Nanotechnology Tools in Biology and Medicine Applications", YouTube [Online], Presentation, Summer School on Nanomedicine and Innovation, The Marian Gertner Institute for Medical Nanosystems, Raymond and Beverly Sackler School of Chemistry, Tel Aviv University, Israel, Jun. 19, 2014. Video: 45:13-49:10 (mm:ss).
Patolsky et al. "Electrical Detection of Single Viruses", Proc. Natl. Acad. Sci. USA, PNAS, 101(39): 14017-14022, Sep. 28, 2004.
Patolsky et al. "Fabrication of Silicon Nanowire Devices for Ultrasensitive, Label-Free, Real-Time Detection of Biological and Chemical Species", Nature Protocols, 1(4): 1711-1724, Published Online Nov. 16, 2006.
Patolsky et al. "Nanowire-Based Biosensors", Analytical Chemistry, 78(13): 4260-4269, Jul. 1, 2006.
Peretz-Soroka et al. "Optically-Gated Self-Calibrating Nanosensors: Monitoring pH and Metabolic Activity of Living Cells", Nano Letters, 13(7): 3157-3168, Jun. 17, 2013.
Ramgir et al. "Nanowire-Based Sensors", Small, 6(16): 1705-1722, Aug. 16, 2010.
Shaijumon et al. "Catalytic Growth of Carbon Nanotubes Over Ni/Cr Hydrotalcite-Type Anionic Clay and Their Hydrogen Storage Properties", Applied Surface Science, 242: 192-198, 2005.
Shao et al. "Silicon Nanowire Sensors for Bioanalytical Applications: Glucose and Hydrogen Peroxide Detection", Advanced Functional Materials, 15(9): 1478-1482, Sep. 2005.
Shulaev "Metabolomics Technology and Bioinformatics", Briefings in Bioinformatics, 7(2): 128-139, May 18, 2006.
Stem et al. "Label-Free Biomarker Detection From Whole Blood", Nature Nanotechnology, 5(2): 138-142, Published Online Dec. 13, 2009.
Stem et al. "Semiconducting Nanowire Field-Effect Transistor Biomolecular Sensors", IEEE Transactions on Electron Devices, 55(11): 3119-3130, Nov. 2008.
Su et al. "A Silicon Nanowire-Based Electrochemical Sensor With High Sensitivity and Electrocatalytic Activity", Particle Particle Systems Characterization, 30(4): 326-331, Apr. 2013.
Telg et al. "G– and G+ in the Raman Spectrum of Isolated Nanotube: A Study on Resonance Conditions and Lineshape", Physica Status Solidi (b), 245(10): 2189-2192, 2008.

(56) References Cited

OTHER PUBLICATIONS

Timko et al. "Electrical Recording From Hearts With Flexible Nanowire Device Arrays", Nano Letters, 9(2): 914-918, Published on Web Jan. 26, 2009.
Tyagi et al. "Patternable Nanowire Sensors for Electrochemical Recording of Dopamine", Analytical Chemistry, 81(24): 9979-9984, Dec. 15, 2009.
Vlckova et al. "Determination of Cationic Neutrotransmitters and Metabolites in Brain Homogenates by Microchip Electrophoresis and Carbon Nanotube-Modified Amperometry", Journal of Chromatography A, 1142(2): 214-221, 2007.
Wanekeya et al. "Nanowire-Based Electrochemical Biosensors", Electroanalysis, XP055167317, 18(6): 533-550, Mar. 1, 2006.
Wang et al. "A NEMS Thermal Biosensor for Metabolic Monitoring Applications", Journal of Microelectromechanical Systems, 17(2): 318-327, Apr. 2008.
Wang et al. "Simultaneous Microchip Enzymatic Measurements of Blood Lactate and Glucose", Analytica Chimica Acta, 585(1): 11-16, Published Online Dec. 9, 2006.
Yang et al. "Gold Nanoparticle Modified Silicon Nanowires as Biosensors", Nanotechnology, 17(11): S276-S279, May 19, 2006.
Yin et al. "A Hydrogen Peroxide Electrocheinical Sensor Based on Silver Nanopartides Decorated Silicon Nanowire Arrays" Electrochimica Acta, 56: 3884-3889, 2011.
Yun et al. "On-Line Carbon Nanotube-Based Biosensors in Microfluidic Channels", Nanosensors, Microsensors, and Biosensors and Systems, Proceedings of the SPIE, XP055167836, 6528: 65280-1-65280-10, Apr. 4, 2007. Abstract, Figs.3-5.
Zayats et al. "An Integrated NAD+Dependent Enzyme-Functionalized Field-Effect Transistor (ENFET) System: Development of A Lactate Biosensor", Biosensor & Bioelectronics, XP055450950, 15(11-12): 671-680, Dec. 1, 2000.
Zheng et al. "Multiplexed Electrical Detection of Cancer Markers With Nanowire Sensor Arrays", Nature Biotechnology, 23(10): 1294-1301, Oct. 2005.
Communication Pursuant to Article 94(3) EPC dated Oct. 15, 2021 From the European Patent Office Re. Application No. 16872559.6. (3 Pages).
Notice of Reasons for Rejection dated Oct. 9, 2018 From the Japan Patent Office Re. Application No. 2016-525073 and Its Translation Into English. (10 Pages).

* cited by examiner

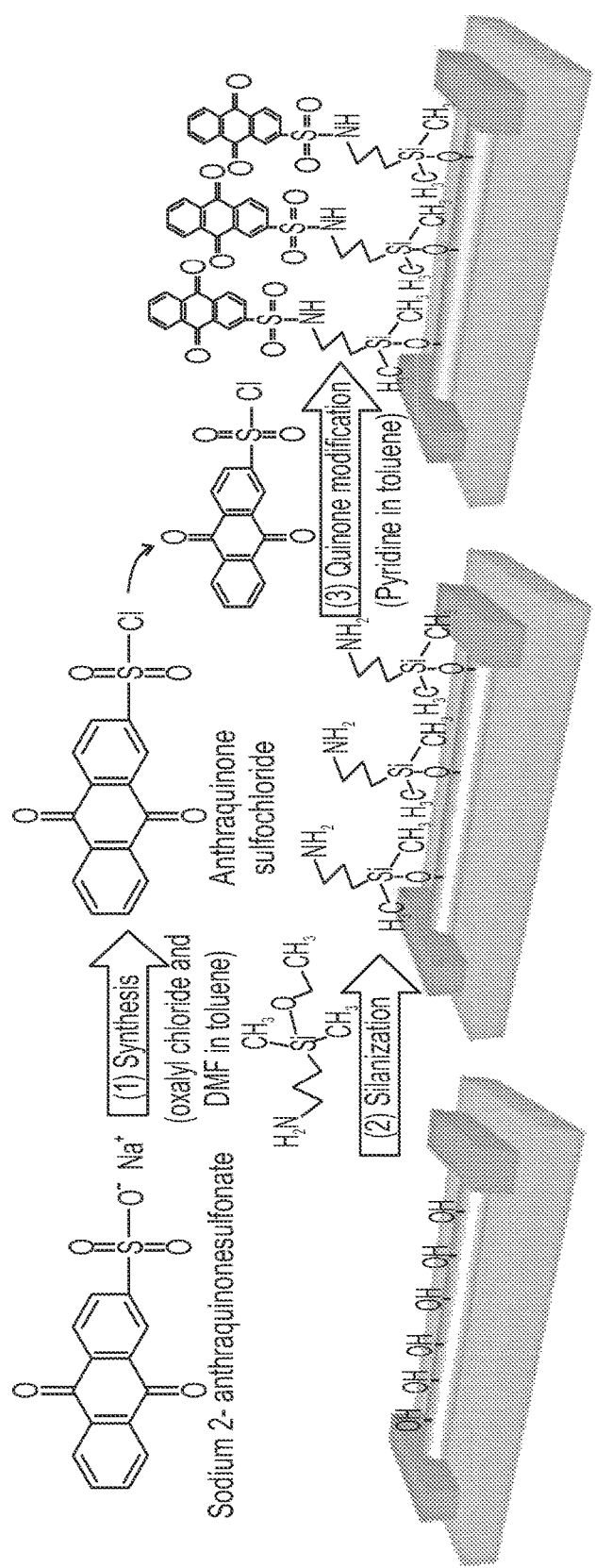
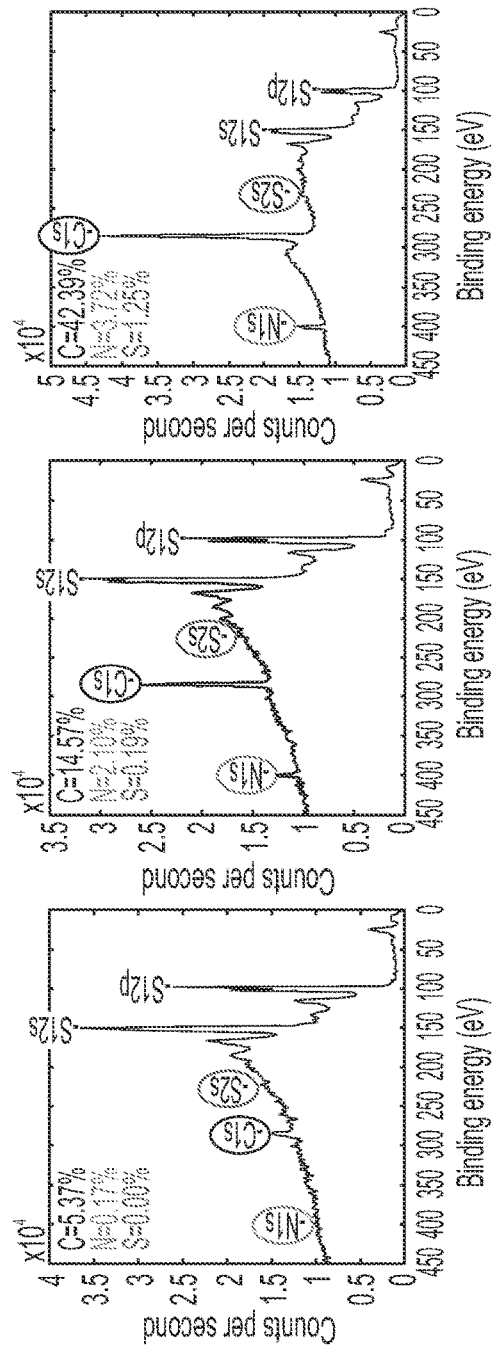
FIG. 2A  FIG. 2B  FIG. 2C

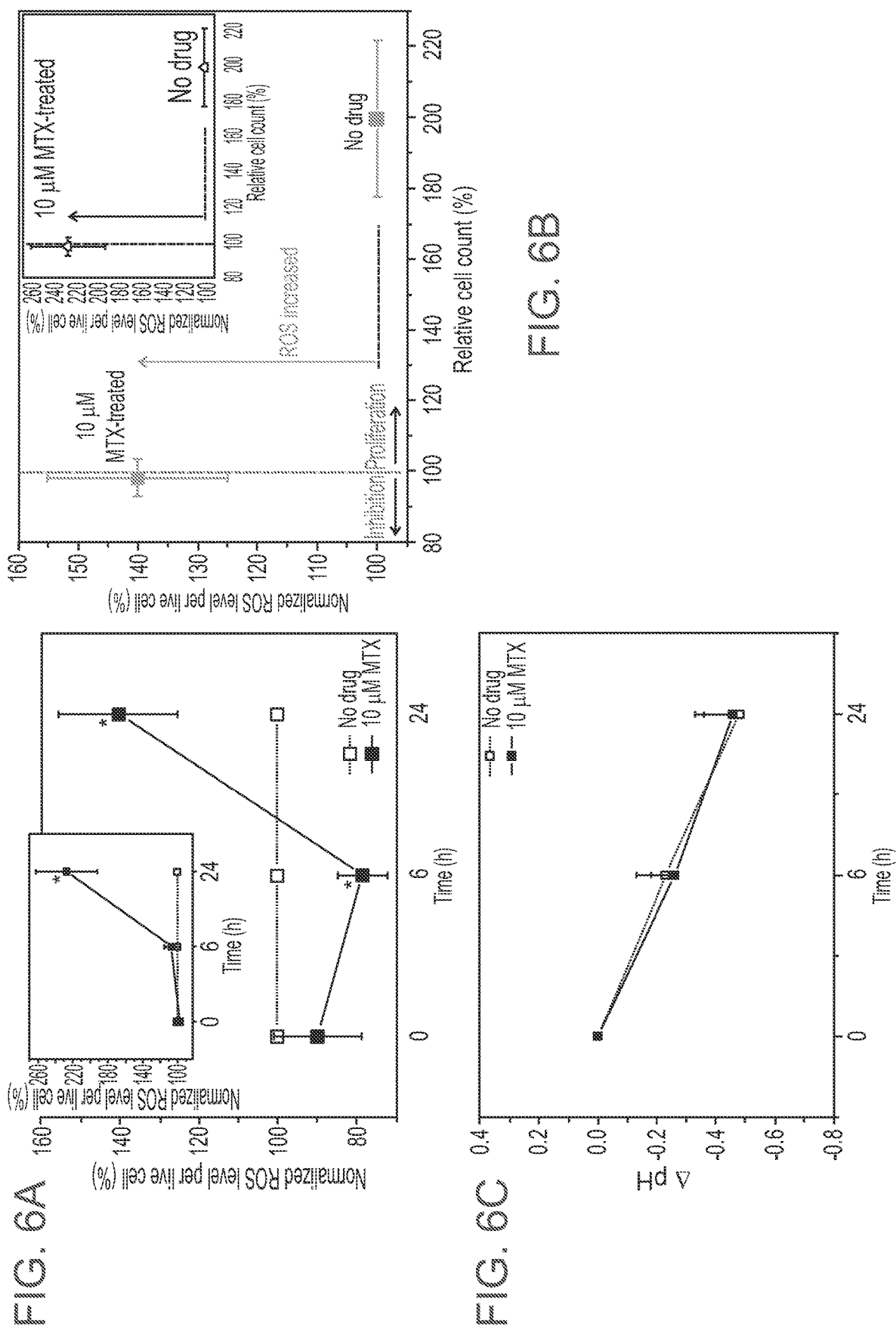

METHOD AND SYSTEM FOR SENSING

RELATED APPLICATION

This application is a National Phase of PCT Patent Application No. PCT/IL2016/051320 having International filing date of Dec. 8, 2016, which claims the benefit of priority under 35 USC § 119(e) of U.S. Provisional Patent Application Nos. 62/264,913 and 62/264,944, both filed on Dec. 9, 2015. The contents of the above applications are all incorporated by reference as if fully set forth herein in their entirety.

FIELD AND BACKGROUND OF THE INVENTION

The present invention, in some embodiments thereof, relates to sensing and, more particularly, but not exclusively, to systems and methods which can be utilized, for example, for real-time simultaneous detection of a variety of samples and/or for real-time detection of redox-reactive moieties such as, for example, oxidizing moieties produced by metabolites. The systems and methods described herein can be utilized, for example, for monitoring and/or analyzing metabolic activity of cells, and hence in various diagnostic and/or therapeutic applications.

Metabolism is defined as the totality of biochemical processes in living organisms that either produce or consume energy. Metabolic processes regulate cells to grow or die, reform their structures, and respond to their environments. Abnormal metabolic reactions disturb normal physiology and lead to severe tissue dysfunction, and are linked to many diseases.

Cancer is an example of a common human disease with metabolic perturbations. Altered cellular metabolism is a hallmark of cancer, contributing to malignant transformation and to the initiation, growth, and maintenance of tumors. Thus, for example, studies have shown that altered glucose metabolism promotes cancer development, and that cancer cells consume much more glucose and secrete much more lactate than normal tissue.

Understanding the complex networks associated with cancer metabolism for monitoring thereof have therefore been recognized as desirable for distinguishing metabolic significances of cancers, estimating the effectiveness of therapies, and facilitating personalized treatments. See, for example, Munoz-Pinedo et al. Cell Death Dis 2012, 3: e248; and Griffin and Shockcor, Nature reviews Cancer 2004, 4(7): 551-561.

Several methodologies have been used heretofore for monitoring metabolic activities of cells. The most prevalent are mass spectrometry (MS) techniques linked with a separation method such as gas (GC) or liquid (LC) chromatography. In MS, species are ionized and separated based on their mass-to-charge ratio. MS is sensitive within physiological concentration ranges of metabolites, but results are obtained in endpoint fashion, ceasing metabolic activity of samples to collect data, rather than in real-time. In addition, this methodology requires sample preprocessing, rendering it incompatible with direct testing of biosamples such as blood or serum. Alternative separation methods for MS include electrospray ionization (ESI), which improves preprocessing, and nanostructure-initiator MS (NI-MS), which allows direct detection of physiological solutions. See, for example, Shulaev V. Metabolomics technology and bioinformatics. Brief Bioinform 2006, 7(2):128-139; and Northen et al. Nature 2007, 449(7165): 1033-U1033.

For real-time sensing with multiplex profiling in physiological samples, methodologies combining electrochemical and fluorescent sensing techniques have been sought for. Enzyme-reactive electrochemical sensors combining $H_2O_2$-detecting electrodes with enzyme-modified membranes to convert metabolites to $H_2O_2$ for real-time sensing have been developed [Pörtner R. Animal cell biotechnology: methods and protocols, 2nd edn. Humana Press: Totowa, N.J., 2007]. A fluorescent sensor with embedded fluorophores for detecting $O_2$ consumption and pH change of biosamples in real time has also been developed [Marx V. Nature 2013, 494 (7435), p. 131].

WO 2012/137207 describes a method of measuring a metabolic activity of a cell, effected by independently measuring in an extracellular environment of the cell, time-dependent acidification profiles due to secretion of non-volatile soluble metabolic products; non-volatile soluble metabolic products and volatile soluble metabolic products; and volatile soluble metabolic products, and uses of such a method for diagnosing and monitoring disease treatment.

Recent developments in microfluidic technology and nanotechnology have also been exploited for supersensitive real-time detection of micro-volume metabolites. Microfluidic devices which separate microlevels of metabolites in solution using electrophoresis [Garcia-Perez et al. Journal of Chromatography A 2008, 1204(2): 130-139; Garcia and Henry Anal Chim Acta 2004, 508(1): Wang et al. Anal Chim Acta 2007, 585(1): 11-16; et al. Analyst 2009, 134(3): 486-492; and Vlckova and Schwarz J Chromatogr A 2007, 1142(2): 214-221] or liquid chromatography [Wang L et al. J Microelectromech S 2008, 17(2): 318-327; Lin et al. Anal Chem 2008, 80(21): 8045-8054], have been described. Currently used microfluidic chips, however, require coupling to other detection techniques and thus require preprocessing [Kraly et al. Anal Chim Acta 2009, 653(1): 23-35].

Electrochemical, photochemical, and antibody/enzyme-functionalized nanowire sensors have also been described for detecting target metabolites. See, for example, Ramgir et al. Small 2010, 6(16): 1705-1722; and Peretz-Soroka et al. Nano Lett 2013, 13(7): 3157-3168.

Antibody/enzyme nanowire FET devices which target metabolites via binding affinity have been disclosed in, for example, Lu et al. *Bioelectrochemistry* 2007, 71(2): 211-216; Patolsky et al. Nanowire-based biosensors. *Anal Chem* 2006, 78(13): 4260-4269; and Yang et al. *Nanotechnology* 2006, 17(11): S276-S279.

Electrochemically-sensitive nanowire sensors for detecting metabolites by oxidative reactions have been disclosed in, for example, Lu et al. Biosens Bioelectron 2009, 25(1): 218-223; Krivitsky et al. Nano letters 2012, 12(9): 4748-4756; Shao et al. Adv Funct Mater 2005, 15(9): 1478-1482; Su et al. Part Part Syst Char 2013, 30(4): 326-331; and Tyagi et al. Anal Chem 2009, 81(24): 9979-9984.

Semiconducting nanowires are known to be extremely sensitive to chemical species adsorbed on their surfaces. For a nanowire device, the binding of a charged analyte to the surface of the nanowire leads to a conductance change, or a change in current flowing through the wires. The 1D (one dimensional) nanoscale morphology and the extremely high surface-to-volume ratio make this conductance change to be much greater for nanowire-based sensors versus planar FETs (field-effect transistors), increasing the sensitivity to a point that single molecule detection is possible.

Nanowire-based field-effect transistors (NW-FETs) have therefore been recognized in the past decade as powerful potential new sensors for the detection of chemical and biological species. See, for example, Patolsky et al., Analytical Chemistry 78, 4260-4269 (2006); Stern et al., IEEE Transactions on Electron Devices 55, 3119-3130 (2008); Cui et al., Science 293, 1289-1292 (2001); Patolsky et al. Proceedings of the National Academy of Sciences of the United States of America 101, 14017-14022 (2004), all being incorporated by reference as if fully set forth herein.

Studies have also been conducted with nanowire electrical devices for the simultaneous multiplexed detection of multiple biomolecular species of medical diagnostic relevance, such as DNA and proteins [Zheng et al., Nature Biotechnology 23, 1294-1301 (2005); Timko et al., Nano Lett. 9, 914-918 (2009); Li et al., Nano Lett. 4, 245-247 (2004)].

Generally, in a NW-FET configuration, the gate potential controls the channel conductance for a given source drain voltage (VSD), and modulation of the gate voltage (VGD) changes the measured source-drain current (ISD). For NW sensors operated as FETs, the sensing mechanism is the field-gating effect of charged molecules on the carrier conduction inside the NW. Compared to devices made of micro-sized materials or bulk materials, the enhanced sensitivity of nanodevices is closely related to the reduced dimensions and larger surface/volume ratio. Since most of the biological analyte molecules have intrinsic charges, binding on the nanowire surface can serve as a molecular gate on the semiconducting SiNW [Cui et al., 2001, supra].

U.S. Pat. No. 7,619,290, U.S. Patent Application having publication No. 2010/0022012, and corresponding applications, teach nanoscale devices composed of, inter alia, functionalized nanowires, which can be used as sensors.

Clavaguera et al. disclosed a method for sub-ppm detection of nerve agents using chemically functionalized silicon nanoribbon field-effect transistors [Clavaguera et al., Angew. Chem. Int. Ed. 2010, 49, 1-5].

$SiO_2$ surface chemistries were used to construct a 'nanoelectronic nose' library, which can distinguish acetone and hexane vapors via distributed responses [Nature Materials Vol. 6, 2007, pp. 379-384].

U.S. Patent Application having Publication No. 2010/0325073 discloses nanodevices designed for absorbing gaseous NO. WO 2011/000443 describes nanodevices which utilize functionalized nanowires for detecting nitro-containing compounds.

SUMMARY OF THE INVENTION

A sensing methodology that integrates multiplexing and real-time capabilities, direct detection of biosamples, and minimum sample requirements, is highly required. Such a system can be utilized, for example, for monitoring and analyzing metabolic activity of cells. Such a methodology should allow detection without altering metabolite production, or perturbing extracellular concentrations of associated species.

The present inventors have devised and successfully prepared and practiced an integrated microfluidic nanostructure sensing system, comprised of one or more sensing compartments featuring a functionalized (e.g., redox-reactive) nanostructure FET array which is in fluid communication with one or more sample chambers. This system has been shown to perform multiplex real-time monitoring of cellular metabolic activity in physiological solutions, and was demonstrated as an efficient tool in promoting the understanding of metabolic networks and requirements of cancers for personalized medicine.

According to an aspect of some embodiments of the present invention there is provided a system for sensing metabolic activity. The system comprises: a sensing element comprising a transistor having a gate electrode and a semiconductor nanostructure connecting between a source electrode and a drain electrode and being modified by a functional moiety covalently attached thereto; and a voltage source connected to the gate electrode; a controller configured for controlling a gate voltage applied by the voltage source to the gate electrode such as to reverse a redox reaction occurring when the moiety contacts a redox reactive agent; and a circuit for detecting changes in an electrical property of the nanostructure.

According to some embodiments of the invention the functional moiety is a redox reactive moiety.

According to some embodiments of the invention the sensing element comprises at least one additional transistor having a nanostructure modified by a non-redox active moiety, wherein the detector circuit is configured to subtract signals received from the nanostructure modified by the redox active moiety, from signals received from the nanostructure modified by the non-redox active moiety.

According to some embodiments of the invention the system is contained in a skin-attachable sticker.

According to some embodiments of the invention the system is contained in a housing implantable in a living body.

According to an aspect of some embodiments of the present invention there is provided a method of sensing metabolic activity in a living organism. The method comprises: contacting the living organism with a sensing element comprising a transistor having a gate electrode and a semiconductor nanostructure connecting between a source electrode and a drain electrode and being modified by a functional moiety covalently attached thereto; detecting changes in an electrical property of the nanostructure resulting from redox reaction occurring during the contact; and applying gate voltage to the gate electrode so as to reverse the redox reaction.

According to some embodiments of the invention the gate voltage is selected to maintain a generally constant population of the functional moiety on the nanostructure.

According to some embodiments of the invention the gate voltage is constant.

According to some embodiments of the invention the gate voltage is from about −3 volts to about +3 volts.

According to an aspect of some embodiments of the present invention there is provided a system comprising at least one chamber being in controllable fluid communication with a sensing compartment, the at least one chamber being configured to contain a fluid and the sensing compartment comprising a semiconductor nanostructure and a functional moiety covalently attached to the nanostructure, the functional moiety being such that upon contacting a redox reactive agent, the nanostructure exhibits a detectable change in an electrical property.

According to some of any of the embodiments of the present invention, the functional moiety is a redox reactive moiety.

According to some of any of the embodiments of the present invention, the functional moiety comprises at least one functional group capable of reversible change in an oxidation number or oxidation state of at least one of its atoms.

According to some of any of the embodiments of the present invention, the functional moiety comprises a quinone.

According to some of any of the embodiments of the present invention, the functional moiety comprises an aromatic quinone.

According to some of any of the embodiments of the present invention, the functional moiety or comprises a functional group elected from the group consisting of quinone, benzoquinone, anthraquinone, and phenanthrenequinone, each being substituted or unsubstituted.

According to some of any of the embodiments of the present invention, the electrical property comprises electron or charge density on a surface of the nanostructure.

According to some of any of the embodiments of the present invention, the nanostructure is a nanowire.

According to some of any of the embodiments of the present invention, the semiconductor nanostructure comprises silicon.

According to some of any of the embodiments of the present invention, the system further comprises a detector constructed and arranged to determine the change in electrical property.

According to some of any of the embodiments of the present invention, the semiconductor nanostructure is a transistor.

According to some of any of the embodiments of the present invention, the system comprises a plurality of the nanostructures.

According to some of any of the embodiments of the present invention, the nanostructures are substantially identical.

According to some of any of the embodiments of the present invention, the nanostructures are included in the same sensing compartment and are in fluid communication thereamongst at all times.

According to some of any of the embodiments of the present invention, the system further comprises a substrate onto and/or into which the nanostructure is, or the plurality of nanostructures are, deposited.

According to some of any of the embodiments of the present invention, the system comprises at least two chambers, each being configured to contain a fluid and being in fluid communication with the sensing compartment.

According to some of any of the embodiments of the present invention, the at least two chambers are in fluid communication therebetween.

According to some of any of the embodiments of the present invention, the system further comprises a valve configured to control a fluid communication between each of the chambers and the sensing compartment and/or between the chambers.

According to some of any of the embodiments of the present invention, the fluid communication is effected by means of microchannels.

According to some of any of the embodiments of the present invention, the system further comprises at least one valve for respectively allowing or preventing flow from the at least one chamber to the sensing compartment.

According to some of any of the embodiments of the present invention, the system further comprises a controller, for selectively operating the at least one valve to control flow of fluids from the at least one chamber to the sensing compartment.

According to some of any of the embodiments of the present invention, the system further comprises an additional sensing device.

According to some of any of the embodiments of the present invention, the additional sensing device comprises an optical sensing device.

According to some of any of the embodiments of the present invention, the system further comprises an additional chamber being devoid of the semiconductor nanostructure and also in fluid communication with the at least one chamber, wherein the additional sensing device is configured to receive signals from the additional chamber.

According to an aspect of some embodiments of the present invention there is provided a method of determining a presence and/or amount of a redox reactive agent in at least one fluid sample, the method comprising introducing the at least one sample to the sensing system according to any one of the embodiments described herein, wherein the detectable change in the electrical property is indicative of the presence and/or amount of the redox reactive agent in each of the at least one sample.

According to an aspect of some embodiments of the present invention there is provided a method of determining a presence and/or amount of a substance producing a redox reactive agent in at least one fluid sample, the method comprising introducing the at least one sample to the sensing system according to any one of the embodiments described herein, wherein the detectable change in the electrical property is indicative of the presence and/or amount of the substance in each of the at least one sample.

According to some of any of the embodiments of the present invention, the method further comprises subjecting at least one fluid sample to a reaction condition under which the substance produces the redox reactive agent.

According to some of any of the embodiments of the present invention, the subjecting comprises fluidly communicating the chamber with a chamber which provides the condition.

According to some of any of the embodiments of the present invention, the subjecting comprises fluidly communicating a chamber which provides the condition with the sensing compartment.

According to some of any of the embodiments of the present invention, the condition comprises an enzymatic reaction that catalyzes a production of the oxidizing agent or the reducing agent by the substance.

According to some of any of the embodiments of the present invention, the chamber which provides the condition forms a part of the sensing system.

According to some of any of the embodiments of the present invention, at least one fluid sample comprises a cell, the method being for determining a presence and/or an amount of the substance producing the oxidizing agent or the reducing agent in the cell.

According to some of any of the embodiments of the present invention, the substance is a metabolite.

According to some of any of the embodiments of the present invention, at least one fluid sample comprises a cell, the method being for determining or monitoring metabolic activity of the cell.

According to some of any of the embodiments of the present invention, at least one fluid sample which comprises the cell further comprises a therapeutic agent, the method being for determining or monitoring activity of the cell upon contacting the therapeutic agent.

According to some of any of the embodiments of the present invention, the method is being for determining an efficacy of the therapeutic agent towards the cell.

According to some of any of the embodiments of the present invention, the substance is a metabolite, the method being for identifying an agent capable of altering a metabolic activity of the cell.

According to some of any of the embodiments of the present invention, the fluid sample is a biological sample of a subject.

According to some of any of the embodiments of the present invention, the method is being for diagnosing a disease associated with a modified metabolic activity in a subject.

According to some of any of the embodiments of the present invention, the method is being for monitoring a treatment of a disease associated with a modified metabolic activity in a subject.

According to some of any of the embodiments of the present invention, the oxidizing agent is a reactive oxygen species or an agent producing a reactive oxygen species.

According to some of any of the embodiments of the present invention, the oxidizing agent is a peroxide.

According to an aspect of some embodiments of the present invention there is provided a sensing system, comprising:

a sensing compartment configured for detecting a target molecule;

a plurality of chambers, each being in controllable fluid communication with the same sensing compartment via a respective microchannel and a respective valve mounted thereon; and a controller, for selectively operating each valve to control flow of fluids from at least two of the chambers to the sensing compartment.

According to some of any of the embodiments of the present invention, the sending compartment comprises a semiconductor nanostructure configured such that upon contacting a target molecule, the nanostructure exhibits a detectable change in an electrical property thereof.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 2A-D present the data obtained in XPS measurements during surface modification and characterization of redox-reactive SiNW FETs. Modification procedures: conversion of the sulfonate group of sodium 9,10-anthraquinone-2-sulfonate to sulfochloride (inset); silanization of the SiNW surface with amine groups (FIG. 2B); and formation of the sulfonamide that connects 9,10-anthraquinone group to the modified surface (FIG. 2C). XPS spectra and atomic compositions of the modified surface for carbon (C), nitrogen (N) and sulfur (S) of a non-modified SiNW FET (FIG. 2A) and upon each modification step are presented. FIG. 2D presents XPS representative survey spectra of the oxidized 9,10-anthraquinone-modified silicon nanowire surface and reduced 9,10-dihydroxyanthracene-modified silicon nanowire surface. Percentage of C=O bonds was calculated from C1s curve fitting.

FIG. 3A presents oxidation kinetics of the 9,10-dihydroxyanthracene-modified FET in different concentrations of $H_2O_2$, and reduction of the FET surface by flowing a reductant solution, compared to signals acquired from an APDMES-modified FET. ($\Delta I_{ds}$: the difference between a measured current and a baseline; Io: normalizing factor; $V_g$=0 V; $V_{ds}$=0.2 V; sensing was performed at pH 7.4 in serum-added culture medium).

Comparisons of surface chemical bond populations for relevant functional groups at oxidation and reduction are presented in insets. FIG. 3B presents sensing responses of a 9,10-dihydroxyanthracene-modified SiNW FET modeled as a function of $H_2O_2$ concentration and pH (data were means±standard deviations (SD), n≥4 replications).

FIG. 5A presents a schematic illustration of the conversion of the modified FET into a pH sensor by adding a reductant, depicting changes in surface proton density in response to protonation or by deprotonation, which change the measured current. FIG. 5B presents pH-dependent sensing response in reductant-added medium without $H_2O_2$ content (Vg=−0.3 V; Vds=0.2 V). FIG. 5C demonstrates the sensor's insensibility to $H_2O_2$ in a reductant-added medium. Base levels obtained by flowing a reductant (Vg=0 V (reductant-free), −0.3 V (reductant-added); Vds=0.2 V). Signals were obtained after 700 seconds of injection; sensing was done at pH 8.00 in serum-added culture medium.

FIGS. 6A-I present data obtained while monitoring of cellular metabolic activity using a 9,10-dihydroxyanthracene-modified NW FET). Measured levels of metabolites were normalized by the number of live cells. FIGS. 6A and 6D present data obtained during 24-hour monitoring of MTX-treated and 2DG-treated Jurkat cells, respectively. FIGS. 6B and 6E show the correlations between ROS levels and resultant cell proliferation rates after 24 hours in MTX-treated and 2DG-treated Jurkat cells. Relative cell count is a ratio of the cell count at t=24 hour to the initial cell count. FIG. 6F show the correlation between lactate levels of 2DG-treated Jurkat cells and resultant cell proliferation rates after 24 hours. Data of control experiments, in all insets of FIGS. 6A, B, D and E, were obtained by using dichlorodihydrofluorescein. FIGS. 6C and 6G show the pH of MTX-treated and 2DG-treated Jurkat cells, respectively. The measured metabolic levels of CLL cells were normalized by those of normal B cells. Data were means±standard error of the mean (SEM), n≥3 replications; n=6 devices; Student's t-tests were employed; * denotes $P<0.05$, ** denotes $P<0.01$). FIGS. 6H-6I present data obtained in 24-hour viability observation of (MTX-treated and 2DG-treated Jurkat cells, respectively.

Figure 1A:
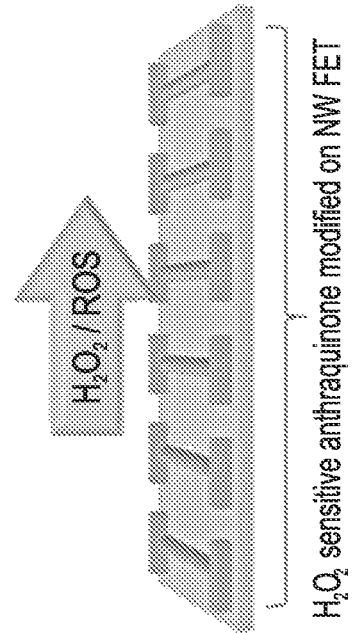
FIGS. 1A-D present images (FIGS. 1A-B) and schematic illustrations (FIGS. 1C-D) of an exemplary biosensing system according to some embodiments of the present invention. The biosensing system includes a culture compartment, in which different samples can be easily switched for multiplex sensing, and a NW-FET sensing compartment (FIGS. 1A-B). In the sensing compartment, a Silicon Nanowire (SiNW) FET array is modified with 9,10-anthraquinone-2-sulfochloride as an exemplary redox-reactive group (FIG. 1C). ROS or consequent $H_2O_2$ produced by enzymatic oxidation of metabolites oxidizes 9,10-dihydroxyanthracene on a FET surface to form 9,10-anthraquinone, thereby decreasing surface electron density, whereas a reductant, N,N-diethylhydroxylamine (DEHA), reduces 9,10-anthraquinone to 9,10-dihydroxyanthracene, thereby increasing surface electron density (FIG. 1D). (LOX: lactate oxidase; GOX: glucose oxidase; PDX: pyruvate oxidase; Pi: inorganic phosphate).

DESCRIPTION OF SPECIFIC EMBODIMENTS
OF THE INVENTION

The present invention, in some embodiments thereof, relates to sensing and, more particularly, but not exclusively, to systems and methods which can be utilized, for example, for real-time simultaneous detection of a variety of samples and/or for real-time detection of redox-reactive moieties such as, for example, oxidizing moieties produced by metabolites. The systems and methods described herein can be utilized, for example, for monitoring and/or analyzing metabolic activity of cells, and hence in various diagnostic and/or therapeutic applications.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present inventors have devised and successfully prepared and practiced an integrated microfluidic nanowire sensing system, comprised of one or more sensing compartments featuring a functionalized (e.g., redox-reactive) nanowire FET array which is in fluid communication with one or more chambers, and have successfully utilized this system for multiplex real-time monitoring of cellular metabolic activity in physiological solutions.

The present inventors have shown that using such a system, real-time multiplex monitoring of various samples can be performed, without pre-processing the sample and without interfering with its essential features and/or using hazardous agents.

Such a system can be used for various diagnosis and therapeutic applications, for example, in diagnosing a disease associate with metabolic activity, in a following selection of suitable (e.g., personalized) therapy, in monitoring the efficacy of a disease treatment, and in screening methods for therapeutic agents for altering metabolic activity of cells.

The multiplex real-time monitoring by the systems as described herein circumvents the need of pre-processing a sample before analyzing, and further, in case additional one or more reagents should be used to generate a moiety to be sensed, allows for direct mixing these reagents with the tested sample within the system. Such direct mixing allows using small amounts (e.g., microvolumes) of such reagents and mild conditions and procedures for generating the moiety to be sensed, yet results in maximizing the moiety to be sensed, improved sensing reliability and prolonged lifetime of the sensing system.

In addition, a sensing system as described herein substantially reduces the time required for sensing a sample using other techniques, and can be designed so as to be non-specific for a certain target moiety, such that multiplex sensing can be effected simultaneously for various samples. Sensing can be performed without interfering with cellular and/or metabolic processes of a biosample prior to its introduction to the system.

The Sensing System:

According to an aspect of some embodiments of the present invention there is provided a system comprising at least one chamber being in controllable fluid communication with a sensing compartment.

By "controllable fluid communication" it is meant a fluid path through which a flow of fluid can be allowed or prevented by means of a flow controlling means, such as, but not limited to, a valve. In some embodiments of the present invention controllable fluid communication encompasses a fluid path through which the flow rate of fluid can be varied.

The term "compartment" as used herein throughout should be understood as describing an open or closed enclosure within a system. The compartment can have at least a base and side walls. The compartment can otherwise be a portion of a system, separable from other portions of the system by its position.

In some embodiments, fluid communication is effected by means of microchannels. Such a sensing system is also referred to herein as microfluidic sensing system.

Figure 9A:
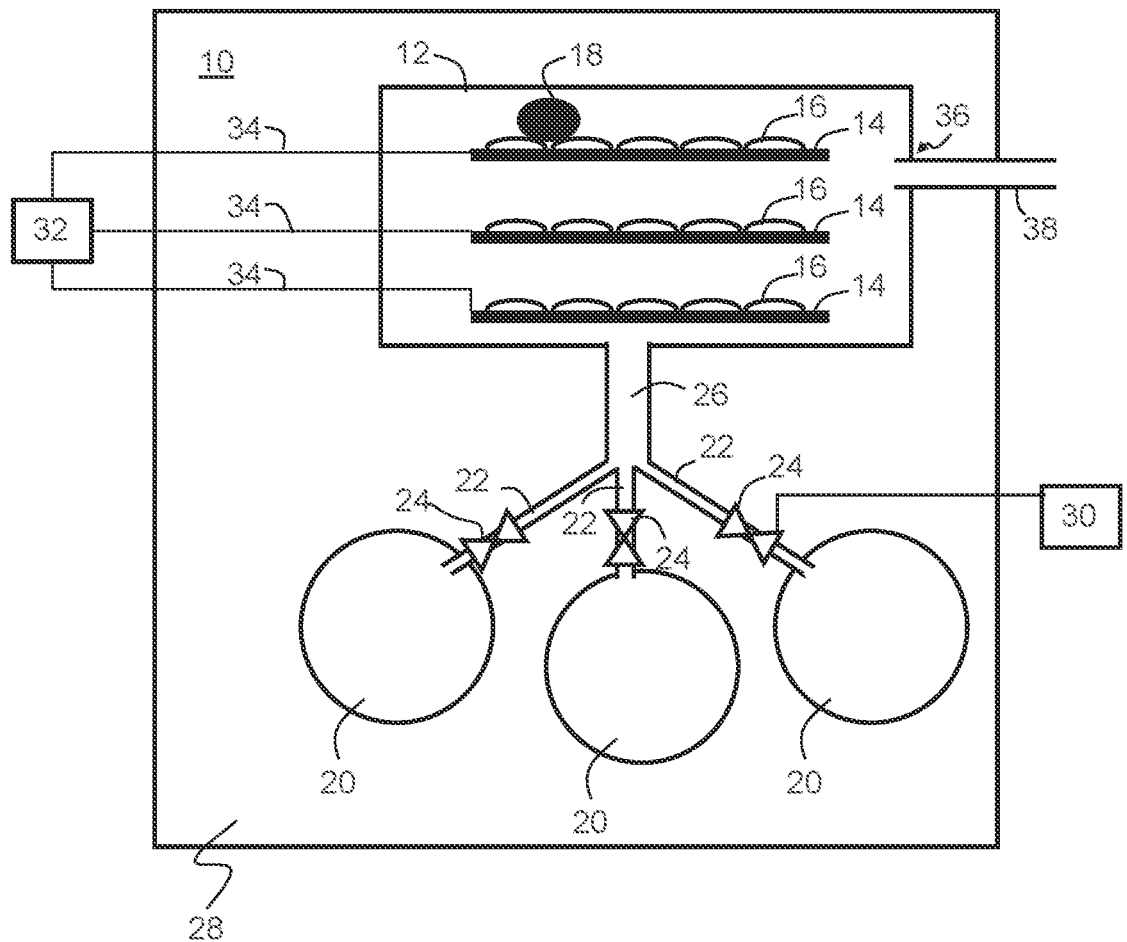
FIGS. 9A and 9B are schematic illustrations of a sensing system according to some embodiments of the present invention.
Figure 9B:
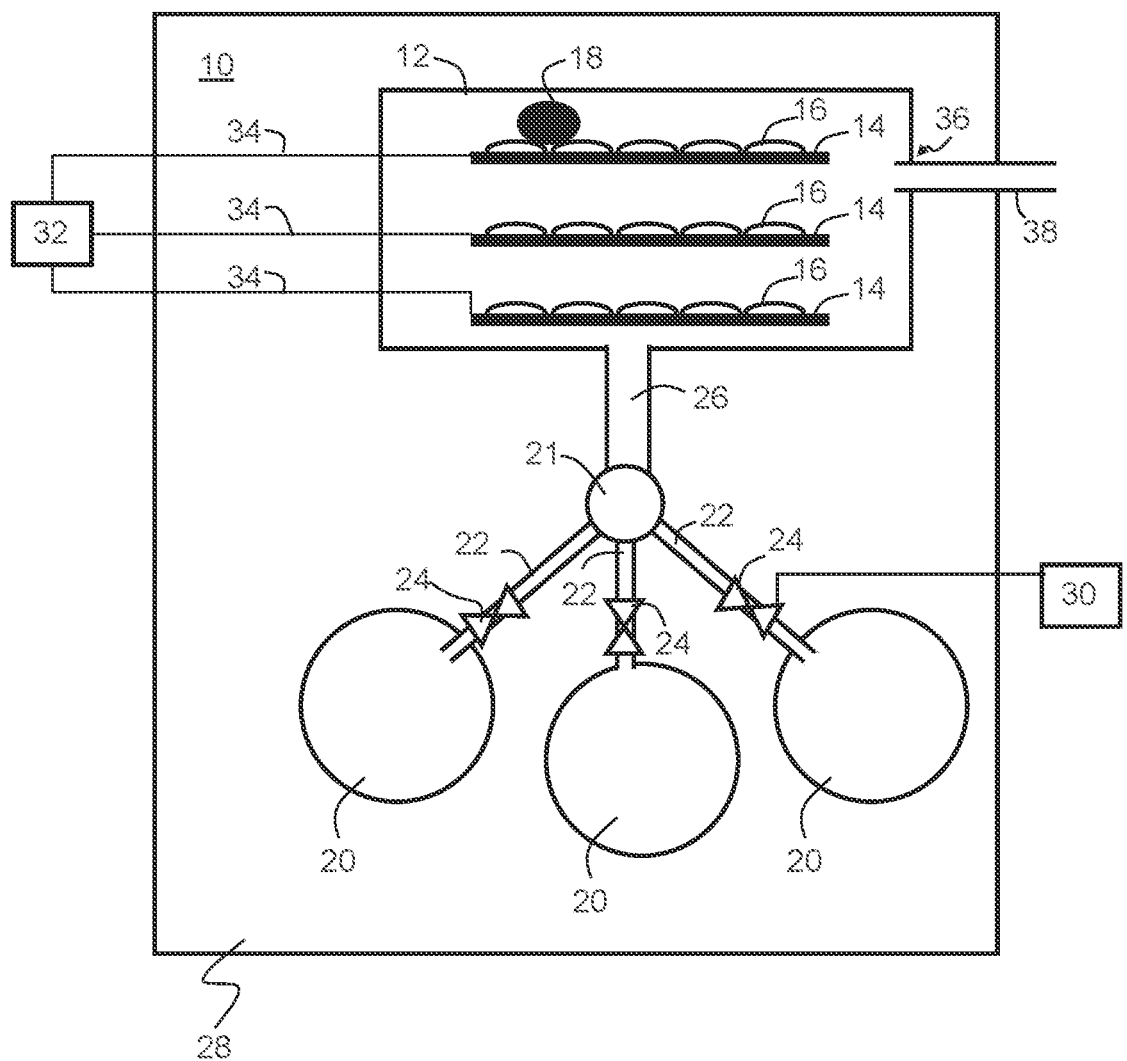

The Sensing Compartment:

Referring now to the drawings, FIGS. 9A-B are a schematic illustration of a sensing system 10 according to some embodiments of the present invention.

System 10 can comprise a sensing compartment 12 having one or more semiconductor nanostructure 14. Nanostructure 14 is preferably elongated. When a plurality (i.e., two or more) of nanostructures 14 is employed, the nanostructures 14 are optionally and preferably arranged in an array. For example, the nanostructures can be arranged generally parallel to each other, as illustrated in FIGS. 9A-B.

As used herein, a "elongated nanostructure" generally refers to a three-dimensional body which is made of a solid substance, and which, at any point along its length, has at least one cross-sectional dimension and, in some embodiments, two orthogonal cross-sectional dimensions less than 1 micron, or less than 500 nanometers, or less than 200 nanometers, or less than 150 nanometers, or less than 100 nanometers, or even less than 70, less than 50 nanometers, less than 20 nanometers, less than 10 nanometers, or less than 5 nanometers. In some embodiments, the cross-sectional dimension can be less than 2 nanometers or 1 nanometer.

In some embodiments, the nanostructure has at least one cross-sectional dimension ranging from 0.5 nanometers to 200 nanometers, or from 1 nm to 100 nm, or from 1 nm to 50 nm.

The length of a nano structure expresses its elongation extent generally perpendicularly to its cross-section. According to some embodiments of the present invention the length of the nanostructure ranges from 10 nm to 50 microns.

The cross-section of the elongated semiconductor may have any arbitrary shape, including, but not limited to, circular, square, rectangular, elliptical and tubular. Regular and irregular shapes are included.

In various exemplary embodiments of the invention the nanostructure is a non-hollow structure, referred to herein as "nanowire".

A "wire" refers to any material having conductivity, namely having an ability to pass charge through itself.

In some embodiments, a nanowire has an average diameter that ranges from 0.5 nanometers to 200 nanometers, or from 1 nm to 100 nm, or from 1 nm to 50 nm.

In some embodiments of the present invention, the nanostructure is shaped as hollow tubes, preferably entirely hollow along their longitudinal axis, referred to herein as "nanotube" or as "nanotubular structure".

The nanotubes can be single-walled nanotubes, multi-walled nanotubes or a combination thereof.

In some embodiments, an average inner diameter of a nanotube ranges from 0.5 nanometers to 200 nanometers, or from 1 nm to 100 nm, or from 1 nm to 50 nm.

In case of multi-walled nanotubes, in some embodiments, an interwall distance can range from 0.5 nanometers to 200 nanometers, or from 1 nm to 100 nm, or from 1 nm to 50 nm.

Selection of suitable semiconductor materials for forming a nanostructure as described herein will be apparent and readily reproducible by those of ordinary skill in the art, in view of the guidelines provided herein for beneficially practicing embodiments of the invention. For example, the nanostructure of the present embodiments can be made of an elemental semiconductor of Group IV, and various combinations of two or more elements from any of Groups II, III, IV, V and VI of the periodic table of the elements.

As used herein, the term "Group" is given its usual definition as understood by one of ordinary skill in the art. For instance, Group III elements include B, Al, Ga, In and Tl; Group IV elements include C, Si, Ge, Sn and Pb; Group V elements include N, P, As, Sb and Bi; and Group VI elements include O, S, Se, Te and Po.

In some embodiments of the present invention the nanostructure is made of a semiconductor material that is doped with donor atoms, known as "dopant". The present embodiments contemplate doping to effect both n-type (an excess of electrons than what completes a lattice structure lattice structure) and p-type (a deficit of electrons than what completes a lattice structure) doping. The extra electrons in the n-type material or the holes (deficit of electrons) left in the p-type material serve as negative and positive charge carriers, respectively. Donor atoms suitable as p-type dopants and as n-type dopants are known in the art.

For example, the nanostructure can be made from silicon doped with, e.g., B (typically, but not necessarily Diborane), Ga or Al, to provide a p-type semiconductor nanostructure, or with P (typically, but not necessarily Phosphine), As or Sb or to provide an n-type semiconductor nanostructure.

In experiments performed by the present inventors, Si nanowires and p-type Si nanowires with a Diborane dopant have been utilized.

In some embodiments, the sensing compartment comprises a plurality of nanowires and/or nanotubes, grown on a substrate by using, for example, chemical vapor deposition. Optionally, once the nanowires and/or nanotubes are obtained, the substrate is etched (e.g., by photolithography) and the nanowires and/or nanotubes are arranged within the sensing compartment as desired. Alternatively, nanowires can be made using laser assisted catalytic growth (LCG). Any method for forming a semiconductor nanostructure and of constructing an array of a plurality of nanostructures as described herein is contemplated.

In some embodiments, the sensing compartment comprises a plurality of nanostructures, e.g., from 2 to 2000 nanostructures per 1 square centimeter. The nanostructures can comprise nanowires, as described herein, nanotubes, as described herein, and combination thereof.

Exemplary nanotubes and methods of preparing same are disclosed in WO 2010/052704, which is incorporated by reference as if fully set forth herein.

Any other semiconductor nanostructures, as described in further detail hereinbelow, are also contemplated.

Sensing compartment 12 optionally and preferably comprises a functional moiety 16 covalently attached to nanostructure 14. Functional moiety 16 is selected such that upon contacting with a detectable, target species (e.g., moiety or compound) 18 nanostructure 14 exhibits a detectable change in an electrical property of nanostructure 14.

For example, nanostructure 14 can exhibit a change in density of electrons or holes over some region of nanostructure 14 or over the entire length of nanostructure 14. Nanostructure 14 can additionally or alternatively exhibit a change in its conductivity or resistivity.

When a plurality of nanostructures 14 is employed, all the nanostructures can be covalently attached to the same functional moiety, or, alternatively, at least two nanostructures are covalently attached to different functional moieties. Use of two or more functional moieties on respective two or more nanostructures is advantageous since it allows compartment 12 to sense more than one type of target molecule, sequentially or simultaneously. Functional moieties suitable for some of the present embodiments are provided hereinbelow.

In some of any of the embodiments of sensing compartment 12 as described herein, when a plurality of nanostructures 14 is employed, the nanostructures are included in the same sensing compartment and are in fluid communication thereamongst at all times.

In some of any of the embodiments of sensing system 10 as described herein, a plurality of nanostructures 14 is employed, and the nanostructures are included in two or more sensing compartments and, in each sensing compartment the plurality of nanostructures are in fluid communication thereamongst at all times. Embodiments in which system 10 comprises more than one sensing compartment are described below.

The change in the property of nanostructure 14 can be detected by a detector 32 which communicates with nanostructure 14 via a communication line 34. When a plurality of nanostructures is employed, each of the nanostructures preferably communicates with detector 32 over a separate communication channel.

Detector 32 can be of any type that allows detection of semiconductor property.

For example, detector 32 can be constructed for measuring an electrical measure corresponding to a change in the electrical property. The electrical measure can be, e.g., voltage, current, conductivity, resistance, impedance, inductance, charge, etc.

The detector typically includes a power source and a voltmeter or amperemeter. In one embodiment, a conductance less than 1 nS can be detected. In some embodiments, a conductance in the range of thousands of nS can be detected.

For example, when detectable species 18 effect a change in electron or hole density of nanostructure 14, detector 32 can be configured to apply voltage nanostructure 14 and to measure the current through nanostructure 14. In some embodiments of the present invention nanostructure 14 is in contact with a source electrode and a drain electrode (not shown, see FIG. 10). In these embodiments, detector 32 is optionally and preferably configured to apply a source-drain voltage between the source electrode and the drain electrode and to measure changes in the source-drain current. In some embodiments of the present invention nano structure 14 is in contact with a source electrode, a drain electrode and a gate electrode, such that nanostructure 14 forms a transistor, such as, but not limited to, a field effect transistor (FET). In these embodiments, detector 32 is optionally and preferably configured to apply a source-drain voltage between the source electrode and the drain electrode and optionally also a gate voltage to the gate electrode, and to measure changes in the source-drain current.

Figure 10:
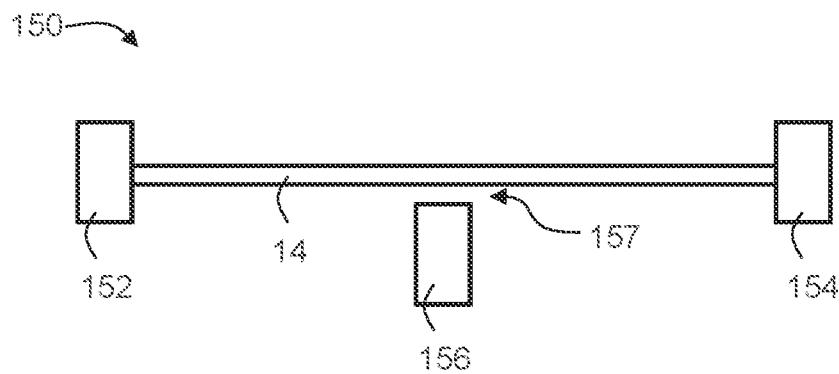
FIG. 10 is a schematic illustration of a nanostructure in embodiment of the invention in which the nanostructure forms a transistor.

FIG. 10 is a schematic illustration of nanostructure 14 in embodiment in which nanostructure 14 forms a transistor 150 (e.g., FET). Transistor 50 comprises a source electrode 152, a drain electrode 154, a gate electrode 156 wherein nanostructure 14 serves as a channel. The gate electrode is optionally and preferably, but not necessarily, is spaced apart from nanostructure 14 by a gap 157. A gate voltage can be applied to channel nanostructure 14 through gate electrode 156. In some embodiments, when the voltage of gate electrode 156 is zero, nanostructure 14 does not contain any free charge carriers and is essentially an insulator. As the gate voltage is increased, the electric field caused thereby attracts electrons (or more generally, charge carriers) from source electrode 152 and drain electrode 154, and nano structure 14 becomes conducting. In some embodiments, no gate voltage is applied and the change in the charge carrier density is effected solely by virtue of the interaction between nanostructure 14 and target molecule 18.

It is appreciated that when the electrical property of the nanostructure varies in response to interaction with a sample that contains the nitro-containing compound, a detectable signal can be produced. For example, a change in the electrical property of the channel induces a change in the characteristic response of the transistor to the gate voltage (e.g., the source-drain current as a function of the gate voltage), which change can be detected and analyzed.

It was also found by the present inventors that a gate voltage that is applied to the gate electrode can be used for reversing the redox transformation exhibited by the functional moiety on the surface of the nanostructure. It was also found by the present inventors that gate voltage can be used to control the amount of moieties that can be oxidized on the surface of the nanostructure. Thus, in some embodiments of the present invention the gate voltage that is applied to the gate electrode is selected to maintain a generally constant, and optionally and preferably predetermined, population of the functional moiety on the surface of the nanostructure. Preferably the gate voltage is constant. Once the nanostructure is contacted with an oxidizing agent (e.g., ROS, $H_2O_2$) the equilibrium condition achieved by the gate voltage is changed, since the presence of the oxidizing agent reduces the population level of the functional moiety. This reduction changes the electrical property (e.g., conductivity) of the nanostructure.

Transistor 150 can be used in more than one way. In some embodiments of the present invention transistor 150 is contained with compartment 12 of system 10, in some embodiments of the present invention transistor 150 is contained in a skin-attachable sticker for use as a skin-attachable metabolic activity device (for example, for continuous glucose monitoring), and in some embodiments of the present invention transistor 150 is implantable in a living body for use, as an implantable metabolic activity device.

Nanostructures 14 can be deposited onto, or be partially or fully submerged in a substrate 28.

The substrate can be, for example, an elastomeric polymer substrate. Suitable elastomeric polymer substrate materials are generally selected based upon their compatibility with the manufacturing process (soft lithography, stereo lithography and three-dimensional jet printing, etc.) and the conditions present in the particular operation to be performed by the microfluidic system. Such conditions can include extremes of pH, pressure within the microchannels, temperature, ionic concentration, and the like. Additionally, elastomeric polymer substrate materials are also selected for their inertness to critical components of an analysis or synthesis to be carried out by the system. Elastomeric polymer substrate materials can also be coated with suitable materials, as discussed in detail below.

In some embodiments, the elastomeric polymer substrate material is preferably transparent. These embodiments are particularly useful when system 10 is used with, or includes, an optical or visual detection device. Alternatively, transparent windows of, e.g., glass or quartz, may be incorporated into the system for this type of detection. The elastomeric polymer can have linear or branched backbones, and can be cross linked or non-cross linked.

Given the tremendous diversity of polymer chemistries, precursors, synthetic methods, reaction conditions, and potential additives, there is a large number of possible elastomeric systems that are contemplated for fabricating the microfluidic system of the present embodiments.

Representative examples of elastomeric polymers include, without limitation, polydimethylsiloxane (PDMS), polyisoprene, polybutadiene, polychloroprene, polyisobutylene, poly(styrene-butadiene-styrene), polyurethanes and silicones. Since the stroke of the piezoelectric actuator is small (nanometer range), the present Inventors also contemplate the use of polymers which are generally non-elastomeric, provided that the wall of the formed microchannel is sufficiently elastic, as further detailed hereinabove. Representative examples of such polymers include, without limitation, PMMA and polycarbonate.

The Sample Compartment:

System 10 can also comprise one or more chambers 20 in controllable fluid communication with sensing compartment 12, via a channel 22 and a valve 24 mounted thereon. When a plurality of chambers is employed, each chamber is optionally in controllable fluid communication with the same sensing compartment 12 via a respective channel 22 and a respective valve 24 mounted thereon. In some embodiments of the present invention, two or more sensing compartments such as sensing compartment 12 are employed, wherein at least two chambers are in controllable fluid communication with different sensing compartments. In some embodiments of the present invention, there is no fluid communication between sensing compartments that are fed by different chambers, and in some embodiments of the present invention there is fluid communication between sensing compartment that are fed by different chambers. Representative examples of embodiments in which the system comprises two or more sensing compartments are provided hereinafter.

In some of any of the embodiments described herein throughout for a sample compartment, when two or more chambers are included, two or more chambers can be in fluid communication thereamongst (in addition to being in fluid communication with the sensing compartment).

The term "chamber" as used herein refers to a close or open enclosure configured to contain a fluid (e.g., a sample solution, a reagent solution). Chamber 20 can be positioned above the surface of the microchannels (e.g., substrate 28 as described herein) or within the surface of the microchannels (e.g., substrate 28 as described herein). If a plurality of chambers is employed, each chamber can independently adopt any of the configurations described herein.

A chamber containing a sample solution is interchangeably referred to herein as a sample chamber, and chamber containing a reagent is interchangeable referred to herein as a reagent chamber.

In some embodiments, each of chambers 20 described herein is independently configured to contain an amount of fluid in a range of from microliters to milliliters.

In some embodiments, the chamber is in a form of a well.

Channel 22 is preferably a microchannel.

The term "microchannel" as used herein refers to a fluid channel having cross-sectional dimensions the largest of which being less than 1 mm, more preferably less than 500 µm, more preferably less than 400 µm, more preferably less than 300 µm, more preferably less than 200 µm, e.g., 100 µm or smaller.

Compartment 12, microchannels 22 and chamber 20 can all be formed in a substrate, which can be the same substrate the supports nanostructures 14 (substrate 28) or it can be a different substrate, as desired.

Typically, but not necessarily, microchannels 22 engage the same plane. For example, compartment 12, microchannels 22 and chamber 20 can all be formed in the substrate such that microchannels 22 engage the same plane over the substrate.

In some embodiments a main channel 26 is connected directly to chamber 12 and each of microchannels 22 is deployed between the respective chamber 20 and main channel 26, such that, for at least one of chambers 20, the fluid path the chamber to compartment 12 includes both the respective microchannel 22 and the main channel 26. Optionally, but not necessarily, main channel 26 is also a microchannel. In some embodiments of the present invention main channel 26 has a diameter which is at least 1 mm. Main channel 26 may engage the same plane with microchannels 22, but in some embodiments a portion of main channel 26 is above or below the plane engaged by microchannels 22.

In some embodiments of the present invention system 10 comprises an additional chamber 21 which is in fluid communication with sensing comportment 12 and also with two or more of chambers 20 such that the fluid path from chambers 20 to comportment 12 pass through additional chamber 21. This embodiment is schematically illustrated in FIG. 9B. Additional chamber 21 can serve, for example, as a reaction or mixing chamber, to which an influx of substances from two or more different chambers 20 can be established. The different substances can react or mix in additional chamber 21 and the mixture and/or reaction products can flow into sensing compartment 12. Communication between additional chamber 21 and sensing compartment 12 can be, for example, via channel 26.

Chamber(s) 20 and channel(s) 22 form together a portion of the system that is also referred to herein interchangeably as "culture compartment" or "sample compartment".

Microchannels 22 can be formed in substrate 28 by any technique known in the art, including, without limitation, soft lithography, hot embossing, stereolithography, three-dimensional jet printing, dry etching and injection molding.

In some embodiments of the present invention the sensing compartment, the microchannels and the chambers are formed on the same substrate, and in some embodiments of the present invention the sensing compartment is formed on a different substrate than the microchannels and the chambers. When different substrates are used, the different substrates can be connected or be separated in a manner than maintains the controllable fluid communication between the chambers and the sensing compartment. For example, controllable fluid communication between the two separate substrates can ensured by embodying main channel 26 as a flexible tube extending from the microchannels 22 to the sensing compartment 12. When sensing compartment and the chambers are formed on the same substrate, they can be arranged in any geometrical relation over the substrate. For example, in some embodiments of the present invention the sensing compartment is positioned at a region of the substrate which is separated from all the chambers, and in some embodiments of the present invention the sensing compartment can be central while the chambers are distributed to at least partially surround the sensing compartment.

System 10 preferably comprises a controller 30 configured for selectively operating each of valves 24 to control flow of fluids from chamber(s) 20 to compartment 12. For clarity of presentation, only one communication line is shown in FIGS. 9A-B between controller 30 and one of valves 24. It is to be understood however, that in at least some embodiments there is a separate communication line between controller 30 and each of valves 24 so as to allow controller 30 to control each valve individually, and optionally independently.

Controller 30 can include, or be associated with a data processor (not shown), which can be a general purpose computer or dedicated circuitry. Controller 30 preferably operates valves 24 automatically according to a predetermined sensing protocol which can be stored in the memory of the data processor. For example, controller can open two valves to allow two fluids to flow into main channel 26, where the fluids can mix and optionally react. Controller 30 can close the valves after predetermined amounts of fluids have passed to channel 26. Alternatively, the valves can remain in their open state to allow continuous sensing. From channel 26 the mixture and optionally the products of the reaction can flow into compartment 12. The mixture or reaction product includes at least target molecule 18. In compartment 12, target molecule 18 contacts nanostructures 14 and functional moiety 16, to effect a change in the property of nanostructure 14. The change in property can be detected by a detector 32.

Once the detection is completed, controller 30 can close the valves (if they remain open) to cease the feeding of target molecule 18 into compartment 12. Thereafter, controller can open another valve to allow flow of washing fluid from one of the chambers 20. The washing fluid is optionally and preferably selected to restore the property of nanostructure 14 to the state or level prior to the contact with molecule 18.

In some embodiments of the present invention compartment 12 comprises an outlet port 36 from which fluids can exit compartment 12 (for example, following a washing operation). An outlet channel 38 can be connected to port 36 to facilitate the removal of fluids from compartment 12. The fluids can flow through port 36 into channel 38 by virtue of an overpressure generated in compartment 12 during the flow of fluids into compartment 12 from channel 26. The fluids can alternatively or additionally flow through port 36 into channel 38 by applying an under pressure (e.g., using a pump, not shown) in channel 38 as known in the art.

According to some embodiments of a sensing system, a sample compartment as described herein is utilized in combination with one or more, sensing systems, whereby one or more sensing systems are as described herein for a sensing system that comprises nanostructures, and/or one or more sensing systems is any other sensing system.

Figure 8:
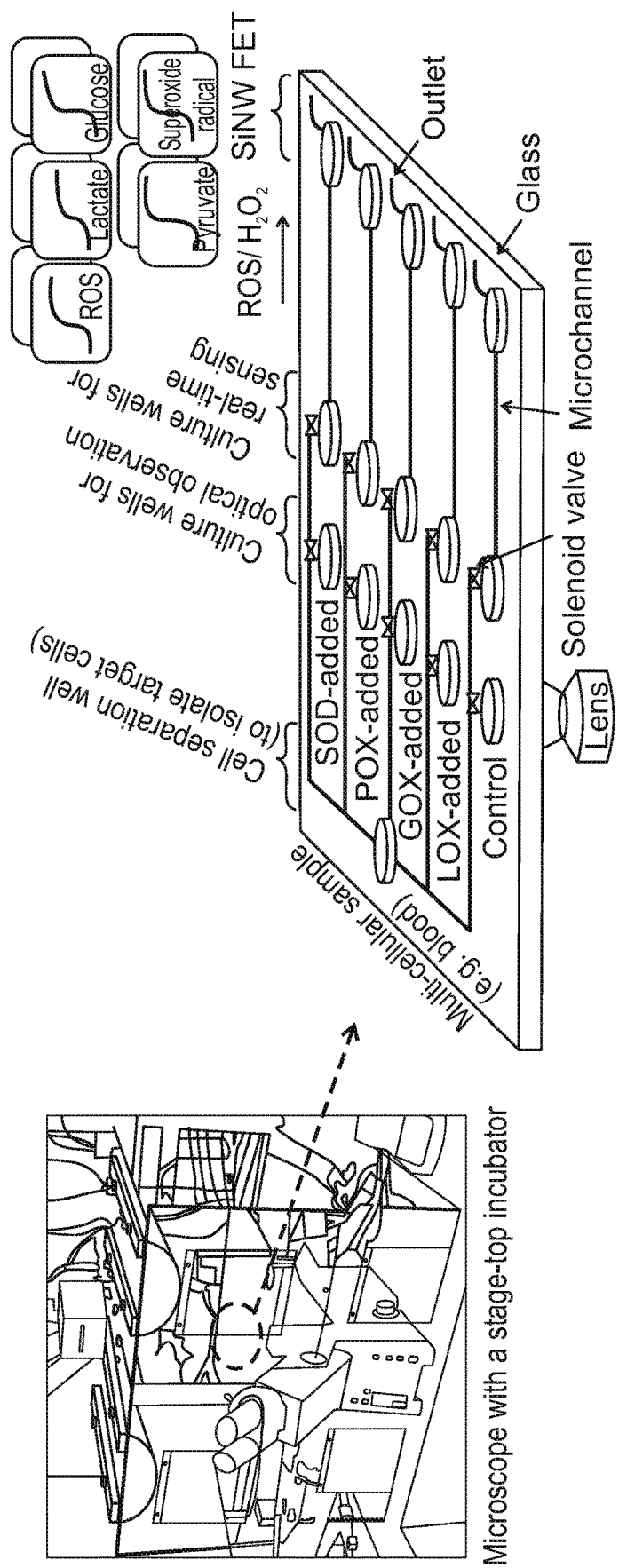
FIG. 8 present schematic representation of an exemplary multiplex real-time monitoring of metabolites using an all-inclusive lab-on-a-chip on an incubator-equipped microscope. The lab-on-a-chip isolates target cells from multicellular samples, and the isolated target cells are dispensed to midstream cell culture wells. Metabolites are then reacted to produce ROS, and solutions are transported to downstream sensing wells (LOX: lactate oxidase; GOX: glucose oxidase; PDX: pyruvate oxidase; SOD: superoxide dismutase; Pi: inorganic phosphate).

In any of the embodiments described herein, system 10 can comprise one or more chambers having at least one transparent wall, base or cover that allow optical inspection. Such chambers can be any of chambers 20 or they can be dedicated chambers. Representative examples of chambers dedicated for optical inspection are illustrated in FIG. 8 and the ordinarily skilled person, provided with the information described herein, would know how to incorporate such dedicated chambers in other embodiments (e.g., the embodiments illustrated in FIGS. 1A, 9A, 9B, 11A, 11B and 11C).

According an aspect of some embodiments of the present invention, there is provided a sensing system, comprising a sensing compartment configured for detecting a target molecule, and a sample compartment as described herein.

In some embodiments, the sample compartment comprises a plurality of chambers, each being in controllable fluid communication with the same sensing compartment via a respective channel (e.g., microchannel) and a respective valve mounted thereon.

In some of these embodiments, the system further comprises a controller, for selectively operating each valve to control flow of fluids from the chambers to the sensing compartment.

Such a system allows performing multiplex monitoring by introducing a plurality of samples to the system, as described in further detail hereinbelow.

The microchannels, chambers, valve, substrate and any other features of a sample compartment can be according to any one of the embodiments described herein for a sample compartment, and to any combination thereof.

The sensing compartment can comprise any structure or plurality of structures which generate a detectable change upon contacting a target molecule, and can be designed accordingly, based on methods known in the art.

In some embodiments, the sensing compartment comprises a semiconductor nanostructure configured such that upon contacting a target molecule, the nanostructure exhibits a detectable change in an electrical property thereof, as described herein. The nanostructure can be functionalized, by generating or attaching to its surface a functional moiety or can be non-functionalized.

The sensing system of the present embodiments can be used in many applications, including without limitation, chemical applications, genetic applications, biochemical applications, pharmaceutical applications, biomedical applications, medical applications, radiological applications and environmental applications.

The sensing can thus be selected such that a detectable change occurs once the target molecule contacts the sensing compartment.

For medical applications, the sensing system of the present embodiments is suitable for diagnostic and patient management, as is described and exemplified hereinafter. For environmental applications the sensing system of the present embodiments is suitable for detecting hazardous materials or conditions such as air or water pollutants, chemical agents, biological organisms or radiological conditions. For genetic and biochemical applications the sensing system of the present embodiments is suitable for testing and/or analysis of DNA, and other macro or smaller molecules, or reactions between such molecules in an approach known as "lab-on-chip."

The sensing system of the present embodiments can also be used in the area of biochemical and biophysical investigations of single cells. For example, the sensing system can isolate a cell or a group of cells of a certain type.

The system and method of the present embodiments can be used for sensing presence of target molecules in many types of fluid media and objects present in fluid media. The objects can comprise organic, inorganic, biological, polymeric or any other material. For example, the fluid medium can comprise blood product, either whole blood or blood component, in which case the objects can be erythrocytes, leukocytes, platelets and the like. The fluid medium can also comprise other body fluids, including, without limitation, saliva, cerebral spinal fluid, urine and the like. Also contemplated are various buffers and solutions, such as, but not limited to, nucleic acid solutions, protein solutions, peptide solutions, antibody solutions and the like. Also contemplated are various biological and chemical reagents such as, but not limited to, oxidizing agents, reducing agents, enzymes, receptor ligands, extracellular components, metabolites, fatty acids, steroids, and the like.

Objects in the fluid medium can comprise other materials, such as, but not limited to, cells, bacteria, cell organelles, platelets, macromolecules, vesicles, microbeads, covered with antibodies specific to soluble factors such as ligands, shaded receptors and biological materials containing a fatty tissue or a microorganism. The objects which are manipulated by the system and method of the present embodiments can also be made of or comprise synthetic (polymeric or non-polymeric) material, such as latex, silicon polyamide and the like. The object can be optically visible or transparent. The objects can also emit light or be conjugated to other objects to facilitate their detection.

Figure 11A:
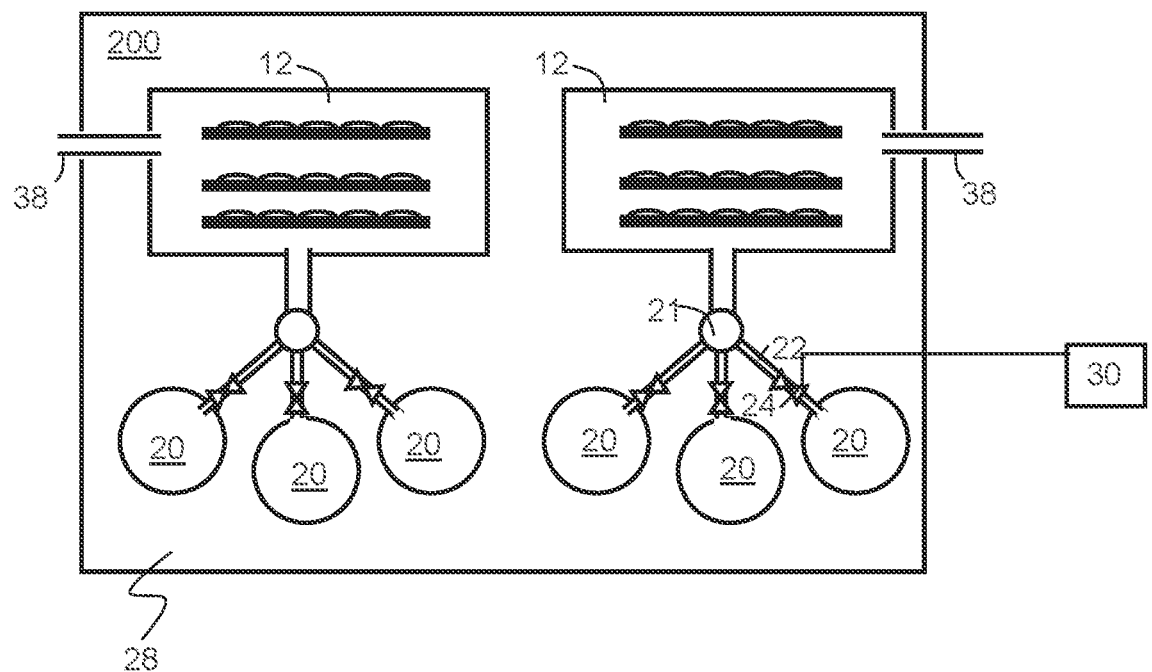
FIGS. 11A-C are schematic illustrations of a system which comprises two or more sensing compartments, according to some embodiments of the present invention.
Figure 11B:
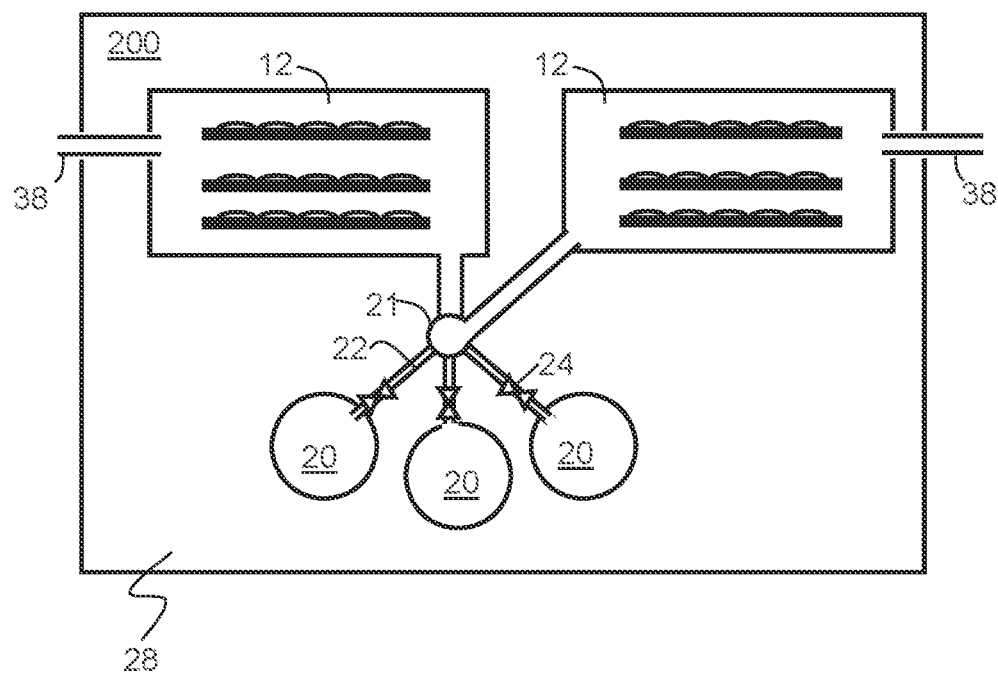
Figure 11C:
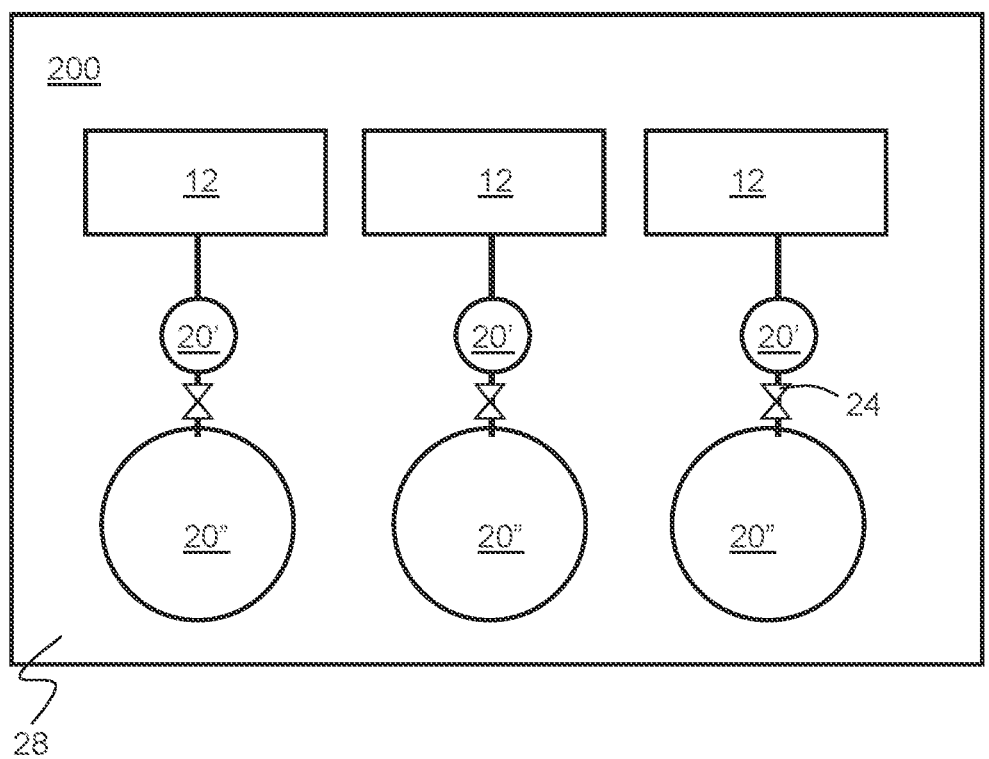
Figure 12:
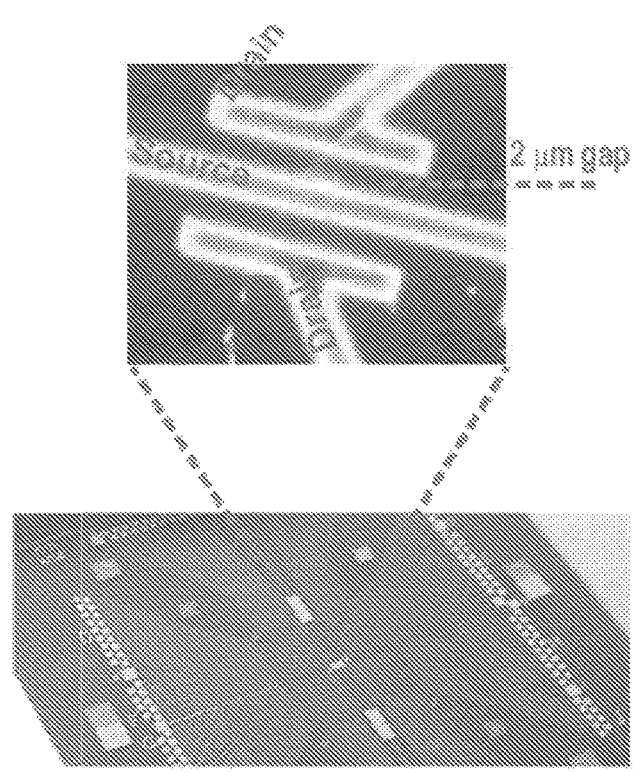
FIG. 12 is a dark field microscope image of an electrically controlled sensor device, according to some embodiments of the present invention.

A Sensing System with Two or More Sensing Compartments:

FIGS. 11A-C are schematic illustrations of a system 200 which comprises two or more sensing compartments 12, according to some embodiments of the present invention. In some embodiments of the present invention the sensing compartments are formed on different regions of the same substrate, and in some embodiments of the present invention the sensing compartments are formed on different substrates.

The structure and principles of the chambers, channels and sensing compartments of system 200 are similar to those of the chambers, channels and sensing compartment of system 10. Features that are optional in system 10 are also optional in system 200. For clarity of presentation, some reference numerals that appear in FIGS. 9A-B have been omitted from FIGS. 11A and 11B.

The advantage of having more than one sensing comportments is that several sensing assays can be executed by the same system, either simultaneously or sequentially. In some exemplary embodiments of the invention the nanostructures in each of the sensing compartments are designed to sense different types of target molecules, and in some exemplary embodiments of the present invention the nanostructures in two or more of the sensing compartments are designed to sense the same target molecule but which may optionally be indicative of different substances or activities and/or which is derived from different samples.

The signals from each compartment can be analyzed separately, for example, to separately determine presence, absence or level of different target molecules therein. The signals from two or more compartments (e.g., all the compartments) can be also analyzed collectively, such that the collection of signals from the respective sensing compartments defines a signature of the target molecule or target molecules.

In the illustration of FIG. 11A, each sensing compartment 12 is fed from a plurality of chambers 20, as further detailed hereinabove with respect to system 10. Thus, for example, in these embodiments several systems such as system 10 can be formed on the same substrate to form system 200.

In the illustration of FIG. 11B, fluid communication can be established (by controlling the respective valve 24) from at least one chambers to two or more sensing compartments 12. These embodiments allow performing different sensing assays to the same substance.

FIG. 11C illustrates a configuration in which each sensing compartments 12 is fed by a different chamber 20. The chamber that feeds a respective sensing compartment 12 can itself be fed by another chamber. The chambers that directly feed sensing compartments 12 are designated 20' and the chambers that directly feed chambers 20' are designated 20". Chambers 20" can hold for example, the sample to be analyzed and chambers 20' can hold fluids selected to provide conditions under which the target molecule is generated or produced. For example, chambers 20' can contain a biological and/or a chemical reagent. When the respective valve is open, the sample flow from chamber 20" to chamber 20', so that the condition for producing the target molecule is met, and the target molecule flows to the respective sensing compartment 12.

A more specific example, which is not intended to be limiting, is illustrated in FIG. 8, which show schematic representation of an exemplary multiplex real-time monitoring of metabolites using an all-inclusive lab-on-a-chip on an incubator-equipped microscope. The lab-on-a-chip isolates target cells from multi-cellular samples, and the isolated target cells are dispensed to midstream cell culture wells. Metabolites are then reacted to produce ROS, and solutions are transported to downstream sensing wells (LOX: lactate oxidase; GOX: glucose oxidase; PDX: pyruvate oxidase; SOD: superoxide dismutase; Pi: inorganic phosphate).

A Sensing System for Detecting Redox Reactive Agents:

A sensing system as described herein was exemplified while using SiNW (silicon nanowires) FET array within one or more sensing compartment(s), whereby at least some of the silicon nanowires were modified by introducing to the surface thereof a functional group which is being such that upon contacting a sample that contains an oxidizer or a reductant, the plurality of nanowires exhibit a detectable change in an electrical property, which is indicative of the presence and/or amount of a reductant-producing or oxidizer-producing substance, such as, for example, a metabolite. The functional group can be, for example, a group that is capable of undergoing redox reactions, preferably reversibly, and which, as a result of oxidation or reduction, the electron density on the nanowire changes.

Figure 1B:
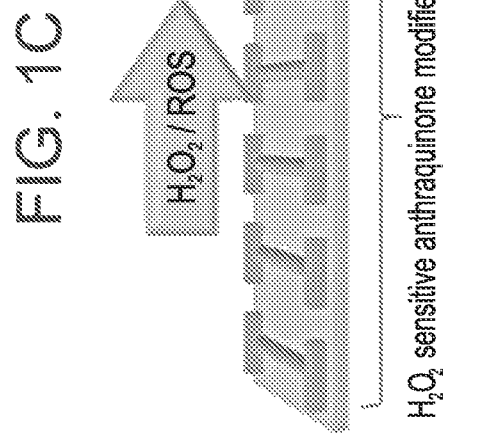
Figure 1C:
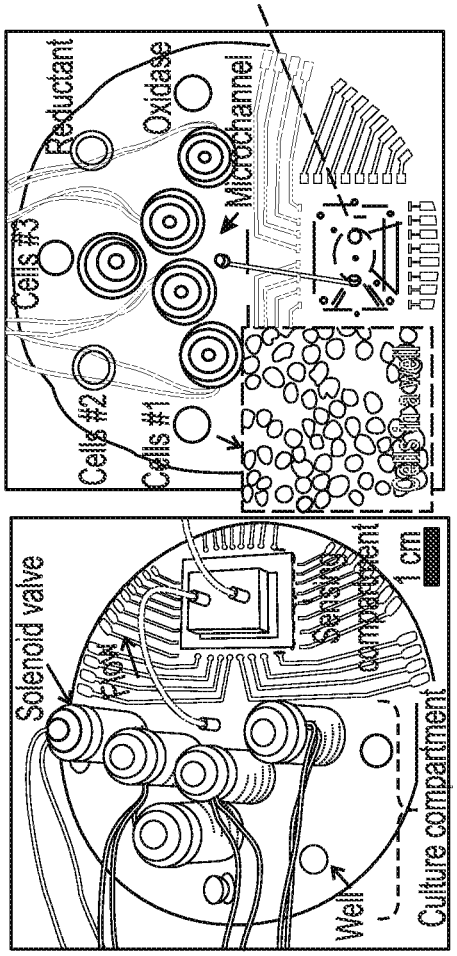

More specifically, a system as described herein was exemplified by reacting amino-functionalized silicon nanowires with 9,10-anthraquinone-2-sulfochloride to thereby produce 9,10-dihydroxyanthracene-modified SiNW (see, FIG. 1C). In an exemplary assay, the system was operated by converting small-molecule hydrogen-producing metabolites to peroxide ($H_2O_2$) by means of microfluidic mixing with oxidase enzymes, within the culture compartment, and before the metabolite-containing solution reach the FET array in the sensing compartment. The resulting solution is then introducing to the FET array and the produced peroxide oxidizes 9,10-dihydroxyanthracene on a FET surface to form 9,10-anthraquinone. This oxidation reaction decreases surface electron density to increase a current flowing through the p-type SiNW FET. In another assay, a reductant, such as, for example, DEHA, solution is introduced to the sensing compartment and reduces 9,10-anthraquinone to 9,10-dihydroxyanthracene to increase surface electron density. Thus, surface electron density is varied by oxidation or by reduction and changes the measured current.

A system comprising 9,10-dihydroxyanthracene-modified field-effect transistor (FET) sensor array as described herein was successfully constructed and characterized (see, for example, FIGS. 1A, 1B, and 2A-2D) and was shown to successfully perform in sensing of peroxide (see, FIGS. 3A-B), of peroxide-producing metabolites (see, FIGS. 4A-C), and in pH sensing (see, FIGS. 5A-C), in physiological solutions and/or culture medium without preprocessing, and while performing concentration-dependent sensing over the whole physiological concentration ranges. An exemplary system as described herein was also shown to perform sensing of cells while monitoring metabolic activities and consequent proliferation rates (see, FIGS. 6A-I). Metabolic significances of human chronic lymphocytic leukemia were also validated (see, FIGS. 7A-B and Table 1).

An exemplary system, according to some embodiments of the present invention, integrating a redox-reactive nanowire sensing compartment and a microfluidic network, was demonstrated to successfully perform multiplex real-time monitoring of metabolic activity of cells, in physiological solutions and optionally without preprocessing. Monitoring the metabolic activity by the exemplary system was also successfully utilized for validating cancer metabolism and pharmaceutical mechanisms of anticancer agents.

The results, as presented in the Examples section that follows, clearly indicate that a biosensing methodology as described herein can be successfully utilized in monitoring and/or analyzing various metabolic activities, by, for example, detecting various ROS-producing metabolites. Such a system can be successfully utilized per se or as a part of an all-inclusive lab-on-a-chip, as described herein and is presented, for example, in FIG. 8, in various diagnostic and therapeutic applications, ranging, for example, from isolating target cells to sensing, to facilitating high throughput screening (HTS), and to detecting metabolic changes during a treatment to monitor therapy effectiveness and facilitating personalized treatment.

According to an aspect of some embodiments of the sensing system as described herein, there is provided a system which can be utilized for detecting an oxidizing agent or a reducing agent or a substance producing an oxidizing agent or a reducing agent, and which generates a detectable change once such an agent is introduced to or generated in the system.

A sensing system according to this aspect comprises at least one chamber being in controllable fluid communication with a sensing compartment.

According to some embodiments, the chamber is configured to contain a fluid and is as described herein and illustrated in FIGS. 9A-B.

According to some embodiments, the sensing system is as described herein and illustrated independently in FIGS. 9A-B, FIG. 1A or FIG. 1B.

According to some of any of the embodiments described herein, the sensing compartment comprises a semiconductor nanostructure, as described herein with reference to FIGS. 9A-B.

According to some of any of the embodiments relating to a system according to this aspect of the present invention, sensing is performed by means of a functional moiety which is attached to the nanostructure, and which is selected such that upon contacting a redox reactive species, the nanostructure exhibits a detectable change in an electrical property.

As used herein and in the art, the phrase "redox reactive species" describes a moiety or a compound that can participate in a redox reaction or reduction-oxidation reactions, either as an oxidizer or a reductant, and is capable of altering an oxidation number of one or more atoms of another substance. This phrase is used herein throughout to describe both an oxidizer and a reductant.

Herein throughout, for any one of the embodiments described herein for any of the aspects of the present invention, an "oxidizer", which is also referred to herein interchangeably as "an oxidizing/oxidative agent" or "an oxidizing/oxidative moiety" or "an oxidizing/oxidative species" describes a moiety, species or a compound that is capable of elevating the oxidation number of one or more atoms of another substance. Typically, such an alteration involves transformation of protons from the other substance to the oxidizing moiety or compound.

Exemplary oxidizing agents that are suitable for being detected using a sensing system as described herein include, but are not limited to, reactive oxygen species (ROS) or compounds generated by reactive oxygen species.

As used herein throughout, and is well known in the art, reactive oxygen species include oxygen-containing molecules and/or ions in which an oxygen atom is in a free radical form (having an unpaired electron) or molecules or ions that readily generate species featuring one or oxygen free radical or oxygen in singlet state. Examples include, without limitations: ozone, peroxides, RO—, and ROO—, in which R is an organic moiety or hydrogen. In the presence of water or any other protic solvent, ROS typically generate hydrogen peroxide. Hydrogen peroxide or any other peroxide is therefore an exemplary oxidizing agent according to some embodiments of the present invention.

Herein throughout, for any one of the embodiments described herein for any of the aspects of the present invention, a "reductant", which is also referred to herein interchangeably as "a reducing/reductive agent" or "a reducing/reductive moiety" or "a reducing/reductive species"

describes a moiety, species or a compound that is capable of reducing the oxidation number of another substance. Typically, such an alteration involves transformation of protons from the reducing agent to the other substance.

Suitable reducing agents include, for example, moieties or species that upon release of one or more protons form a stable anion. Exemplary such agents include, for example, hydroxyl-containing agents that form a stable enolate anion upon releasing one or more protons. Compounds or moiety containing an amine-oxide group are given herein as an example. N-alkyl- or N,N-dialkyl-hydroxyl amines (e.g., DMHA) are given as a representative example. Any other known reducing agents are also contemplated.

According to some embodiments of the present invention, the functional moiety is a redox-reactive moiety, which upon contacting the redox reactive agent, a change in the oxidation number of one or more of its atoms occurs.

Preferably, the functional moiety is such that can easily be transformed from a reduced state to oxidized state, and vice versa, namely, features a change in the oxidation number of its atom(s) at a low energy barrier. The functional moiety can be regarded as such that can feature a reversible change in an oxidation number of one or more of its atoms, namely, a reversible redox change or transformation. A reversible redox change of a moiety or group can be determined, for example, by cyclic voltametry measurements.

Exemplary functional moieties are such that feature a redox potential that ranges from about −1.0 to about 1.0 Volt, or from −0.8 to 0.8 Volt, or from −0.6 to 0.6 Volt or from −0.5 to 0.5 Volt, or from −0.4 to 0.4 Volt, or from −0.3 to 0.3 Volt or from −0.2 to 0.2 Volt, or from −0.1 to 0.1 Volt, as well as lower potentials and any value therebetween.

A functional moiety can comprises at least one functional group that is capable of undergoing a reversible redox change, as described herein.

In some of any of the embodiments described herein for a functional moiety, a length of the functional moiety is smaller than 2 nm, smaller than 1.5 nm, and even smaller than 1 nm. This allows the formation of the charge transfer complex to occur close to the nanostructures' surface, thereby enhancing the device's sensitivity.

In some of any of the embodiments described herein, the functional moiety is selected such that a Debye length of at least 100 nm, at least 500 nm, at least 800 nm and even 1 micron and higher is exhibited.

As used herein and in the art, the phrase "Debye length" describes the distance over which significant charge separation can occur.

An exemplary functional moiety comprises at least one functional group that is capable of undergoing a keto-enol tautomerization, as this term is well known in the art.

Moieties comprising one or more functional groups capable of undergoing keto-enol tautomerization include, for example, a quinone moiety and can be collectively represented by the following scheme 1:

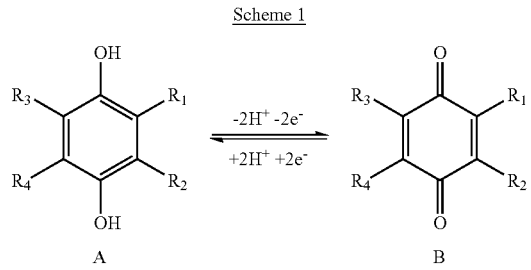

wherein $R_1$-$R_4$ are each independently selected from the group consisting of hydrogen, alkyl, aryl, cycloalkyl, halo, trihaloalkyl, alkoxy, carboxy and any other chemically compatible substituent, as described herein, or, alternatively, $R_1$ and $R_2$ and/or $R_3$ and $R_4$ form together a carbocyclic ring, which can be substituted or unsubstituted.

A carbocyclic ring encompasses 5-membered or 6-membered aromatic or alicyclic ring. Heterocyclic and heteroatomatic rings, as defined herein, are also contemplated.

Preferably, one or both of $R_1$ and $R_2$ and $R_3$ and $R_4$ form together an aromatic ring (including heteroaromatic ring), which can be substituted or unsubstituted. Such moieties are referred to herein as aromatic quinones, and include, for example, benzoquinone, anthraquinone, phenanthrenequinone, each being substituted or unsubstituted, as described herein.

In Scheme 1 above, the moiety on the left (A) represents a moiety featuring atoms in a reduced state (reduced oxidation number) and the moiety on the right (B) represents a moiety featuring atoms in elevated oxidation number, and transformation between the two states is effected by proton transfer and is referred to herein as redox change or redox transformation.

For detecting an oxidizing agent, the moiety A on the left in scheme 1 is to be used for generating a functional moiety on the nanostructure surface. Such a moiety, in the presence of an oxidizing agent undergoes electron delocalization and proton loss, and generates the moiety B on the right in scheme 1.

For detecting a reducing agent, the moiety on the right is to be used.

Additional exemplary functional groups that can be included in a redox reactive functional moiety as described herein include, but are not limited to, NADH and analogs thereof, as depicted in Schemes 2-4 below; FADH$_2$ and analogs thereof, as depicted in Scheme 5, ferrocene and analogs, derivatives and metal complexes thereof, as depicted in Scheme 6, porphyrinogenic organometallic complexes, ferrocyanide and analogs thereof.

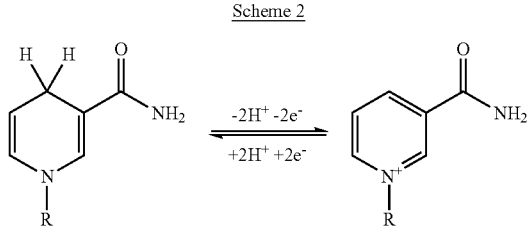

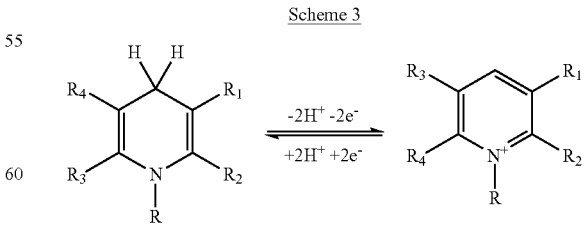

wherein R and $R_1$-$R_4$ are each independently selected from the group consisting of hydrogen, alkyl, aryl, cycloalkyl, halo, trihaloalkyl, alkoxy, carboxy and any other chemically compatible substituent, as described herein, or, alternatively, $R_1$ and $R_2$ and/or $R_3$ and $R_4$ form together a carbocylic ring, which can be substituted or unsubstituted, as defined herein.

An exemplary such functional moiety is depicted in Scheme 4 below.

Scheme 4

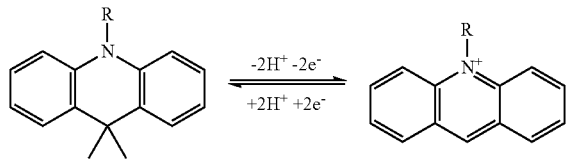

Scheme 5

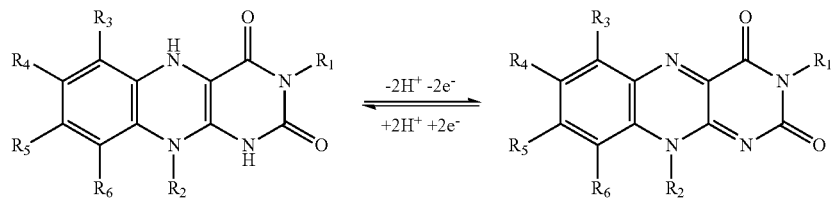

wherein $R_1$-$R_6$ are each independently selected from the group consisting of hydrogen, alkyl, aryl, cycloalkyl, halo, trihaloalkyl, alkoxy, carboxy and any other chemically compatible substituent, as described herein, or, alternatively, two or more of $R_2$-$R_6$ form together a carbocylic ring, which can be substituted or unsubstituted, as defined herein.

Scheme 6

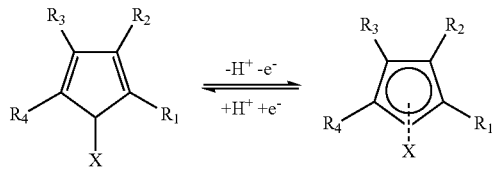

wherein $R_1$-$R_4$ are each independently selected from the group consisting of hydrogen, alkyl, aryl, cycloalkyl, halo, trihaloalkyl, alkoxy, carboxy and any other chemically compatible substituent, as described herein, or, alternatively, two or more of $R_1$-$R_4$ form together a carbocylic ring, which can be substituted or unsubstituted, as defined herein; and X is hydrogen or, preferably a metal atom or ion, optionally further substituted by additional, one or more, ferrocene moiety or moieties, which can be the same or different. It is to be noted that if more than one ferrocene moiety are present, the redox reaction involves electron transfer that corresponds to the number of ferrocene moieties.

Exemplary, non-limiting porphyrinogenic organometallic complexes include, porphyrin, tetramethylpyridilporphyrin [5, 10, 15, 20-tetrakis(1-methyl-4-pyridinio)-porphine] [TMPyP]; tetrahydroxyphenylporphyrine [5, 10, 15, 20-tetrakis(4-hydroxyphenyl)-21H, 23H-porphine] [TP(OH)P]; tetraphenylporphyrin [5, 10, 15, 20-tetraphenyl-21H, 23H-porphine] [TPP]; 4, 4', 4'', 4'''-(porphine-5, 10, 15, 20-tetrayl) tetrakis(benzenesulfonic acid) [TBSP]; hematoporphyrin; protoporphyrin IX, chlorophylle, heme and corrin, complexed with a transition metal such as, for example, cobalt [Co], nickel [Ni], iron [Fe], zinc [Zn], and copper [Cu]. Other metals are and porphyrinogenic ligands and any combination thereof are also contemplated.

According to some of any of the embodiments described herein for a sensing system for detecting redox reactive moieties, the redox reactive moiety is an oxidizer and the functional moiety is in its reduced state, such that upon contacting an oxidizer, it is oxidized and as result and generates a change in electrical property of the nanostructure.

In some embodiments, when the functional moiety is oxidized by an oxidizer, the electron density on the nanostructure surface is reduced. When the functional moiety is reduced, electron density on the nanostructure surface is increased.

Figure 1D:
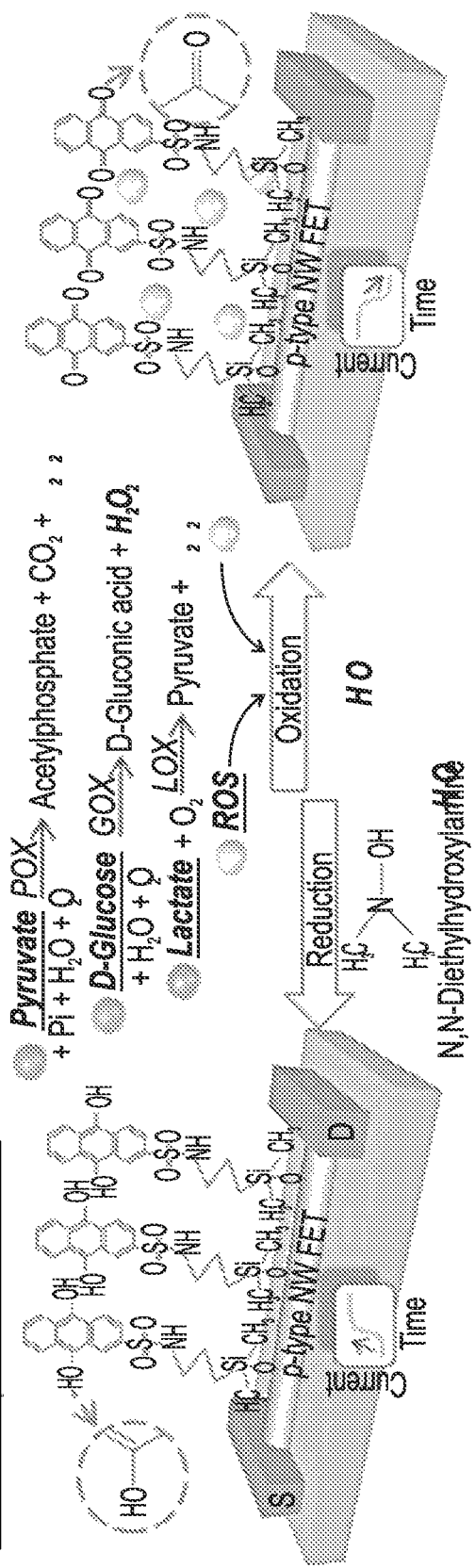

Reference is made in this regard to FIG. 1D and to the description in Example 1, which are to be taken as describing an exemplary, non-limiting embodiment, exemplifying an embodiment for a mode of operation of a sensing system as described in this aspect.

In some of any of the embodiments described herein, the functional moiety is covalently attached to the nanostructure's surface by means of covalent bonds formed between reactive groups within the functional moiety and compatible reactive groups on the surface of the nanostructures, directly or via a linker.

Reactive groups on the nanostructure's surface are either intrinsic or can be generated upon a suitable treatment. In some embodiments, where the nanostructure is SiNW or silicon nanotubes, free hydroxyl groups are intrinsically present on the surface of the nanostructures and can be utilized for attaching functional moieties thereto.

Alternatively, the nanostructures described herein are first surface-modified so as to generate surface reactive groups. Such a surface modification can be performed by, for example, attaching to intrinsic functional groups on the nanostructure surface a bifunctional linker molecule, which comprises in one terminus thereof a reactive group that is capable of forming a bond with these intrinsic functional groups and in another terminus thereof a reactive group that can form a bond with the functional moiety as described herein or with a reactive group therein.

In some of any of the embodiments described herein, the functional moiety comprises, prior to being attached to the nanostructure, a reactive group that can readily react with a reactive group on the nanostructure surface, as described herein, so as to form a covalent bond with the nanostructure surface.

Selecting reactive groups that are compatible with functional groups on the nanostructure of choice is within the capabilities of any person skilled in the art, particularly in view of the guidance provided herein.

In some embodiments, when the nanostructure is SiNW or silicon nanotubes, the functional moiety comprises a reactive group capable of forming covalent bond with free hydroxy groups on the nanostructure surface. Exemplary such reactive groups include, but are not limited to, halides and alkoxides, which can act as leaving groups so as to form an ether bond, carboxylic acids or esters, which can form an ester bond via esterification or trans esterification, as well as halosilanes and orthosilicates, which can form —Si—O— bonds.

According to some embodiments of the invention, the functional moiety is attached to the nanostructure via any one of the bonds described herein.

In some embodiments, the functional moiety is attached to the nanostructure via a bifunctional linker, as described herein.

An exemplary such a linker is derived from an orthosilicate that comprises 1, 2 or 3 —OR groups attached to Si, for forming —Si—O—Si bonds with intrinsic hydroxyl groups on the silicon nanostructure surface, and 1, 2 or 3 hydrocarbon groups (e.g, alkyl, alkylene, cycloalkyl, aryl) terminating with a reactive group that is capable of reacting with a reactive group of the functional moiety as described herein, such that the total number of groups attached to the Si atom is 4.

In exemplary embodiments, the linker is an orthosilicate comprising an aminoalkyl, one or more alkyl groups and one or more alkoxy groups attached to the Si atom. In one example, the linker is derived from (3-aminoalkyl)-orthosilicatedimethyl-ethoxysilane (APDMES). Such linkers generate a reactive amine group on the surface of the nanostructure. Similar orthosilicate terminating with other reactive groups, such as, for example, described herein, are also contemplated.

As discussed hereinabove, the functional moiety can be attached to the nanostructure by means of a reactive group that is compatible with a reactive group on the nanostructure surface. A functional moiety as described herein is derived from a compound featuring a redox reactivity as described herein, which further comprises a reactive group as described herein, directly or indirectly (e.g., via a linker) attached thereto.

For compounds as presented in Schemes 1, 3, 5 and 6 herein, the reactive group can be, or form a part of (as a substituent), any one or $R_1$-$R_4$ or $R_1$-$R_6$ or, a substituent on the carbocylic ring(s) formed by $R_1$ and $R_2$ and/or $R_3$ and $R_4$, or $R_1$-$R_4$, or $R_2$-$R_6$ as described herein.

For porphyrinogenic complexes, the reactive group can be a substituent of the porphyrin-type ligand.

In an exemplary embodiment, the functional moiety is attached to the nanostructure via a sulfonamide bond, formed from a sulfonate reactive group and an amine reactive group.

In an exemplary embodiment, the functional moiety is a quinone, as described herein, preferably an aromatic quinone, which comprises one or more sulfonate-containing substituents. In an exemplary embodiment, such a functional moiety is attached to modified nanowires exhibiting amine groups by means of a sulfonamide bond.

Functional moieties which are metal-containing complexes, can be covalently attached to the nanostructure, as described hereinabove, or, alternatively or in addition, be absorbed to the nanostructure surface, non-covalently.

Multi-Component Systems:

For any one of the sensing systems as described herein, and any one of the embodiments thereof, the sensing system can comprise a plurality of sensing compartment(s) comprising a nanostructure as described herein, which can be the same or different.

In some of these embodiments, one or more, or each of the plurality of sensing compartments can independently be a sensing compartment for detecting redox reactive agents or species as described herein and according to any one of the embodiments described herein with respect thereto.

For any one of the sensing systems as described herein, and any one of the embodiments thereof, the sensing system can further comprise an additional sensing compartment or device, in addition to the nanostructure-based sensing compartment as described herein, or, for embodiments describing optionally other sensing compartment s, instead of the nanostructure-based sensing compartment.

Exemplary sensing devices or compartment s include, for example, optical sensing devices or compartments.

In some of any one of the embodiments described herein for a sensing system that comprises a semiconductor nanostructure sensing compartment, the system may comprise additional, one or more sensing compartment(s), being devoid of the semiconductor nanostructure and also in fluid communication with one or more of the chambers of the sample compartment, wherein said additional sensing compartment or device is configured to receive signals from this additional compartment.

The Sensing Method:

According to an aspect of some of any of the embodiments described herein, there is provided a method detecting a target molecule.

Any one of the sensing systems as described herein is usable for detecting a target molecule upon introducing a sample containing the target molecule or generating the target molecule to the sample compartment, as described herein.

By "introducing" are encompassed placing, injecting, incubating, flowing (e.g., by means of microchannels), etc., and any combination thereof.

When the sensing system comprises two or more chambers in the sample compartment, two or more samples can be introduced to the sample compartment, each introduced to a different chamber. Sensing can then be effected to both samples simultaneously or sequentially, by controlling the fluid communication between each chamber and the sensing compartment.

Optionally, when sensing is effected sequentially, washing the sensing compartment is effected between sequential sensing.

In some embodiments, the sample compartment further comprises a chamber containing a washing fluid (e.g., washing solution), as described in further detail hereinafter.

As used herein and in the art "detecting" encompasses determining a presence and/or amount of a target molecule.

As used herein, the term "target molecule", which is also referred to herein interchangeably as "target moiety", "target species", a detectable moiety or a detectable species, describes a compound, moiety or species that contacts a sensing compartment and induces a detectable change.

The sensing compartment used in the method is designed such that a detectable change occurs when the target molecule contacts it, as described herein.

In some of the embodiments according to this aspect, determining a presence and/or amount of a target molecule is indicative of a presence and/or amount of a component of the sample that generates or produces the target molecule.

In some of these embodiments, generation or production of the target molecule is effected in situ, namely, upon subjecting the introduced sample to conditions under which the target molecule is generated/produced.

Such conditions include, for example, a reagent that reacts with the sample or with components thereof, so as to generate the target molecule, directly or indirectly.

Other conditions include, for example, altering the pH of the sample, by contacting it with a pH-adjusting reagent.

Subjecting the introduced sample to conditions under which the target molecule is generated may be effected, for example, by containing a solution of the reagent in one of the chambers in the sample compartment, and allowing fluid communication between each of the chamber containing the sample and the chamber containing the reagent with the sensing compartment. The fluid communication is preferably effected simultaneously from both chambers, but also be effected sequentially, with a short time interval.

Alternatively, a fluid communication is effected between the two chambers, optionally to an additional chamber, and then a fluid communication to the sensing compartment is effected.

In any one of these embodiments, the chamber which provides conditions for generating the target molecule forms a part of the sensing system.

Further alternatively, the reagent is added to the same chamber to which the sample is introduced, prior to effecting fluid communication between the chamber and the sensing compartment. The reagent and the sample can also be introduced together to the same chamber.

In case two or more samples are analyzed for a detectable moiety, each of the samples can be independently subjected to the conditions as described herein.

In some of any of the embodiments described herein for the sensing method, the sensing system utilized is for sensing redox reactive agents, as described herein.

According to an aspect of any one of the embodiments of a detection method as described herein, there is provided a method of determining a presence and/or amount of a redox reactive agent in one or more fluid sample(s).

In some embodiments of this aspect, the method is effected by introducing the sample(s) to a sensing system as described herein in the context of redox reactive agents.

In some of any one of the embodiments described herein, once the sample is introduced to a chamber in the sample compartment, or once the sample is subjected to conditions in which a redox reactive agent is generated, detection is performed by fluidly communicating the chamber with the sensing compartment.

As discussed hereinabove, the sensing compartment is such that upon contacting the redox reactive agent, a detectable change in an electrical property of the nanostructure(s) forming the sensing compartment is effected, and is indicative of the presence and/or amount of the redox reactive agent in a tested sample.

The method can be performed by introducing one or more samples to the sample compartment and/or by subjecting one or more of these samples to conditions which generate the redox reactive species.

In some of any one of the embodiments described herein, the method is for determining a presence and/or amount of a substance producing an oxidizing agent or a reducing agent in one or more fluid samples, and can further comprise subjecting one or more of the fluid sample(s) to a reaction condition under which the substance produces the redox reactive agent.

In some exemplary embodiments of any one of these embodiments, the reaction conditions under which a substance in the sample produces the redox reactive agent include oxidizing or reducing conditions, and in some exemplary embodiments, the conditions include pH adjustment.

Providing these conditions can be effected by means of, for example, suitable chemical reagents, or biological activators such as, for example, enzymes, receptor ligands, hormones, and the like.

In some of any of these embodiments, the reagent in an enzyme, such as, for example, an oxidase or a reductase, that catalyzes a production of an oxidizing agent or a reducing agent by the substance, respectively.

In some of any of these embodiments, a different reaction condition (e.g., the reagent) is used for different samples, and the method is effected by subjecting, as described herein, each sample to its respective condition, prior to fluidly communicating the sample (upon being subjected to the condition) to a sensing compartment.

In some of any one of the embodiments described herein, the redox reactive agent is an oxidizer, as described herein, for example, ROS or a peroxide produced thereby.

In these embodiments, the functional moiety in the sensing compartment is selected capable of interacting with the oxidizer while effecting a change in an electrical property of the nanostructure, as described herein.

In some of any of the embodiments described herein, the tested sample comprises an oxidizer as described herein (e.g., $H_2O_2$).

In some of any one of the embodiments described herein, the tested sample comprises a substance producing an oxidizer, and the method is for determining a presence and/or amount of this substance in the sample.

In some of any one of the embodiments described herein, the substance is a metabolite which produces an oxidizer under suitable conditions.

Almost any biological metabolite can be subjected to a condition such as, for example, enzymatic reactions or chemical reagents, under which it produces ROS and subsequent $H_2O_2$.

Non-limiting examples, to list a few, include:

Lactate, which produces $H_2O_2$ in a reaction catalyzed by a lactate oxidase;

Glucose, which produces $H_2O_2$ in a reaction catalyzed by a glucose oxidase;

Pyruvate, which produces $H_2O_2$ in the presence of inorganic phosphate and oxygen;

Hypoxanthine, which produces $H_2O_2$ in a reaction catalyzed by xanthine oxidase;

NAD(P)H, which produces a superoxide in a reaction catalyzed by NAD(P)H oxidase;

Superoxide ($O_2^-$), which produces $H_2O_2$ in a reaction catalyzed by superoxide dismutase.

Aldehydes, which produce $H_2O_2$ in reaction catalyzed by a respective aldehyde oxidase.

Choline, which produces $H_2O_2$ in a reaction catalyzed by choline oxidase.

Similarly, some metabolites produce reductants, as described herein, upon being subjected to respective enzymatic reductases, dehydrogenases or reducing chemical environment (e.g., $H_2$-containing environment). Any other conditions under which a metabolite or any other substance (e.g., a biological substance) produces an oxidizer or a reductant are contemplated herein.

In an exemplary general method of detecting a redox reactive moiety or a substance producing a redox reactive moiety, a sample as described herein is introduced to a chamber is the sample compartment, is optionally subjected to one or more conditions, such as, for example, to culture conditions, chemical conditions, therapeutic conditions and/ or conditions for producing a redox reactive moiety, and, then is fluidly communicated with a sensing compartment for detecting a redox reactive agent, according to any one of the embodiments described herein for sensing a redox reactive agent.

In one exemplary embodiment, a solution containing a redox reactive agent, such as, for example, hydrogen peroxide, is introduced to a chamber in the sample compartment and is then fluidly communicated with a sensing compartment for a redox reactive agent, as described herein. The signal generated by the sensing compartment is indicative for the presence and/or amount of the metabolite.

In one exemplary embodiment, a solution containing a metabolite, optionally a physiological solution (e.g., a physiological medium), is introduced to one chamber in a sample compartment as described herein (e.g., a sample chamber). A solution containing a condition under which the metabolite produced a redox reactive agent is introduced (e.g., a suitable oxidase or chemical reagent) to another chamber in the sample compartment (e.g., a reagent chamber or a condition chamber). The two chambers are fluidly communicated, optionally by being flowed to a third chamber (e.g., a test chamber), and the third chamber is then fluidly communicated with a sensing compartment as described herein. The signal generated by the sensing compartment is indicative for the presence and/or amount of the metabolite.

A reference data of signals generated by this method for various concentrations of various metabolites can be used for processing data acquired from more complex samples, so as to monitor and analyze a metabolic activity of cells, so as to determine, for example, abnormal metabolic activity or an improvement thereof, as is discussed in further detail hereinafter.

Herein throughout, a "condition" encompasses chemical reagents, biological reagents, biological conditions (e.g., culture medium), heating, radiation, therapy (e.g., medicament or any other treatment such as radiation), and the like.

In one exemplary embodiment, a cell is introduced to one chamber in the sample compartment, and subjected to culture conditions. For example, culture medium, which is stored in one chamber in the sample compartment (e.g., a first reagent chamber) is fluidly communicated with the chamber containing the cell (e.g., a sample chamber). Thereafter, cultured cells are subjected, optionally, to viability assay, for determining number of viable cells and/or proliferation rate of the cells. For example, a portion of the cultured cells in the chamber can be fluidly communicated with another chamber, which includes conditions for a viability assay or proliferation assay. Alternatively or in addition, portion of the cultured cells can be subjected to another condition, for example, a therapy or therapeutic agent (e.g., medicament or any other treatment), and be cultured in the presence of the medicament or treatment (e.g., in a first reagent chamber). Further alternatively, cells can first be cultured, and then subjected to a medicament or other treatment by being flowed to a chamber containing the medicament or treatment (e.g., a second reagent chamber). Alternatively, cells can be flowed to another chamber and a solution containing the medicament or treatment can be introduced to a different chamber and be flowed to the same chamber as the cells (e.g., a sample chamber).

Alternatively to a condition of a therapy or therapeutic agent (e.g., a medicament or treatment), or in addition thereto, a cells solution (with and/or without therapy) is subjected to a condition for generated a redox reactive moiety, as described hereinabove. For example, cells subjected to a therapy are flowed (fluidly communicated) to yet another chamber (e.g., test chamber) and a condition solution is flowed (fluidly communicated) to that chamber as well. The chamber is then fluidly communicated with a sensing compartment. Intact cells, not subjected to a therapy are similarly subjected to the condition for producing a redox reactive agent and fluidly communicated with a sensing compartment.

Optionally, each of the cells samples described herein is fluidly communicated to one sensing compartment in a system which comprises a plurality of sensing compartments as described herein (see, for example, FIG. 11C).

Sensing data acquired for each and every of the above described chambers is indicative of a metabolic activity of the cell, optionally upon being subjected to a condition such as a medicament or other treatment.

In some of any one of the embodiments described herein for a method, after a chamber is fluidly communicating with a sensing compartment as described herein, one or more washing solutions, present in one or more chambers of the sample compartment, are fluidly communicated with the sensing compartment. In some of these embodiments, a washing solution is used so as to "normalize" the functional moiety, namely, to change the oxidation state in the functional moiety to its original oxidation sate. For example, a washing solution is used to transfer a functional moiety that has been oxidized by an oxidizing target moiety to a reduced state thereof or transfer a functional moiety that has been reduced by a reductant target moiety to an oxidized state thereof. Alternatively or in addition, a solution containing a pH adjusting agent is used as a washing solution.

Alternatively, in any one of the method steps described herein, pH sensing can also be effected, as exemplified in the Examples section that follows.

The Sample:

The sample introduced to any one of the sensing systems as described herein can be, for example, a solution containing the target moiety or the substance producing the target moiety, as described herein.

Alternatively, the sample is more complex and comprises, for example, cells, a biological sample, a biological sample comprising cells, each of which may further comprise additional agents, reagents, media and the like, as generally described hereinabove.

In some of any one of the embodiments described herein, the sample comprises cells and the method can be used for determining a presence and/or amount of the target moiety (e.g., a redox reactive agent as described herein) or of substance producing the redox reactive agent, in the cells.

When the substance is a metabolite, the method can be used in determining, monitoring and/or analyzing a metabolic activity of the cell.

As used herein "cell" refers to a prokaryotic or a eukaryotic cell for which the above metabolic activity can be measured. The cell can be a bacteria, yeast, plant, insect or mammalian cell. According to a specific embodiment, the cell is a human cell. It will be appreciated that the cell may refer to a single cell but may also refer to a plurality of cells. The cells may be isolated cells (having no tissue organization) or cells in a tissue or tissue fragment. According to a specific embodiment, when the cells are PBMCs, the assay is done on $10^3$-$10^{10}$ cells. According to a specific embodiment the number of cells is $10^6$-$10^7$.

The cell may be a differentiated cell, a non-differentiated cell (e.g., stem cell) or a dedifferentiated cell.

According to one embodiment, the cell is a cell of the immune system, that is a white blood cell (i.e., a leukocyte).

Examples include, a neutrophil, an eosinophil, a basophil, a lymphocyte (T cell or B cell), a monocyte, a macrophage and a dendritic cell.

According to another embodiment, the cell is a pathogenic or diseased cell of any tissue such as a cancer cell. Other diseases and medical conditions which can be detected according to the present teachings are provided below.

Other cells which may be analyzed according to the present teachings include, but are not limited to, en embryonic cell (such as for IVF qualification), a red blood cell, a platelet, a bacterial-infected cell, a fungus-infected cell, and a viral infected cell.

Thus, the cell may refer to an isolated population of cells which comprise a highly purified subset of specific cells i.e., homogenic cell population (e.g. >80% purity), e.g., T cells, or a heterogenic cell population which comprises various types of immune cells such as peripheral blood leukocytes (PBL) or mononuclear cells.

Cells may be non-cultured, cultured primary cells or cloned cells (e.g., cell-line).

The cells may be adherent cells or cells in suspension.

According to further embodiments, the cells can be non-genetically modified or genetically modified.

According to some of any of the embodiments described herein, two or more samples, each comprising a different cell or a different solution of a cell, can be introduced simultaneously to the system (e.g., each sample is introduced to a different chamber in the sample compartment). Optionally, introducing is without pre-processing the sample.

Each of these samples can be subjected to the same or different conditions before sensing is effected, as described herein.

Optionally, the same sample is subjected to different conditions, and sensing is effected upon each subjection.

A sample as described herein can be a cellular biological sample.

Exemplary cellular biological samples include, but are not limited to, blood (e.g., peripheral blood leukocytes, peripheral blood mononuclear cells, whole blood, cord blood), a solid tissue biopsy, cerebrospinal fluid, urine, lymph fluids, and various external secretions of the respiratory, intestinal and genitourinary tracts, synovial fluid, amniotic fluid and chorionic villi.

Biopsies include, but are not limited to, surgical biopsies including incisional or excisional biopsy, fine needle aspirates and the like, complete resections or body fluids. Methods of biopsy retrieval are well known in the art.

Upon being introduced to the system, cells in any one of the samples described herein can be grown within the chamber to which they are introduced, either in physiological medium or in the presence of additional reagents (e.g., a medicament, as described herein).

Applications:

A sensing method as described hereinabove, can be utilized in a variety of diagnostic and therapeutic applications.

In some embodiments, at least one fluid sample which comprises a cell further comprises a therapeutic agent, and the method as described herein is used for determining or monitoring activity of the cell upon contacting the therapeutic agent.

Such a method can be used for determining an efficacy of the therapeutic agent towards the cell.

In some embodiments the substance is a metabolite, and the method is being for monitoring a metabolic activity (MA) of a cell.

According to an aspect of some embodiments of the present invention, there is provided a method of monitoring a metabolic activity of a cell. The method is effected by introducing the cell to any one of the sensing systems as described herein, optionally subjecting the cell to a condition under which a metabolite generates a target moiety, and fluidly communicating the target moiety with a sensing compartment.

In some embodiments of this aspect, a cell can be introduced to the system as described herein, cultured, and then, portions of the cultured cells can be fluidly communicated with different chambers and each can be subjected to a different condition, and each chamber of each condition can then be fluidly communicated with a suitable sensing compartment, as described herein.

In some embodiments of this aspect, one or more of the sensing compartments is a sensing compartment for detecting redox reactive moieties and a cell is subjected to conditions under which a metabolite produces a redox reactive moiety, as described herein.

A method of monitoring a metabolic activity of a cell can be used, for example, for identifying an agent capable of altering a metabolic activity of the cell, wherein cells cultured, for example, in a system as described herein, are subjected to a condition which includes a tested agent, and then metabolic activity is determined as described herein. Cultured cells can be subjected simultaneously to different agents, in different chambers, and each of these chambers can then be subjected to different further conditions for determining amount and/or presence of one or more metabolites, as described herein.

Using as the fluid sample a biological sample as described herein of a subject in any of the embodiments of a method as described herein can be used for diagnosing a disease associated with a modified metabolic activity in the subject.

Alternatively, such a method can be used for monitoring a treatment of a disease associated with a modified metabolic activity in the subject.

In some embodiments, the sensing system comprises at least two chambers for containing a fluid sample, and the method comprises introducing at least two samples to the sensing system, wherein each of the at least two samples is introduced to each of the at least two chambers, and the method is being for simultaneously or sequentially determining a presence and/or an amount of the substance in the at least two fluid samples. In one exemplary embodiment, the two samples include cells, one healthy cells and one diseased cells, and the method allows comparing the change in metabolic activity of a diseased cell. In one exemplary embodiment, the two samples include diseased cells, one subjected to a therapeutic condition (e.g., medicament or treatment) and one subjected to another therapeutic condition or is not subjected to any condition, and the method allows comparing a change in metabolic activity of a diseased cell as a result of the therapeutic condition, and thus is indicative of a therapeutic efficacy of the tested therapeutic agent.

According to an aspect of some embodiments of the present invention there is provided a method of diagnosing a disease associated with a modified metabolic activity in a subject in need thereof. The method is effected by introducing a cellular sample (a biological cellular sample as described herein) of the subject to a sensing system as described herein, and determining a presence and/or amount of one or more metabolites in the sample, as described herein.

The subject may be a healthy animal or a human subject undergoing a routine well-being check up. Alternatively, the subject may be at risk of having a disease associated with a modified metabolic activity such as cancer (e.g., a genetically predisposed subject, a subject with medical and/or family history of cancer, a subject who has been exposed to carcinogens, occupational hazard, environmental hazard) and/or a subject who exhibits suspicious clinical signs of cancer [e.g., blood in the stool or melena, unexplained pain, sweating, unexplained fever, unexplained loss of weight up to anorexia, changes in bowel habits (constipation and/or diarrhea), tenesmus (sense of incomplete defecation, for rectal cancer specifically), anemia and/or general weakness).

As used herein the term "diagnosis" or "diagnosing" refers to determining presence or absence of a pathology (e.g., a disease, disorder, condition or syndrome), classifying a pathology or a symptom, determining a severity of the pathology, monitoring pathology progression, forecasting an outcome of a pathology and/or prospects of recovery and screening of a subject for a specific disease.

As used herein "a disease associated with a modified metabolic activity" refers to a disease that is characterized by a cell population that has undergone a shift in metabolic activity as compared to an identical cell population taken from a normal, healthy (unaffected with the disease). That cell population that has undergone a shift in metabolic activity, can be a pathogenic cell population (i.e., disease-causing cells e.g, cancer cells) or a non-pathogenic cell population (e.g., disease combating cells e.g., immune cells such as in the case of solid-tumor). For instance, in oncology, most cancer cells predominantly and some populations of the immune system undergoing clonal expansion produce energy by a high rate of glycolysis followed by lactic acid production in the cytosol, rather than by a comparatively low rate of glycolysis followed by oxidation of pyruvate in mitochondria like most normal cells.

According to some embodiments, the level (presence and/or amount) of one or more metabolite(s) in a normal, healthy (unaffected) sample of identical cell composition are determined under identical conditions which were used to monitor the cells of the subject.

A shift (i.e., a change) in the metabolic activity (a level of one or more metabolites) between the cells of the subject and those of the control (normal, unaffected), as evidenced from the metabolites level(s) obtained under identical conditions, is indicative of a disease associated with the modified metabolic activity profiles.

Thus, for example, data acquired by a method as described herein for level (amount) of metabolites like lactate, optionally combined with data for level of glucose and/or pyruvate, can be compared with data presenting levels of one or more of these metabolites in normal cells, so as to determine is a subject has cancer. Moreover, such data can be compared with other data for more accurately determine a type of cancer and/or its origin and/or its stage, based on the level of one or more of these metabolites in the biological cellular sample.

The results of the metabolic activity assay may be subject to decision tree models which classify the results and assist in final diagnosis. According to a preferred embodiment, at least two models are combined (see FIGS. 9A-B & 10). Examples of such models include, but are not limited to, CHAID, CS and C&R Tree. The Logistic model may be further applied.

Examples of medical conditions which can be diagnosed and treated (as is further described hereinbelow) according to the present teachings include, but are not limited to, cancer, pathogenic infection and autoimmune diseases. Specific examples are provided in the following.

Inflammatory diseases include, but are not limited to, chronic inflammatory diseases and acute inflammatory diseases.

Inflammatory diseases associated with hypersensitivity diseases associated with hypersensitivity such as, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH. Included are the following, as non-limiting examples:

Type I or immediate hypersensitivity, such as asthma;

Type II hypersensitivity such as, but are not limited to, rheumatoid diseases, rheumatoid autoimmune diseases, rheumatoid arthritis, spondylitis, ankylosing spondylitis, systemic diseases, systemic autoimmune diseases, systemic lupus erythematosus, sclerosis, systemic sclerosis, glandular diseases, glandular autoimmune diseases, pancreatic autoimmune diseases, diabetes, Type I diabetes, thyroid diseases, autoimmune thyroid diseases, Graves' disease, thyroiditis, spontaneous autoimmune thyroiditis, Hashimoto's thyroiditis, myxedema, idiopathic myxedema; autoimmune reproductive diseases, ovarian diseases, ovarian autoimmunity, autoimmune anti-sperm infertility, repeated fetal loss, neurodegenerative diseases, neurological diseases, neurological autoimmune diseases, multiple sclerosis, Alzheimer's disease, myasthenia gravis, motor neuropathies, Guillain-Barre syndrome, neuropathies and autoimmune neuropathies, myasthenic diseases, Lambert-Eaton myasthenic syndrome, paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies; neuropathies, dysimmune neuropathies; neuromyotonia, acquired neuromyotonia, arthrogryposis multiplex congenita, cardiovascular diseases, cardiovascular autoimmune diseases, atherosclerosis, myocardial infarction, thrombosis, granulomatosis, Wegener's granulomatosis, arteritis, Takayasu's arteritis and Kawasaki syndrome; anti-factor VIII autoimmune disease; vasculitises, necrotizing small vessel vasculitises, microscopic polyangiitis, Churg and Strauss syndrome, glomerulonephritis, pauci-immune focal necrotizing glomerulonephritis, crescentic glomerulonephritis; antiphospholipid syndrome; heart failure, agonist-like β-adrenoceptor antibodies in heart failure, thrombocytopenic purpura; hemolytic anemia, autoimmune hemolytic anemia, gastrointestinal diseases, autoimmune diseases of the gastrointestinal tract, intestinal diseases, chronic inflammatory intestinal disease, celiac disease, autoimmune diseases of the musculature, myositis, autoimmune myositis, Sjogren's syndrome; smooth muscle autoimmune disease, hepatic diseases, hepatic autoimmune diseases, autoimmune hepatitis and primary biliary cirrhosis.

Type IV or T cell mediated hypersensitivity, include, but are not limited to, rheumatoid diseases, rheumatoid arthritis, systemic diseases, systemic autoimmune diseases, systemic lupus erythematosus, glandular diseases, glandular autoimmune diseases, pancreatic diseases, pancreatic autoimmune diseases, Type 1 diabetes; thyroid diseases, autoimmune thyroid diseases, Graves' disease; ovarian diseases, prostatitis, autoimmune prostatitis, polyglandular syndrome, autoimmune polyglandular syndrome, Type I autoimmune polyglandular syndrome, neurological diseases, autoimmune neurological diseases, multiple sclerosis, neuritis, optic neuritis, myasthenia gravis, stiff-man syndrome, cardiovascular diseases, cardiac autoimmunity in Chagas' disease, autoimmune thrombocytopenic purpura, anti-helper T lymphocyte autoimmunity, hemolytic anemia, hepatic diseases, hepatic autoimmune diseases, hepatitis, chronic active hepatitis, biliary cirrhosis, primary biliary cirrhosis, nephric diseases, nephric autoimmune diseases, nephritis, interstitial nephritis, connective tissue diseases, ear diseases, autoimmune connective tissue diseases, autoimmune ear disease, disease of the inner ear, skin diseases, cutaneous diseases, dermal diseases, bullous skin diseases, pemphigus vulgaris, bullous pemphigoid and pemphigus foliaceus.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

Autoimmune diseases such as, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis, myocardial infarction, thrombosis, Wegener's granulomatosis, Takayasu's arteritis, Kawasaki syndrome, anti-factor VIII autoimmune disease, necrotizing small vessel vasculitis, microscopic polyangiitis, Churg and Strauss syndrome, pauci-immune focal necrotizing and crescentic glomerulonephritis, antiphospholipid syndrome, antibody-induced heart failure, thrombocytopenic purpura, autoimmune hemolytic anemia, cardiac autoimmunity in Chagas' disease and anti-helper T lymphocyte autoimmunity.

Examples of autoimmune rheumatoid diseases include, but are not limited to rheumatoid arthritis and ankylosing spondylitis.

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. diseases include, but are not limited to autoimmune diseases of the pancreas, Type 1 diabetes, autoimmune thyroid diseases, Graves' disease, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome.

Examples of autoimmune gastrointestinal diseases include, but are not limited to, chronic inflammatory intestinal diseases, celiac disease, colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis, primary biliary cirrhosis and autoimmune hepatitis.

Examples of autoimmune neurological diseases include, but are not limited to, multiple sclerosis, Alzheimer's disease, myasthenia gravis, neuropathies, motor neuropathies; Guillain-Barre syndrome and autoimmune neuropathies, myasthenia, Lambert-Eaton myasthenic syndrome; paraneoplastic neurological diseases, cerebellar atrophy, paraneoplastic cerebellar atrophy and stiff-man syndrome; non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies; dysimmune neuropathies; acquired neuromyotonia, arthrogryposis multiplex congenita, neuritis, optic neuritis and neurodegenerative diseases.

Examples of autoimmune muscular diseases include, but are not limited to, myositis, autoimmune myositis and primary Sjogren's syndrome and smooth muscle autoimmune disease.

Examples of autoimmune nephric diseases include, but are not limited to, nephritis and autoimmune interstitial nephritis.

Examples of autoimmune diseases related to reproduction include, but are not limited to, repeated fetal loss.

Examples of autoimmune connective tissue diseases include, but are not limited to, ear diseases, autoimmune ear diseases and autoimmune diseases of the inner ear.

Examples of autoimmune systemic diseases include, but are not limited to, systemic lupus erythematosus and systemic sclerosis.

Infectious diseases such as, but are not limited to, chronic infectious diseases, subacute infectious diseases, acute infectious diseases, viral diseases, bacterial diseases, protozoan diseases, parasitic diseases, fungal diseases, mycoplasma diseases and prion diseases.

Graft rejection diseases including diseases associated with transplantation of a graft such as, but are not limited to, graft rejection, chronic graft rejection, subacute graft rejection, hyperacute graft rejection, acute graft rejection and graft versus host disease.

Allergic diseases which include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

According to a specific embodiment the disease is cancer.

Cancerous diseases include but are not limited to carcinoma, lymphoma, blastoma, sarcoma, and leukemia. Particular examples of cancerous diseases but are not limited to: Myeloid leukemia such as Chronic myelogenous leukemia. Acute myelogenous leukemia with maturation. Acute promyelocytic leukemia, Acute nonlymphocytic leukemia with increased basophils, Acute monocytic leukemia. Acute myelomonocytic leukemia with eosinophilia; Malignant lymphoma, such as Birkitt's Non-Hodgkin's; Lymphoctyic leukemia, such as Acute lumphoblastic leukemia. Chronic lymphocytic leukemia; Myeloproliferative diseases, such as Solid tumors Benign Meningioma, Mixed tumors of salivary gland, Colonic adenomas; Adenocarcinomas, such as Small cell lung cancer, Kidney, Uterus, Prostate, Bladder, Ovary, Colon, Sarcomas, Liposarcoma, myxoid, Synovial sarcoma, Rhabdomyosarcoma (alveolar), Extraskeletel myxoid chonodrosarcoma, Ewing's tumor; other include Testicular and ovarian dysgerminoma, Retinoblastoma, Wilms' tumor, Neuroblastoma, Malignant melanoma, Mesothelioma, breast, skin, pancreas, cervix, prostate, and ovarian.

Thus, the present teachings can be used in disease detection. Following is a non-limiting embodiment which relates to early cancer detection.

Disease diagnosis made according to the present teachings is followed by substantiation of the screen results using gold standard methods. Once diagnosis is established either relying on the present teachings or substantiated using Gold standard methods, the subject is informed of the diagnosis and treated as needed.

Thus, according to an aspect of some embodiments of the invention there is provided a method of disease treatment in a subject in need thereof, the method comprising:

(a) diagnosing a presence of the disease in the subject according to the method described above; and (b) treating the subject based on the diagnosis.

Embodiments of the present invention have a variety of applications pertaining to individually optimizing disease treatment, monitoring disease treatment in a subject, determining a treatment for a subject and identifying an agent capable of treating a disease associated with abnormal metabolic activity.

According to an aspect of some embodiments of the invention there is provided a method of individually optimizing disease treatment, the method comprising:

determining a presence and/or amount of a metabolite in a biological sample of the subject which comprises a cell with at least one medicament, using any one of the relevant methods as described herein, including any embodiments thereof, whereas a shift in the metabolic activity (as measured by the level of one or more metabolites, as described herein, of the cell towards that of a normal healthy cell sample examined under identical conditions is indicative of an efficacious medicament for the disease.

As used herein "individually optimizing treatment" refers to an ex vivo method of tailoring treatment regimen (e.g., type of medicament, dose).

As used herein a "medicament" describes a formulation of a medicine, medicinal drug or medication, as interchangeably used herein. Examples of medicaments, include but are not limited to, chemotherapy, antibiotics, antiparasitic drugs, antiviral and the like.

As used herein throughout, for any of the relevant embodiments described herein, a "therapy" describes a therapeutic agent, which is also referred to herein as a medicament, as well as other treatments such as, for example, radiation, dehydration, devitalization, and the like.

As used herein throughout, cells of a biological sample are contacted with a medicament or any other treatment within a sample compartment of a sensing system, as described herein. Herein throughout, the term "contacting" refers to bringing the medicament into the vicinity of a cell under conditions such that the medicament contacts the cell membrane and if needed internalizes thereto. Thus, for example, the contacting should be effected under buffer conditions, at a temperature and time sufficient to allow the medicament to affect cell phenotype (e.g., cytotoxic or cytostatic effect). The contacting may be effected in vitro, ex vivo or in vivo.

According to a specific embodiment, "a shift in the metabolic activity of the cell towards that of a normal healthy cell sample examined under identical conditions" refers to at least a 10% local or global (throughout the profile) shift preferably towards 100% identity to the control normal healthy cell sample.

A shift beyond a predetermined threshold as will be determined by the skilled artisan is indicative of an efficacious treatment.

According to an aspect of some embodiments of the present invention there is provided a method of monitoring disease treatment in a subject, the method comprising:

(a) administering at least one medicament against the disease to the subject;

(b) retrieving a biological sample which comprises a cell of the subject following the administering;

(c) introducing the biological sample to a sensing system according to any one of the embodiments described herein; and determining a level of one or more metabolites in the sample, wherein a level of at least one metabolite, and preferably of several metabolites, is indicative of the metabolic activity of the cell and whereas a shift in the metabolic activity of the cells towards that of a normal healthy cell sample examined under identical conditions is indicative of an efficacious treatment of the disease.

Likewise, there is provided a method of identifying an agent capable of altering a metabolic activity of cells, the method comprising:

(a) subjecting cells to an agent;

(b) measuring the metabolic activity of the cells prior to and subsequent to subjection to the agent, wherein a shift in a level of one or more metabolites is indicative of an agent capable of altering a metabolic activity of cells.

As used herein, the term "agent" refers to a test composition comprising a biological agent or a chemical agent.

Examples of biological agents that may be tested as potential modulators of metabolic activity according to the method of the present invention include, but are not limited to, nucleic acids, e.g., polynucleotides, ribozymes, siRNA and antisense molecules (including without limitation RNA, DNA, RNA/DNA hybrids, peptide nucleic acids, and polynucleotide analogs having altered backbone structures or other chemical modifications); proteins, polypeptides (e.g. peptides), carbohydrates, lipids and "small molecule" drug candidates. "Small molecules" can be, for example, naturally occurring compounds (e.g., compounds derived from plant extracts, microbial broths, and the like) or synthetic organic or organometallic compounds having molecular weights of less than about 10,000 daltons, preferably less than about 5,000 daltons, and most preferably less than about 1,500 daltons.

According to a preferred embodiment of this aspect of the present invention the agents are anti-cancer, anti-viral or antibiotic agents.

It will be appreciated that the shift, as used herein, can be also a different level (e.g., higher level) of MA in same profile; a change in basal state, and/or a shift in the agent concentration that induces maximal MA effect.

Once an agent capable of altering a metabolic activity of cells has been identified in accordance with the above teachings, the invention further comprises formulating the agent into a pharmaceutical composition/medicament.

A method as described in this aspect can be used for screening for lead candidates for therapeutically active agents of a disease; for screening for therapeutically active agent for treating a disease in a particular subject; and the like.

According to some embodiments, a method of monitoring disease treatment in a subject, is effected by:

(a) administering at least one medicament against the disease to the subject;

(b) retrieving a biological sample which comprises a cell of the subject following said administering;
(c) monitoring a presence and/or amount of a metabolite that produces an oxidizing agent or a reducing agent in an extracellular environment of said cell, using any of sensing methods and system as described in any one of the embodiments described herein, wherein a change a presence and/or amount of the metabolite is indicative of the metabolic activity of the cell and whereas a shift in the metabolic activity of the cells towards that of a normal healthy cell sample examined under identical conditions is indicative of an efficacious treatment of the disease.

In some embodiments, any of the systems and methods as described herein further includes means for separating target cells from a biological sample, as described herein. Such means include, for example, introducing the sample to a chamber in the sample compartment and fluidly communicating the sample with markers, factors, activators, inhibitors or any other biological substance suitable for isolating target cells. The target cells can then be fluidly communicated with, for example, culture medium and/or subjected to sensing in the presence or absence of a condition, as described herein. Exemplary target cells are cancerous cells.

Such a methodology is also described herein as a lab-on-chip.

In any of the applications described herein, substances other than metabolites, which produce a detectable moiety, can be used for diagnosing, treating and/or monitoring treatment as described herein, by determining a presence and/or amount of the substance in biological samples as described herein.

In some of any of the embodiments described herein for an application of a method as described herein, a sensing system for detecting redox reactive agent, as described herein, is utilized, optionally in combination with one or more other sensing systems or sensing compartments, as described herein.

It is expected that during the life of a patent maturing from this application many relevant nanostructures, functional moieties and methods of producing same will be developed and the scope of these terms is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the term "amine" describes both a —NR'R" group and a —NR'— group, wherein R' and R" are each independently hydrogen, alkyl, cycloalkyl, aryl, as these terms are defined hereinbelow.

The amine group can therefore be a primary amine, where both R' and R" are hydrogen, a secondary amine, where R' is hydrogen and R" is alkyl, cycloalkyl or aryl, or a tertiary amine, where each of R' and R" is independently alkyl, cycloalkyl or aryl.

Alternatively, R' and R" can each independently be hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, C-carboxylate, O-carboxylate, N-thiocarbamate, O-thiocarbamate, urea, thiourea, N-carbamate, O-carbamate, C-amide, N-amide, guanyl, guanidine and hydrazine.

The term "amine" is used herein to describe a —NR'R" group in cases where the amine is an end group, as defined hereinunder, and is used herein to describe a —NR'— group in cases where the amine is a linking group.

Herein throughout, the phrase "end group" describes a group (a substituent) that is attached to another moiety in the compound via one atom thereof.

The phrase "linking group" describes a group (a substituent) that is attached to two or more moieties in the compound via two or more atoms thereof.

For example, when am amine group is generated in a surface of a nanostructure it is an end group, and upon being covalently attached to a functional moiety, it is a linking group.

The term "alkyl" describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 6 or 1 to 4 carbon atoms. The alkyl group may be substituted or unsubstituted, as described herein.

The alkyl group can be an end group, as this phrase is defined hereinabove, wherein it is attached to a single adjacent atom, or a linking group, as this phrase is defined hereinabove, which connects two or more moieties via at least two carbons in its chain.

The term "aminoalkyl" is used herein to describe an alkyl substituted by an amine, as defined herein. In some embodiments, the amine substitutes a terminal carbon atom in the alkyl.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted, as described herein. The cycloalkyl group can be an end group, as this phrase is defined hereinabove, wherein it is attached to a single adjacent atom, or a linking group, as this phrase is defined hereinabove, connecting two or more moieties at two or more positions thereof.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted, as described herein. The aryl group can be an end group, as this term is defined hereinabove, wherein it is attached to a single adjacent atom, or a linking group, as this term is defined hereinabove, connecting two or more moieties at two or more positions thereof. Examples include phenyl, naphthalene, anthracene, and the like.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted, as described herein. The heteroaryl group can be an end group, as this phrase is defined hereinabove, where it is attached to a single adjacent atom, or a linking group, as this phrase is defined hereinabove, connecting two or more moieties at two or more positions thereof. Representative examples are pyridine, pyrrole, oxazole, indole, purine and the like.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted, as described herein. The heteroalicyclic group can be an end group, as this phrase is defined hereinabove, where it is attached to a single adjacent atom, or a linking group, as this phrase is defined hereinabove, connecting two or more moieties at two or more positions thereof. Representative examples are piperidine, piperazine, tetrahydrofurane, tetrahydropyrane, morpholino and the like.

The term "amine-oxide" describes a —N(OR')(R") or a —N(OR')— group, where R' and R" are as defined herein. This term refers to a —N(OR')(R") group in cases where the amine-oxide is an end group, as this phrase is defined hereinabove, and to a —N(OR')— group in cases where the amine-oxide is an end group, as this phrase is defined hereinabove.

Whenever a group, moiety or compound as described herein is substituted, the substituent can be, for example, one or more of hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine, as defined herein.

The term "halide" and "halo" describes fluorine, chlorine, bromine or iodine.

The term "haloalkyl" describes an alkyl group as defined above, further substituted by one or more halide.

The term "sulfate" describes a —O—S(=O)$_2$—OR' end group, as this term is defined hereinabove, or an —O—S(=O)$_2$—O— linking group, as these phrases are defined hereinabove, where R' is as defined hereinabove.

The term "thiosulfate" describes a —O—S(=S)(=O)—OR' end group or a —O—S(=S)(=O)—O— linking group, as these phrases are defined hereinabove, where R' is as defined hereinabove.

The term "sulfite" describes an —O—S(=O)—O—R' end group or a —O—S(=O)—O— group linking group, as these phrases are defined hereinabove, where R' is as defined hereinabove.

The term "thiosulfite" describes a —O—S(=S)—O—R' end group or an —O—S(=S)—O— group linking group, as these phrases are defined hereinabove, where R' is as defined hereinabove.

The term "sulfinate" describes a —S(=O)—OR' end group or an —S(=O)—O— group linking group, as these phrases are defined hereinabove, where R' is as defined hereinabove.

The term "sulfoxide" or "sulfinyl" describes a —S(=O)R' end group or an —S(=O)— linking group, as these phrases are defined hereinabove, where R' is as defined hereinabove.

The term "sulfonate" describes a —S(=O)$_2$—R' end group or an —S(=O)$_2$— linking group, as these phrases are defined hereinabove, where R' is as defined herein.

The term "S-sulfonamide" describes a —S(=O)$_2$—NR'R" end group or a —S(=O)$_2$—NR'— linking group, as these phrases are defined hereinabove, with R' and R" as defined herein.

The term "N-sulfonamide" describes an R'S(=O)$_2$—NR"— end group or a —S(=O)$_2$—NR'— linking group, as these phrases are defined hereinabove, where R' and R" are as defined herein.

The term "disulfide" refers to a —S—SR' end group or a —S—S— linking group, as these phrases are defined hereinabove, where R' is as defined herein.

The term "carbonyl" or "carbonate" as used herein, describes a —C(=O)—R' end group or a —C(=O)— linking group, as these phrases are defined hereinabove, with R' as defined herein.

The term "thiocarbonyl" as used herein, describes a —C(=S)—R' end group or a —C(=S)— linking group, as these phrases are defined hereinabove, with R' as defined herein.

The term "oxime" describes a =N—OH end group or a =N—O— linking group, as these phrases are defined hereinabove.

The term "hydroxyl" describes a —OH group.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The term "cyano" describes a —C≡N group.

The term "isocyanate" describes an —N=C=O group.

The term "nitro" describes an —NO$_2$ group.

The term "acyl halide" describes a —(C=I)R'''' group wherein R'''' is halide, as defined hereinabove.

The term "azo" or "diazo" describes an —N=NR' end group or an —N=N— linking group, as these phrases are defined hereinabove, with R' as defined hereinabove.

The term "C-carboxylate" describes a —C(=O)—OR' end group or a —C(=O)—O— linking group, as these phrases are defined hereinabove, where R' is as defined herein.

The term "O-carboxylate" describes a —OC(=O)R' end group or a —OC(=O)— linking group, as these phrases are defined hereinabove, where R' is as defined herein.

The term "C-thiocarboxylate" describes a —C(=S)—OR' end group or a —C(=S)—O— linking group, as these phrases are defined hereinabove, where R' is as defined herein.

The term "O-thiocarboxylate" describes a —OC(=S)R' end group or a —OC(=S)— linking group, as these phrases are defined hereinabove, where R' is as defined herein.

The term "N-carbamate" describes an R"OC(=O)—NR'— end group or a —OC(=O)—NR'— linking group, as these phrases are defined hereinabove, with R' and R" as defined herein.

The term "O-carbamate" describes an —OC(=O)—NR'R" end group or an —OC(=O)—NR'— linking group, as these phrases are defined hereinabove, with R' and R" as defined herein.

The term "O-thiocarbamate" describes a —OC(=S)—NR'R" end group or a —OC(=S)—NR'— linking group, as these phrases are defined hereinabove, with R' and R" as defined herein.

The term "N-thiocarbamate" describes an R"OC(=S)NR'— end group or a —OC(=S)NR'— linking group, as these phrases are defined hereinabove, with R' and R" as defined herein.

The term "S-dithiocarbamate" describes a —SC(=S)—NR'R" end group or a —SC(=S)NR'— linking group, as these phrases are defined hereinabove, with R' and R" as defined herein.

The term "N-dithiocarbamate" describes an R"SC(=S)NR'— end group or a —SC(=S)NR'— linking group, as these phrases are defined hereinabove, with R' and R" as defined herein.

The term "urea", which is also referred to herein as "ureido", describes a —NR'C(=O)—NR"R'" end group or a —NR'C(=O)—NR"— linking group, as these phrases are defined hereinabove, where R' and R" are as defined herein and R'" is as defined herein for R' and R".

The term "thiourea", which is also referred to herein as "thioureido", describes a —NR'—C(=S)—NR"R'" end group or a —NR'—C(=S)—NR"— linking group, with R', R" and R'" as defined herein.

The term "C-amide" describes a —C(=O)—NR'R" end group or a —C(=O)—NR'— linking group, as these phrases are defined hereinabove, where R' and R" are as defined herein.

The term "N-amide" describes a R'C(=O)—NR"— end group or a R'C(=O)—N— linking group, as these phrases are defined hereinabove, where R' and R" are as defined herein.

The term "guanyl" describes a R'R"NC(=N)— end group or a —R'NC(=N)-linking group, as these phrases are defined hereinabove, where R' and R" are as defined herein.

The term "guanidine" describes a —R'NC(=N)—NR"R'" end group or a —R'NC(=N)—NR"— linking group, as these phrases are defined hereinabove, where R', R" and R'" are as defined herein.

The term "hydrazine" describes a —NR'—NR"R'" end group or a —NR'—NR"— linking group, as these phrases are defined hereinabove, with R', R", and R'" as defined herein.

The term "silyl" describes a —SiR'R"R'" end group or a —SiR'R"— linking group, as these phrases are defined hereinabove, whereby each of R', R" and R'" are as defined herein.

The term "siloxy" describes a —Si(OR')R"R'" end group or a —Si(OR')R"-linking group, as these phrases are defined hereinabove, whereby each of R', R" and R'" are as defined herein.

The term "silaza" describes a —Si(NR'R")R'" end group or a —Si(NR'R")— linking group, as these phrases are defined hereinabove, whereby each of R', R" and R'" is as defined herein.

The term "tetraorthosilicate" describes a —O—Si(OR')(OR")(OR'") end group or a —O—Si(OR')(OR")— linking group, as these phrases are defined hereinabove, with R', R" and R'" as defined herein.

As used herein, the term "hydrazide" describes a —C(=O)—NR'—NR"R'" end group or a —C(=O)—NR'—NR"— linking group, as these phrases are defined hereinabove, where R', R" and R'" are as defined herein.

As used herein, the term "thiohydrazide" describes a —C(=S)—NR'—NR"R'" end group or a —C(=S)—NR'—NR"— linking group, as these phrases are defined hereinabove, where R', R" and R'" are as defined herein.

As used herein, the term "methyleneamine" describes an —NR'—CH$_2$—CH=CR"R'" end group or a —NR'—CH$_2$—CH=CR"— linking group, as these phrases are defined hereinabove, where R', R" and R'" are as defined herein.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

System Fabrication

An exemplary microfluidic biosensing system (also referred to herein as a microfluidic array or chip), according to some embodiments of the present invention, which may be utilized as a nanowire biosensor for multiplex real-time monitoring of metabolites, is presented in FIGS. 1A and 1B.

The exemplary system included a culture compartment with several wells containing one or more solutions (e.g., solutions containing cells, reductant, and/or oxidase enzymes) arranged, individually or in combination, in the wells. The wells were in fluid communication via microchannels with a sensing compartment. The sensing compartment included a plurality of functionalized nanostructures. The solutions were introducible from the wells to the sensing compartment, by means of solenoid valves operative to close or to open fluid communication channels.

The valves allowed different samples to be switched for multiplex sensing.

In the sensing compartment, a SiNW FET array is modified with a redox-reactive functional group such as, for example, 9,10-anthraquinone-2-sulfochloride for sensing of ROS, and other ROS-producing small-molecule metabolites. ROS-producing metabolites are reacted to produce $H_2O_2$ (e.g., peroxides, $H_2O_2$), for example, in the presence of oxidase enzymes, before contacting the FET array, as exemplified in FIGS. 1C and 1D.

Then, ROS or consequent $H_2O_2$ oxidizes 9,10-dihydroxyanthracene on a FET surface to form 9,10-anthraquinone (FIG. 1D). This oxidation reaction decreases surface electron density, whereas a reductant, such as DEHA, reduces 9,10-anthraquinone to 9,10-dihydroxyanthracene to increase surface electron density.

Surface electron density varied by oxidation or by reduction changes the measured current.

The above-described microfluidic chip was fabricated as follows.

Nanowire FET Fabrication:

A core of the sensing compartment, a SiNW-FET array, was fabricated by photolithography. Source and drain electrodes of FETs were defined with a multilayer photoresist structure consisting of LOR5A (Microchem) and S1805 (Shipley). The gap between the source and drain electrodes of the FETs was 2 μm. After exposure and development of the photoresists, the patterns were metallized by e-beam evaporation of Ti/Pd/Ti (5/60/10 nm, respectively). Electrodes were thereafter insulated with a layer of 60 nm $Si_3N_4$, deposited by plasma-enhanced chemical vapor deposition at 80° C. (ICP-PECVD, Axic Inc.), and a layer of 20 nm alumina made by atomic layer deposition (ALD) (Savannah 200 system, Cambridge Nanotech).

Surface Modification:

After fabrication of the SiNW FET array, the chip was chemically modified to perform sensing of cellular metabolites (as depicted, for example in FIGS. 2A-D).

Preparation of 9,10-anthraquinone-2-sulfochloride:

The sulfonate group of sodium 9,10-anthraquinone-2-sulfonate was converted to sulfochloride, using oxalyl chloride and DMF in toluene, as depicted in inset of FIGS. 2A-D.

A mixture of sodium anthraquinone-2-sulfonate (5 grams, 0.0158 mol) and toluene (150 ml) was placed in 0.25 L round-bottomed flask, equipped with an automatic water separator (Dean-Stark trap) and condenser, and the mixture was heated under reflux for 2 hours to dry the reaction mixture. The mixture was thereafter cooled to 60° C. and oxalyl chloride (6 ml) and DMF (2 drops) were added. The resulting mixture was heated under reflux for 8 hours and a mixture of toluene and oxalyl chloride excess (30 ml) was thereafter distilled. A precipitate of sodium chloride was collected by filtration and the solvent was removed from the filtrate under reduced pressure. A solid residue was dried in vacuum overnight to give anthraquinone-2-sulfochloride (4.36 grams, 90% yield).

Preparation of 9,10-anthraquinone-functionalized SiNW FET:

After its fabrication, the SiNW FET array chip was washed with acetone, isopropyl alcohol (IPA), and deionized water (DIW) successively followed by nitrogen drying. Oxygen plasma (100 W, 0.2 Torr) was applied for 15 minutes. Immediately thereafter, the chip was covered with approx. 100 μl (3-aminopropyl)-dimethyl-ethoxysilane (APDMES; SIA0603.0, Gelest Inc.) for 10 minutes. Then, the chip was placed on a hot plate at 65° C. for 2 hours. The chip surface was thereafter washed again with IPA, followed by nitrogen drying.

The APDMES-treated chip was then placed on a hot plate at 115° C. for 25 minutes, and was thereafter immersed in a mixture containing 50 mg 9,10-anthraquinone-2-sulfochloride, 20 ml extra-dry toluene (201547, Bio-lab Ltd.) and 1 ml extra-dry pyridine (270970, SIGMA), at room temperature for 24 hours for formation of sulfonamide that connects the 9,10-anthraquinone group to the SiNW modified surface.

Surface Characterization:

Elemental composition of 9,10-anthraquinone-2-sulfochloride used for surface modification was verified using mass spectroscopy, performed (Autospec M250Q, Waters) by applying following parameters: a measurement mode of electron impact, positive ionization at 70 eV, $CH_2Cl_2$ as a solvent.

The monolayer on the 9,10-anthraquinone-2-sulfochloride-treated modified FET was characterized using X-ray photoelectron spectroscopy (XPS).

XPS measurements were performed (Multi-Technique System 5600, PHI) in ultra-high vacuum ($2.5 \times 10^{-10}$ Torr base pressure). A sample was irradiated with an Al Kα monochromated source (1486.6 eV) and outcome electrons were analyzed by a spherical capacitor analyzer using a slit aperture of 0.8 mm.

FIGS. 2A-C present the data obtained in XPS measurements during surface modification and characterization of redox-reactive SiNW FETs. FIG. 2A presents XPS measurements of SiNW surface prior to modification. FIG. 2B presents XPS measurements following silanization of the SiNW surface using APDMES, so as to generate amine groups. FIG. 2C presents the formation of a sulfonamide bond that connects 9,10-anthraquinone group to the amine-modified surface. In each of FIGS. 2A-2C, XPS spectra and atomic compositions of the modified surface for carbon (C), nitrogen (N) and sulfur (S) in each modification step are presented.

The obtained XPS spectra and atomic compositions of the modified surface presented in FIGS. 2A-C show the increase of carbon (C), nitrogen (N) and sulfur (S) after each modification step.

Figure 2D:
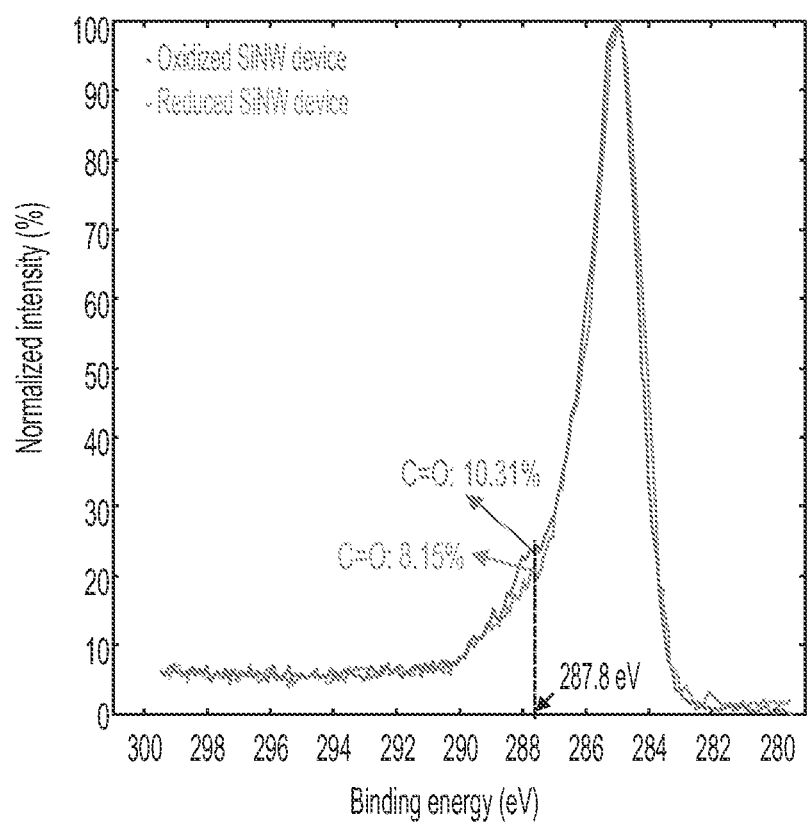

FIG. 2D presents XPS representative survey spectra of the oxidized 9,10-anthraquinone-modified silicon nanowire surface and reduced 9,10-dihydroxyanthracene-modified silicon nanowire surface. Percentage of C=O bonds was calculated from C1s curve fitting. After reduction of the surface, a decrease in C=O bond population was observed.

Samples for estimating surface chemistry during redox were either oxidized by using 1 mM $H_2O_2$, or reduced by 1% v/v DEHA (N,N-diethylhydroxylamine). Since samples were slightly charged during measurements, the input was corrected mathematically, with C1s at 285 eV taken as an energy reference. All the measurements were performed at a shallow take-off angle of 25°.

PDMS Cell Culture Compartment Featured with Solenoid-Actuated PDMS Valves:

A PDMS (Polydimethylsiloxane) culture compartment with solenoid-actuated valves, such as illustrated in FIGS. 1A and 1B, for cell culture and control of multiple solutions, was fabricated using soft lithography. Fabrication of solenoid-activated PDMS valves was according to Hulme et al. *Lab Chip* 2009, 9(1): 79-86. The valves were thereafter incorporated into the PDMS culture compartment.

Example 2

Sensing

Experimental Methods:
General Sensing Setup:

A data acquisition system was used to measure the current of a SiNW FET (Ids) induced by surface charges from ROS or $H_2O_2$, during oxidation of an analyte in an analyte solution, or from a reductant, during reduction of an analyte in an analyte solution.

For measurements of cellular metabolites/activity, cells were cultured in the chip, namely, in the culture compartment thereof (see, for example, FIG. 1A), while placing the chip in an incubator during measurements. A sample was introduced to the sensing compartment at 20 µl min$^{-1}$ by using a syringe pump.

Voltage applied to the drain and source (Vds) was 0.2 V, while voltage to the gate (Vg) was determined from Ids-Vg characteristics before sensing.

Current-versus-time signals were recorded at 1-second intervals.

All acquired signals were reversed due to presetting of the data acquisition system. During a measurement, switching of samples may have introduced some noises into electrical readouts. After each measurement, an analyte solution was replaced by a reductant, 1% v/v DEHA, to reduce the FET surface (see, FIG. 1D) to reach an electrical base level for subsequent measurements.

$H_2O_2$ Sensing:

A data acquisition system was used to measure the current of a SiNW FET (Ids) induced by surface charges from $H_2O_2$, for solutions containing various concentrations of $H_2O_2$.

Lactate, Glucose and Pyruvate Sensing:

For lactate sensing, 0.1 unit/ml of lactate oxidase (LOX; L0638, SIGMA) was added in phenol red-free medium to convert lactate to pyruvate and $H_2O_2$ before lactate reaches the FET array (as depicted in FIG. 1D).

Glucose sensing in PBS was similarly performed with 40 units/ml of glucose oxidase (GOX; G2133, SIGMA).

For pyruvate sensing, the measurements were performed in PBS with 0.625 unit/ml of pyruvate oxidase (PDX; P4105, SIGMA), 21.90 mM magnesium chloride, 1.06 mM thiamine pyrophosphate (TPP), and 0.27 mM flavin adenine dinucleotide (FAD).

Sensing can be conducted at pH 7.0 in serum-added culture medium.

pH Sensing:

A conversion of the modified FET into a pH sensor was achieved by using a reductant-added solution. After supplementing a culture medium with 0.1% v/v DEHA to reduce the modified FET surface, surface proton density varied by protonation or by deprotonation dominantly changes the measured current. Based on observations, adding 0.1% v/v DEHA to culture medium did not cause a significant change in pH.

Statistical Analysis:

Data of sensing characteristics were in means±SD, as SD is regarded as an index of variability of the mean of studied nanowire devices.

Figure 3A:
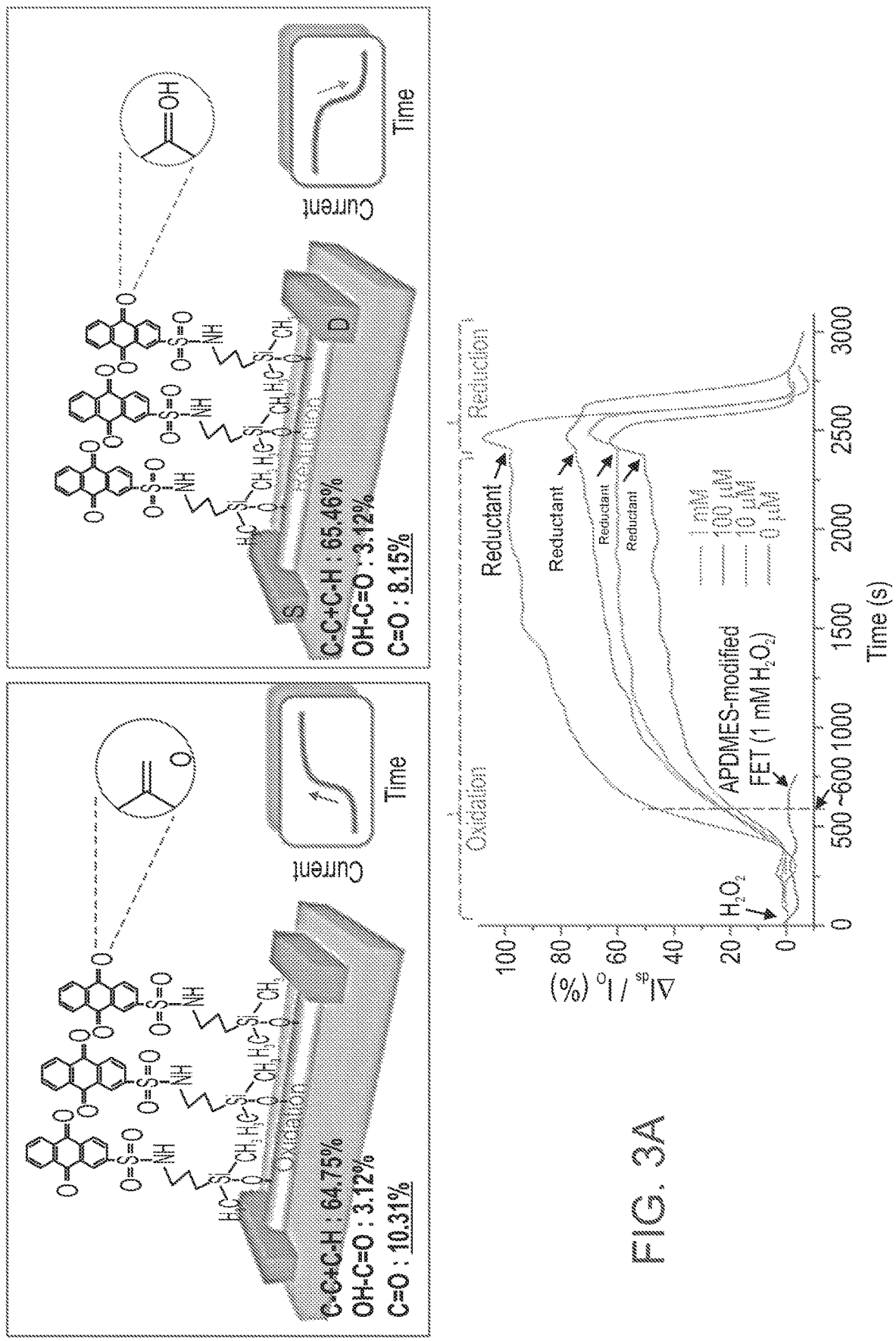
FIGS. 3A-B present the sensing characteristics of a 9,10-dihydroxyanthracene-modified SiNW FET in response to $H_2O_2$ in serum-added medium.
Figure 3B:
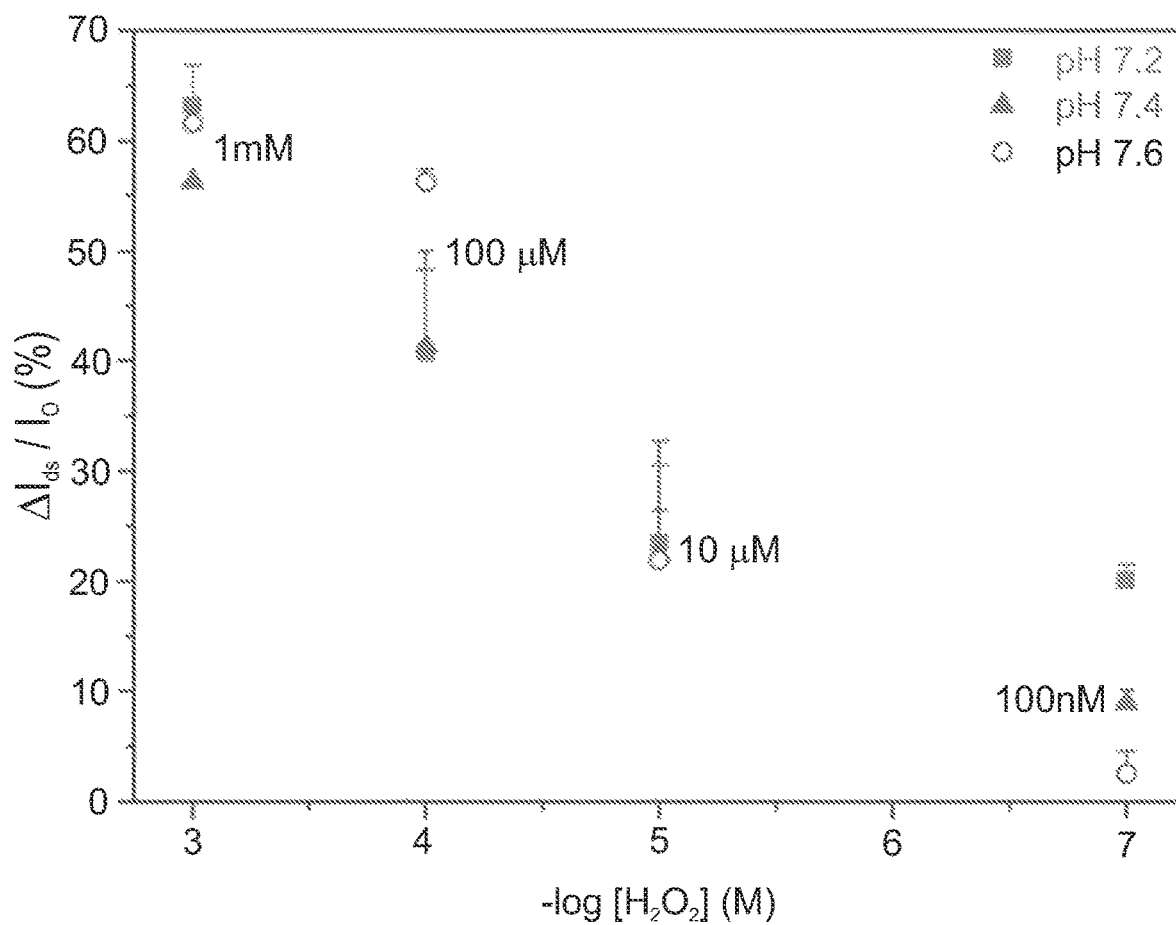

Results:

Sensing by a 9,10-dihydroxyanthracene-modified SiNW FET in response to $H_2O_2$ in serum-added medium are presented in FIGS. 3A-B.

FIG. 3A depicts the oxidation kinetics of the modified FET in different concentrations of $H_2O_2$, and the corresponding reduction kinetic upon flowing the reductant.

The obtained data show that serum-added medium without $H_2O_2$ additives also caused a detectable signal. Suggestively, the signal from a serum-added medium without $H_2O_2$ additives may be due to the complexity its contents. This signal was therefore considered as a background signal. Accordingly, acquired signals from samples were subtracted by the background signal to obtain genuine signals from $H_2O_2$.

As shown in FIG. 3A, signals acquired from the 9,10-dihydroxyanthracene-modified FET were concentration-dependent, whereas insignificant sensing response was found using an APDMES-modified FET.

The obtained data further show that about 600 seconds after introducing $H_2O_2$ samples to the FET, the concentration dependency of acquired signals was significant, whereas insignificant sensing response was found using APDMES-modified FETs. These findings firstly affirm the $H_2O_2$-specific sensing capability of 9,10-dihydroxyanthracene-modified SiNW FET, and further suggest that $H_2O_2$ concentrations can be distinguished within 10 minutes. These findings demonstrate the suitability of this system for monitoring metabolic change lasting a few-hour-long time span.

The obtained data further show that by flowing a reductant such as 1% v/v DEHA, the signal of the reduced FET surface reached a base level in about 300 seconds, and hence demonstrate that within this short period, the system is ready to be used for subsequent sensings, and that the redox-reactive FET biosensor possesses a good sensing reversibility. It is noted that a solution switch to reductant caused a jump in the electrical readout before reductant reaching the FET array.

FIG. 3A (insets) further presents comparisons of surface chemical bond populations for relevant functional groups to differentiate molecular differences of the modified monolayer at oxidation and reduction. As shown therein, reduction of the surface decreased C=O bond population. See also FIGS. 2A-D.

Additionally, $H_2O_2$ sensing responses were measured as a function of concentration and pH, and the obtained data is shown in FIG. 3B. The results show that the sensing limit to $H_2O_2$ was 100 nM, and the sensing response covered physiological concentration ranges of $H_2O_2$. See, for example, Lacy et al. *Journal of Hypertension* 1998, 16(3): 291-303.

Sensing of Small-Molecule Metabolites:

Sensing of small-molecule metabolites was assisted by oxidase enzymes' converting metabolites to $H_2O_2$.

Figure 4A:
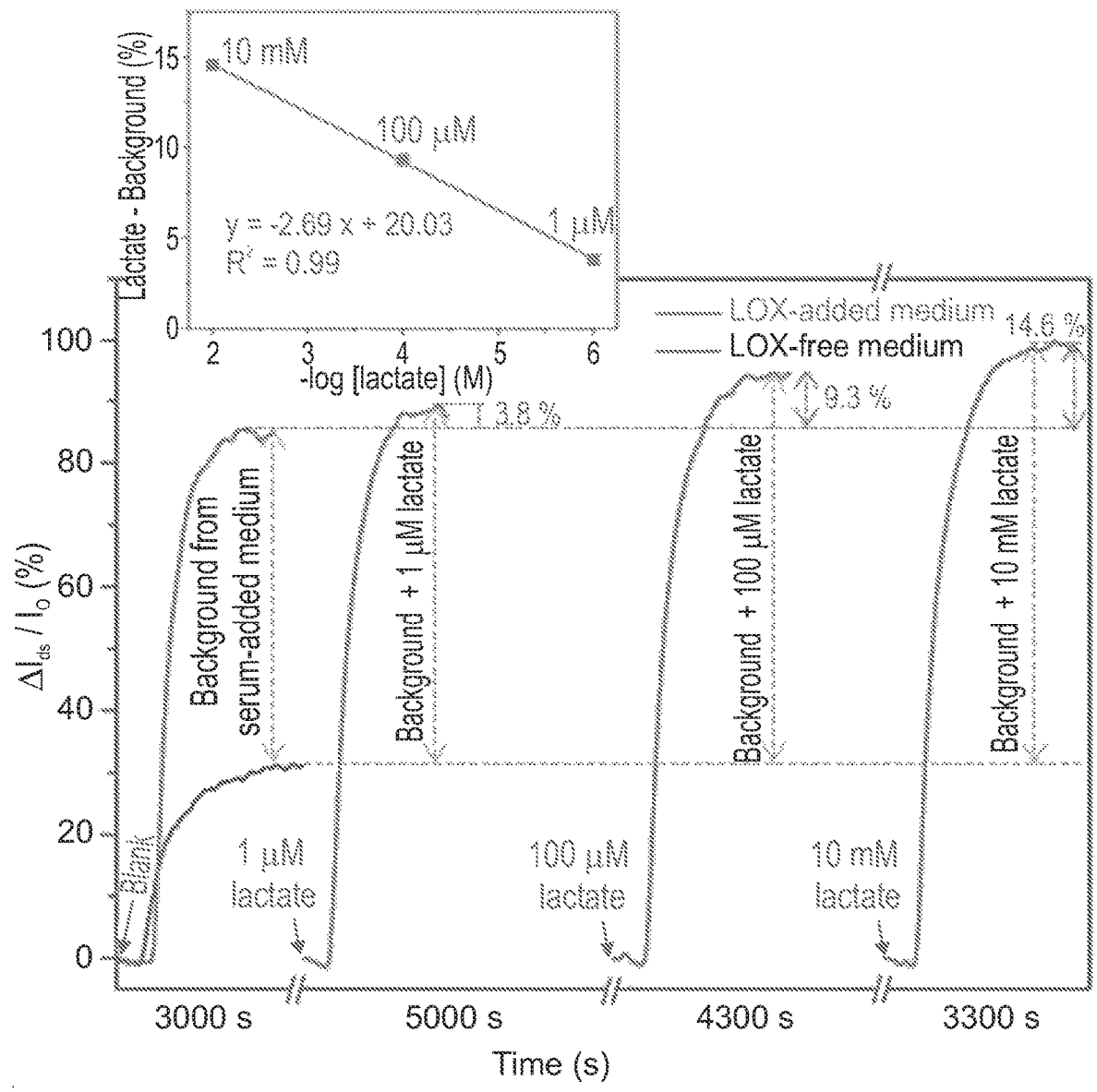
FIGS. 4A-C present the sensing characteristics of a 9,10-dihydroxyanthracene-modified SiNW FET in response to the small-molecule metabolites lactate (FIG. 4A) and glucose (FIG. 4B) by means of oxidases in serum-added culture medium, and to the small-molecule metabolite pyruvate in PBS (FIG. 4C). Insets present the corresponding standard curve. (LOX: lactate oxidase; GOX: glucose oxidase, PDX: pyruvate oxidase; Vg=0 V, Vds=0.2 V).

FIG. 4A presents the concentration-dependent sensing characteristic of lactate in serum-containing medium. As shown therein, for a solution without lactate, the signal of a LOX-added sample (the first gray curve from the left) was higher than its LOX-free counterpart (the dark curve). Again, the difference between the two signals may be due to the high complexity of the serum-added medium. Therefore, the difference between the two signals was defined as the background signal.

To obtain genuine signals from lactate, readings of LOX-added samples were subtracted by readings of LOX-free corresponding samples, namely, subtracted by the signal of LOX-free blank medium, since lactate sample without LOX does not cause any redox to alter measured currents. The background signal was further subtracted from acquired lactate signals. A corresponding standard curve is presented in the inset of FIG. 4A.

The obtained data show that the sensing limit to lactate in serum-added medium was 1 μM, and the detection range covered the physiological range of lactate. See, for example, Wacharasint et al. *Shock* 2012, 38(1): 4-10.

Figure 4B:
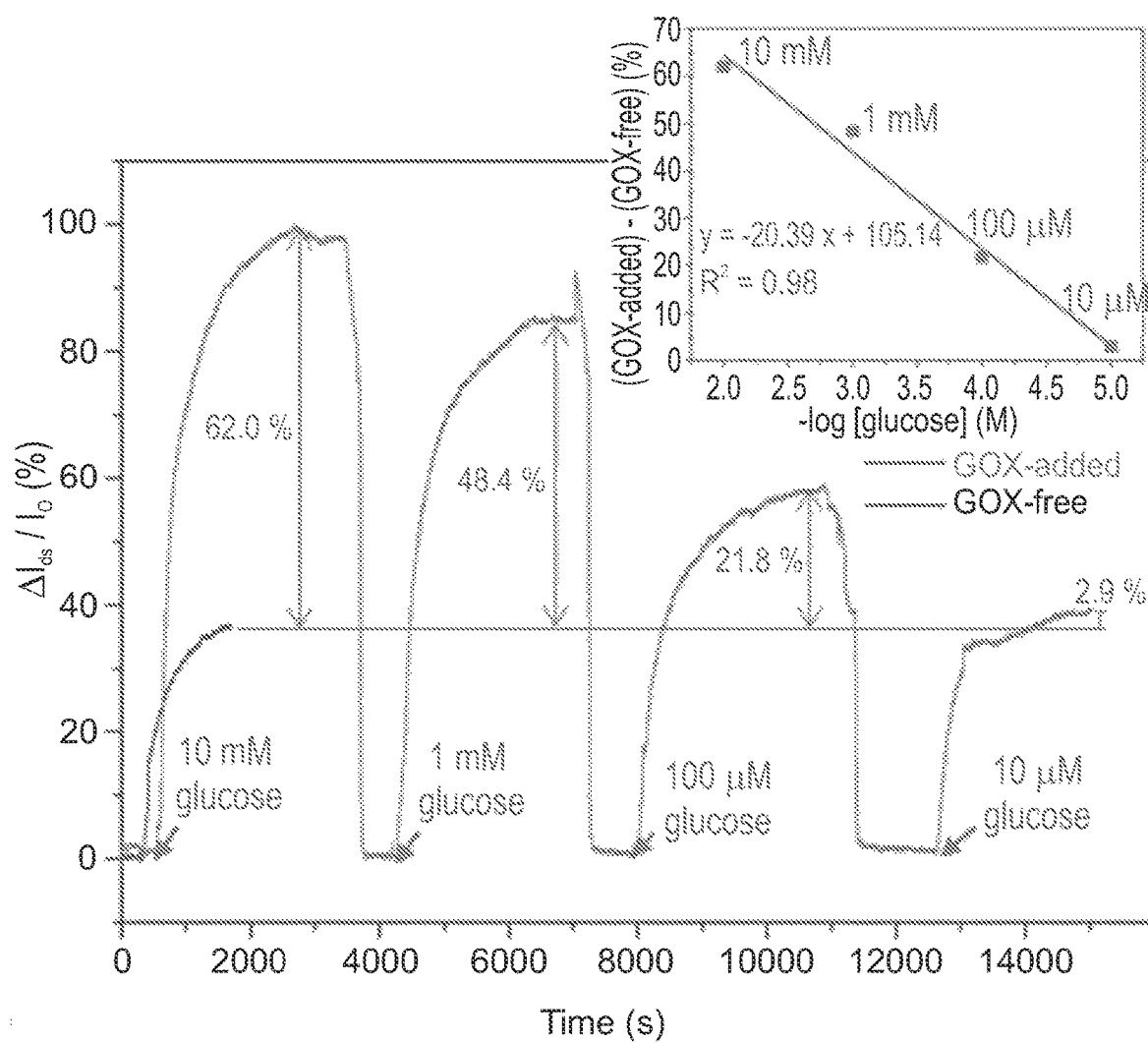

FIG. 4B presents the data obtained for glucose sensing responses in PBS. Similarly to lactate sensing, for acquiring signals from glucose, readings of GOX-added samples (the gray curves) were subtracted by the reading of 10 mM glucose-containing GOX-free sample (the dark curve), since glucose additives without the presence of GOX did not generate $H_2O_2$ to react with the redox-reactive FET sensor. The corresponding standard curve is presented in the inset.

The obtained data show that the sensing limit to glucose in PBS was 10 μM, and the detection range covered the physiological range of glucose. See, for example, Lu et al. (2009), supra.

Figure 4C:
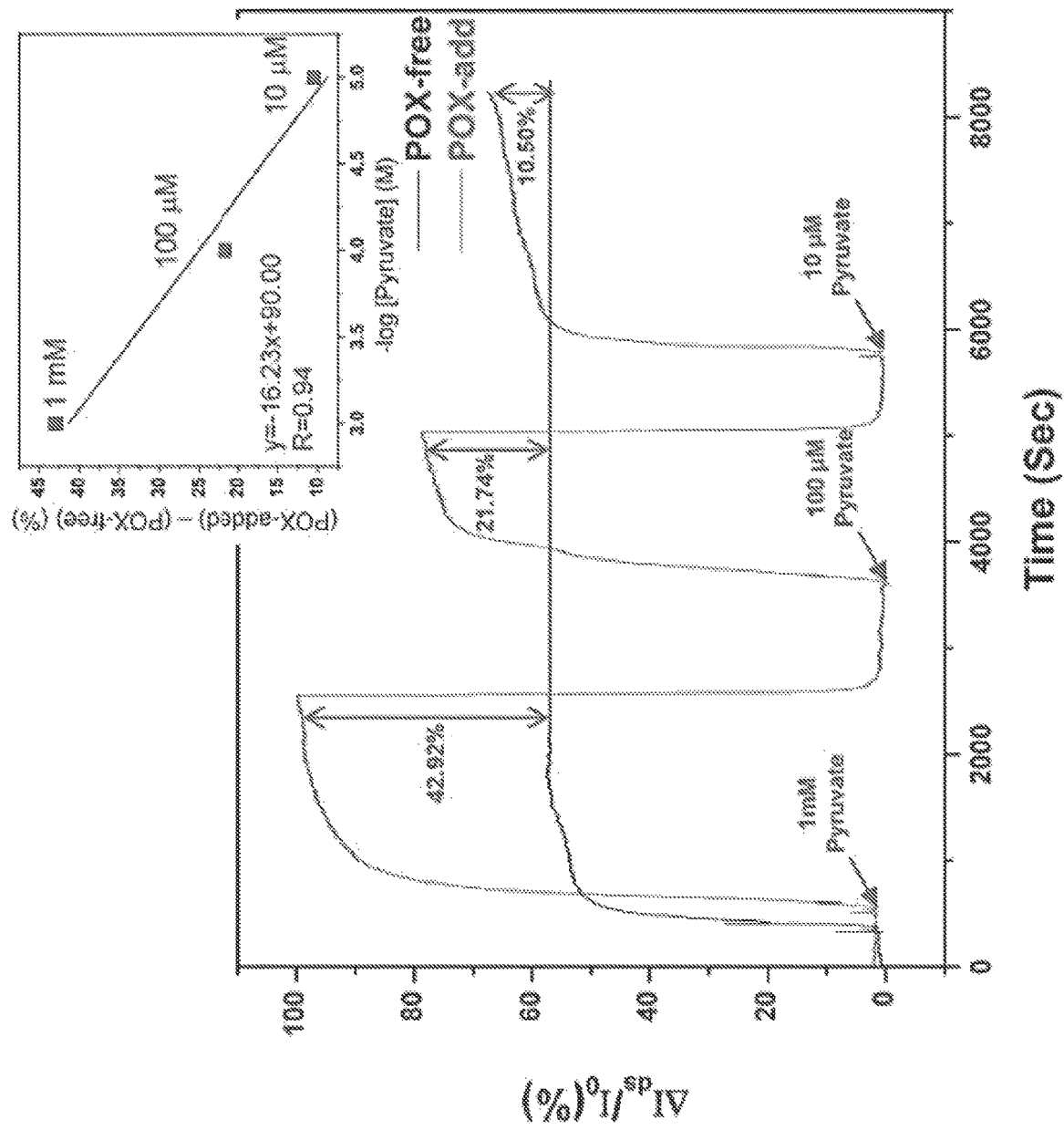

FIG. 4C presents the pyruvate sensing responses in PBS. Readings of PDX-added samples were in gray, while a reading of a PDX-free sample was in dark. To obtain genuine signals from pyruvate, readings of PDX-added samples were firstly subtracted by readings of PDX-free corresponding sample, namely, subtracted by the signal of 10 mM Pyruvate-containing PDX-free sample since pyruvate samples without PDX does not cause any redox to alter measured currents.

Figure 5A:
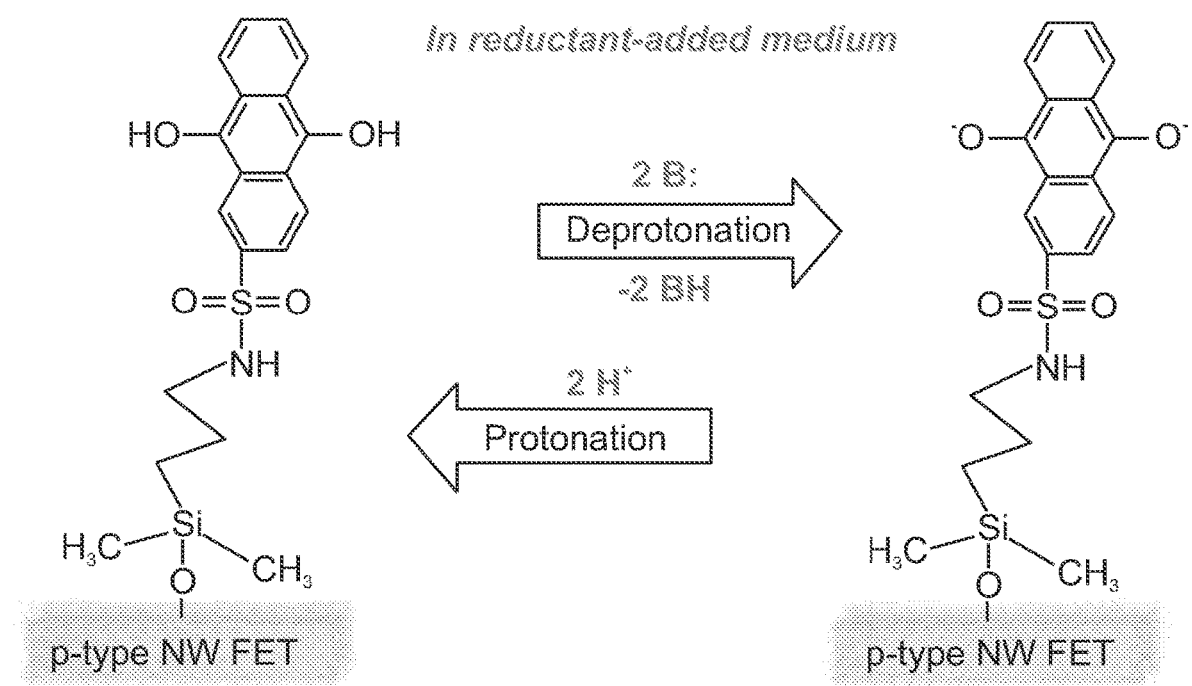
FIGS. 5A-C present sensing of pH in a reductant-supplemented medium using a 9,10-dihydroxyanthracene-modified NW FET.

It is noted that no significant background signal was found in the pyruvate sensing in PBS, suggesting that the background sensing signal is dependent on the complexity of a sensing medium.

pH Sensing:

The modified FET described hereinabove was converted into a pH sensor as schematically illustrated in FIG. 5A, by simply adding a reductant. After supplementing a culture medium with DEHA to reduce the modified monolayer to 9,10-dihydroxyanthracene and the $H_2O_2$ content, surface proton density varied by protonation or by deprotonation dominantly changes the measured current.

For pH sensing, 0.1% v/v DEHA was supplemented in the sensing medium to reduce the 9,10-anthraquinone monolayer on the FET surface to obtain 9,10-dihydroxyanthracene (see also FIG. 1d) and $H_2O_2$ simultaneously. Therefore, no significant amount of $H_2O_2$ in a DEHA-supplemented medium altered a measured signal. As a result, surface proton density, varied by protonation or by deprotonation, dominantly changes an acquired signal.

Adding 0.1% v/v DEHA to culture medium did not cause a significant change in pH based on our observations.

Figure 5B:
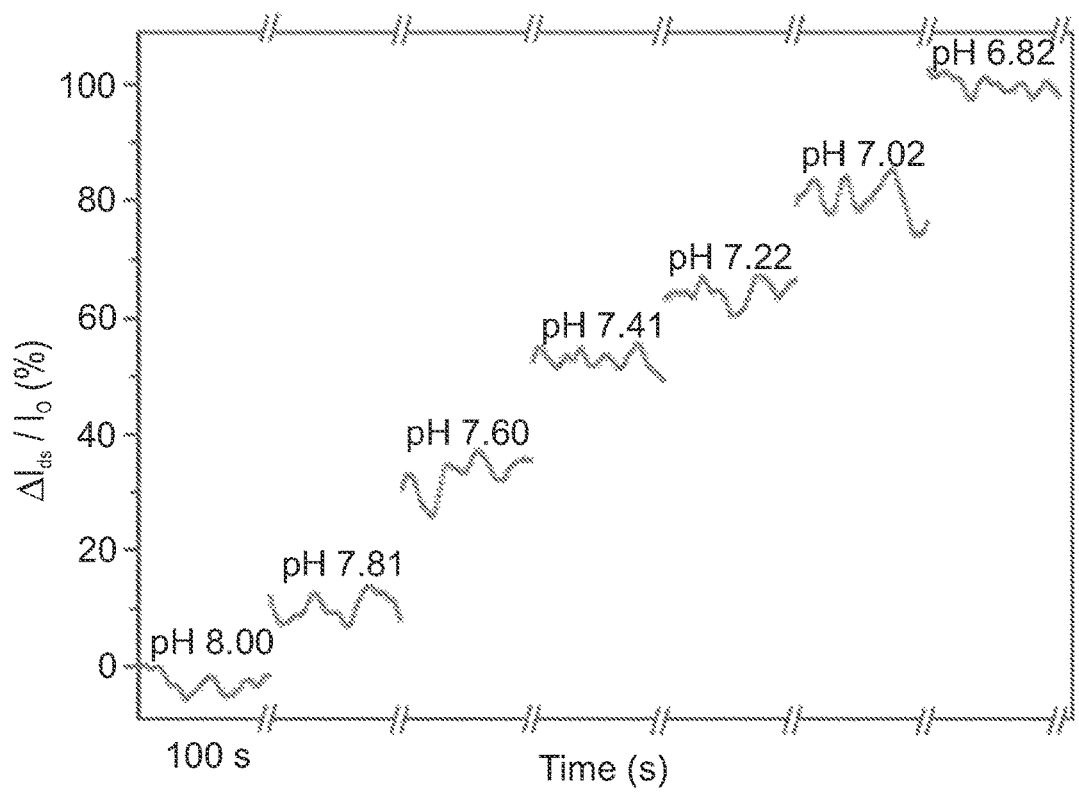

FIG. 5B presents the pH-dependent sensing response in reductant-added medium. As shown therein, the pH sensing sensitivity was 0.2 pH unit, and the detection capability covered physiological pH range.

Figure 5C:
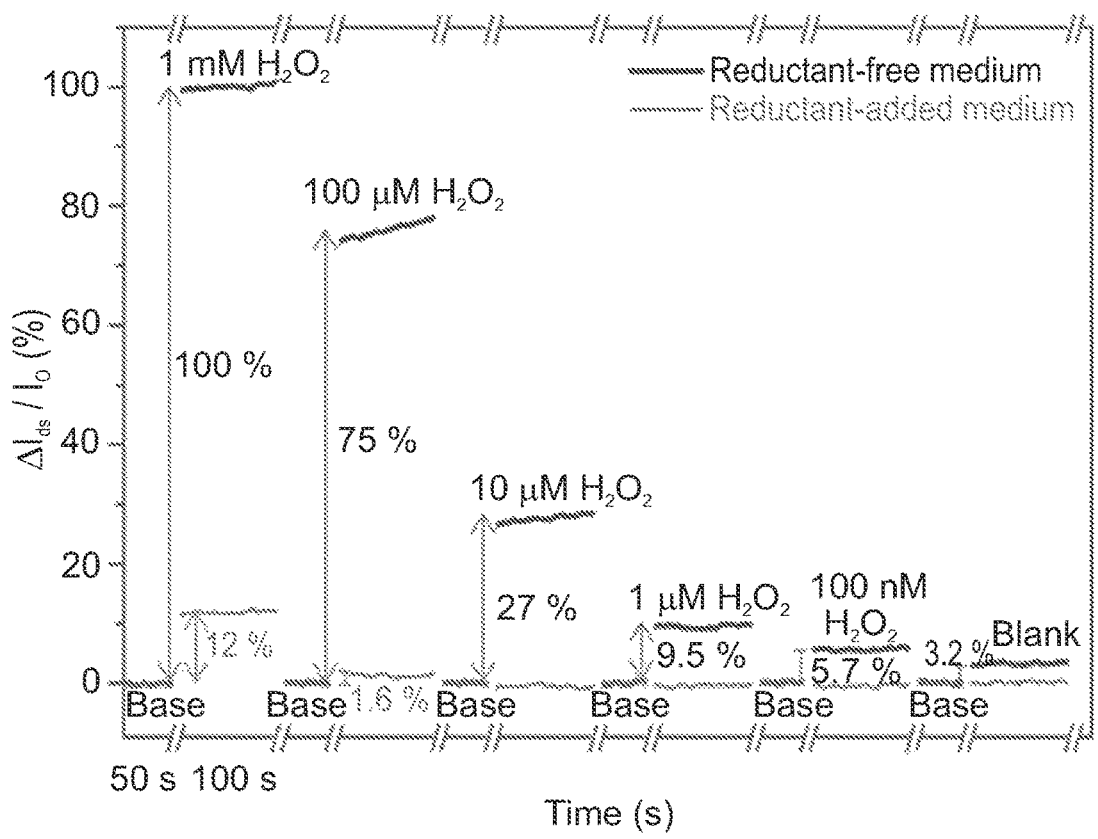

FIG. 5C presents comparative sensing of $H_2O_2$ in reductant-free medium and reductant-added medium. As shown therein, in reductant-added medium, $H_2O_2$ concentrations lower than 1 mM, which wholly cover normal physiological levels of hydrogen peroxide in blood [Lacy et al. *Journal of hypertension* 1998, 16(3): 291-303; Valko et al. *Int J Biochem Cell B* 2007, 39(1): 44-84], did not cause a significant signal comparing to signals from reductant-free medium. In other words, the sensor in the reductant-added medium was insensitive to $H_2O_2$ in a normal physiological concentration. Thereby, by using a reductant-supplemented solution, pH sensing specificity of the 9,10-dihydroxyanthracene-modified NW FET is enabled.

Example 3

Monitoring Metabolic Activity of Cells

Experimental Methods:

Cell Culture, Drug Treatment and Viability Assessment:

Human T lymphocytes, Jurkat (TIB-152, ATCC), were cultured and incubated at 37° C. under a humidified 5% $CO_2$ atmosphere. The culture medium used was RPMI 1640 medium (52400, GIBCO) with 10% fetal bovine serum (FBS; 04-001-1A, Biological Industry) and 1% penicillin/streptomycin (15140, GIBCO).

During experiments, cells were re-suspended in phenol red-free medium (11835-063, GIBCO) in the presence or absence of a drug, either methotrexate hydrate (MTX; M8407, SIGMA) or 2-deoxy-D-glucose (2DG; D6134, SIGMA), at a density of $1 \times 10^6$ cells/ml.

Cellular samples were dispensed into the wells of the sensing chip (see FIGS. 1A and 1B) in an incubator.

Cell viability was estimated by using a hemocytometer to count trypan blue-stained cells.

Isolation of Primary Human B Cells:

Peripheral blood (PB) cells were obtained from healthy donors and from patients with chronic lymphoid leukemia (CLL).

To isolate low-density cells, PB cells were fractionated using Ficoll-Paque (GE Healthcare). Isolated cells were re-suspended in phenol red-free serum-added medium for sensing.

To isolate B-lymphocytes (CD19+), PB low-density cells from patient samples or PB from healthy samples were fractionated using B-cells purification kit micro-immunomagnetic beads (Miltenyi Biotec) following the manufacturer's instructions, and the fractionated B cells were immediately used for sensing.

Sensing was performed as described hereinabove.

Analytically, flow cytometry analysis confirmed that more than 93% of the normal or CLL fractionated cells were CD19+.

Extracellular ROS/Lactate Assay Using Dichlorodihydrofluorescein:

Control experiments, for comparing with nanowire sensing of cells, were performed by using dichlorodihydrofluorescein (DCFH). In principle, DCFH is oxidized to fluorescent dichlorofluorescein (DCF) by ROS.

DCFH was prepared as described in Cathcart et al. [*Analytical biochemistry* 1983, 134(1): 111-116].

Jurkat cells were cultured in phenol red-free RPMI 1640 medium, with 10% FBS and 1% penicillin/streptomycin, at a density of $1\times10^6$ live cells/ml.

Before a measurement, cells were removed to obtain cell-free medium. Then, cell-free medium sample was added with DCFH and loaded into wells of a 96-well black plate at 100 µl per well. The plate was prevented from light and incubated at room temperature for 10 minutes, and then analyzed using a plate reader (i-200, Tecan) to determine consequent emission intensities of fluorescent DCF at 525 nm.

Concentration of lactate metabolite was similarly estimated using DCFH. The main additional procedure was incubating cellular samples with 0.004 unit/ml LOX at 37° C. for 5 minutes, then adding DCFH to the samples for measurements. To obtain signals from lactate, readings of LOX-added samples were subtracted by readings of LOX-free counterparts.

Statistical Analysis:

Data regarding cellular metabolites are presented in means±standard error of the mean (SEM) or standard deviations (SD). In addition, two-tailed, two-sample t-tests were performed to statistically analyze significances in data regarding cellular metabolites.

Results:

Sensing Using a T-Cell Line:

Reactive oxygen species (ROS) form as a natural byproduct of normal metabolism of oxygen and have important roles as signaling molecules in the regulation of a variety of biological processes. As a signaling molecule, one important feature of ROS is its ability to move between different compartments, e.g. to cross cell membranes. Therefore, escalating intracellular ROS would diffuse through cell membranes to extracellular space as an indicator to display a metabolic activity.

24-hour monitoring of metabolic activity of drug-treated Jurkat cells by measuring extracellular ROS levels using the nanowire biosensor, was performed and the obtained data is presented in FIGS. 6A-G.

Figure 6E:
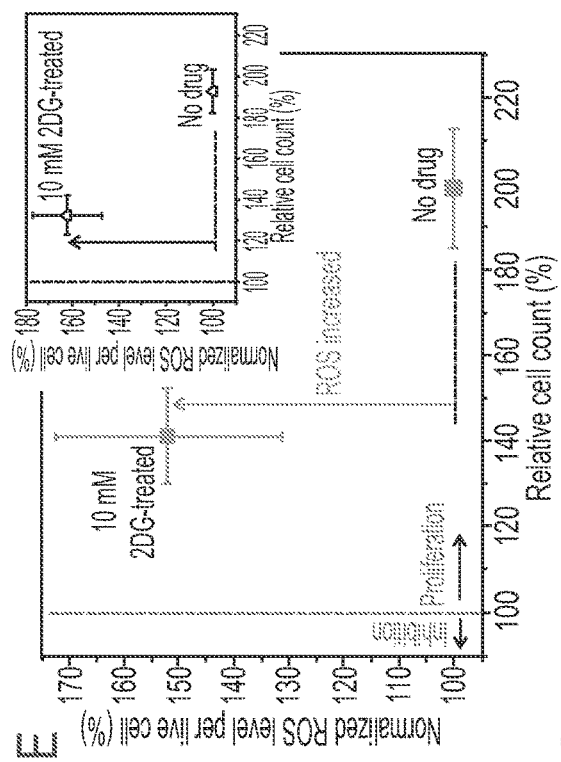
Figure 6G:
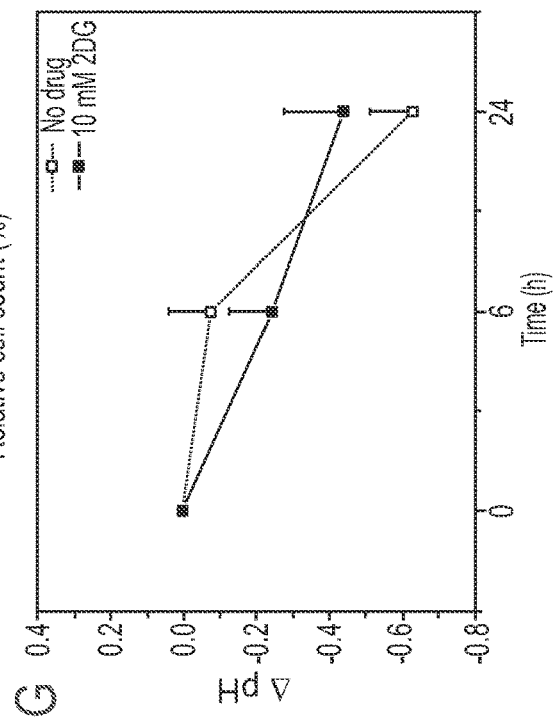
Figure 6D:
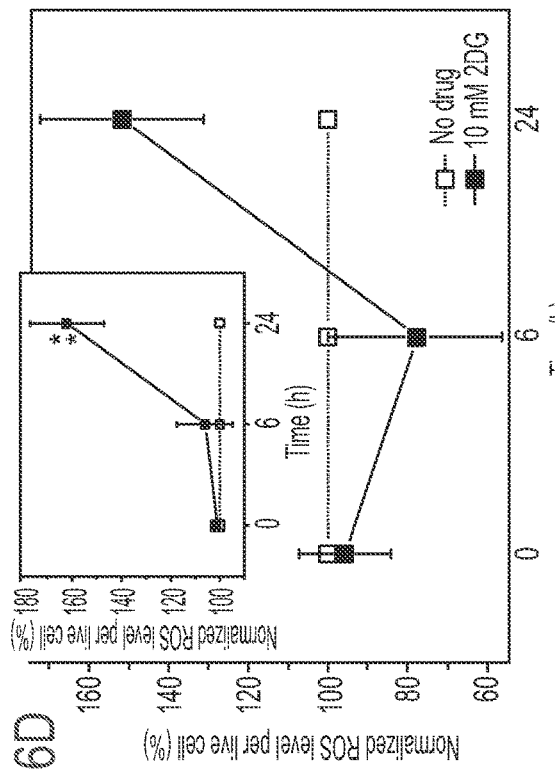
Figure 6F:
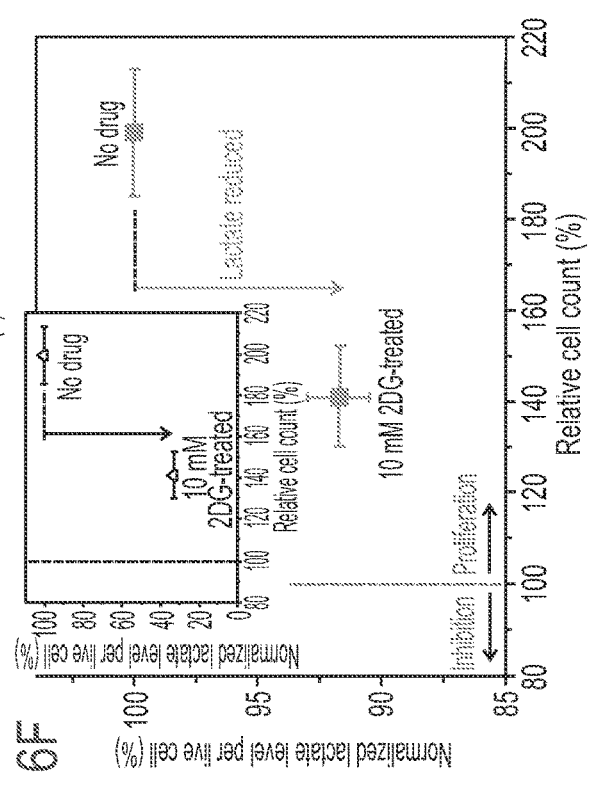

Data for Jurkat cells treated by MTX are presented in FIG. 6A-6C and for cells treated by 2DG are presented in FIG. 6D-6F.

Measured ROS levels were normalized by the number of live cells.

Relative cell count, presented in FIGS. 6B and 6E-6F, is a ratio of the cell count at t=24 hours to the initial cell count.

The results show that a noticeable decrease of ROS level of both MTX-treated and 2DG-treated Jurkat cells was found at t=6 hours (see, FIGS. 6A and 6D). It can be explained by antioxidants' reacting to low levels of hydrogen peroxide [Valko et al. (2007) and Wacharasint et al. (2012) supra].

The results further show that after 24-hour treatment, ROS levels of drug-treated Jurkat cells were significantly accumulated (see, FIGS. 6A and 6D), and cell proliferation rates have been reduced (see, FIGS. 6B and 6E).

The obtained data may be used to analyze the mechanism of action. It may suggest that the expression of pro-oxidants may be stimulated after attempts to reduce ROS level. As a result, pro-oxidants could induce oxidative stress, either by producing reactive oxygen species or by inhibiting antioxidants [Sablina et al. *Nat Med* 2005, 11(12): 1306-1313] to thereby inhibit cell proliferation [López-Lázaro M. *Cancer letters* 2007, 252(1): 1-8]. It is to be noted that data from control experiments (shown in the insets of FIGS. 6A-F), obtained by using DCFH as described hereinabove, in Fluorescence spectroscopy analyses, is in line with the observations based on the NW biosensor detection.

Cancer cells produce energy by a high rate of glycolysis and secret more lactate comparing to normal tissue, in a phenomenon known as "the Warburg effect". Therefore, extracellular lactate is therefore an important indicator of cellular metabolic activities.

The correlation between extracellular lactate level of 2DG-treated Jurkat cells and a resultant cell proliferation rate after 24 hours was investigated. The obtained data is presented in FIG. 6F and show that cellular lactate secretion of 2DG-treated Jurkat cells was decreased, and the cells had a reduced proliferation rate. This is consistent with a previous study concluding that death receptor-induced apoptosis was upregulated by using 2DG to inhibit glycolysis [radelli et al. *Oncogene* 2010, 29(11): 1641-1652].

In addition, pH sensing of drug-treated Jurkat cells was performed, and obtained data is presented in FIGS. 6C and 6G. As shown therein, pH of all cultured cells turned to be more acidic with time, whereby pH of 2DG-treated cells was more basic than the control (see, FIG. 6G), probably due to the reduced lactate secretion (as shown in FIG. 6F). Since lactic acid has a $pK_a$ of 3.9, it is dissociated into a lactate anion and a proton at physiological pH. Consequently, the decreased lactate secretion of 2DG-treated Jurkat cells has a less impact on extracellular acidification comparing to the control.

Figure 6I:
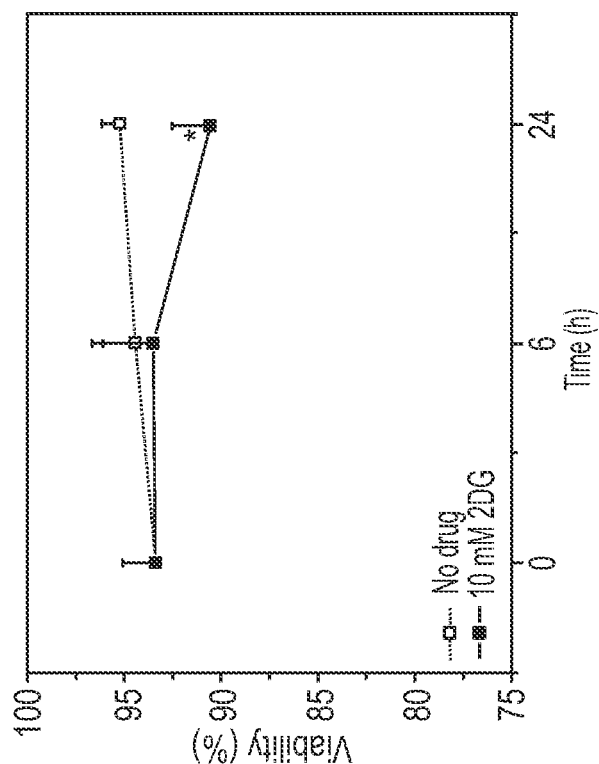
Figure 6H:
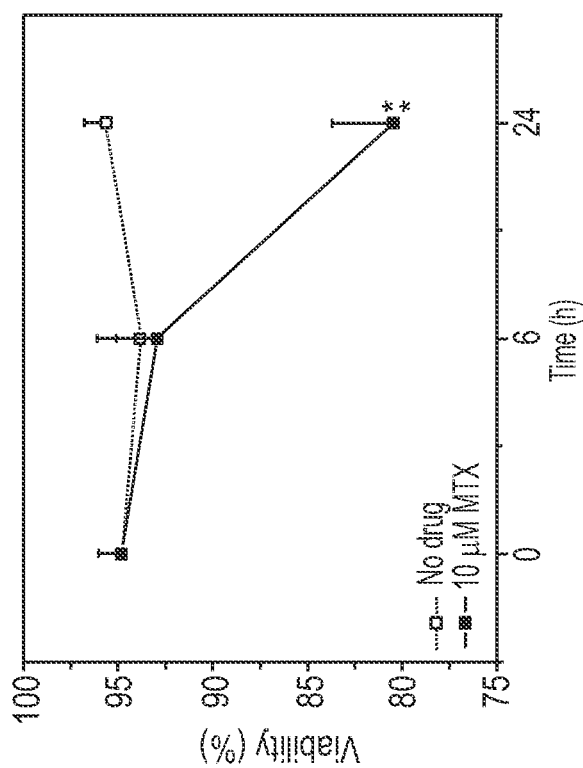

FIGS. 6H and 6I present the cell viability of MTX-treated samples and 2GD-treated samples, respectively, confirming the anti-proliferative activity of the drugs.

Sensing Using Primary Human B Cells:

Metabolic levels of chronic lymphocytic leukemic (CLL) cells and normal B cells were monitored for 24 hours and metabolic significances were determined.

The measured metabolic levels of CLL cells were firstly normalized by the number of live cells, then further normalized by the metabolic levels of normal B cells. The obtained data are presented in FIG. 7A, and show that the ROS levels and lactate levels of CLL cells were higher than those of normal B cells. These findings are in accordance with previous studies showing that cancer cells produce higher levels of $H_2O_2$ than normal cells [Szatrowski and Nathan C F. *Cancer Res* 1991, 51(3): 794-798; Zieba et al. *Respiratory medicine* 2000, 94(8): 800-805].

The results also validate the hypothesis that cancer cells secret more lactate comparing to normal tissue.

The data further imply that the redox-reactive nanowire biosensor would estimate metabolic changes of cancer cells during a treatment to realize personalized medicine.

Figure 7A:
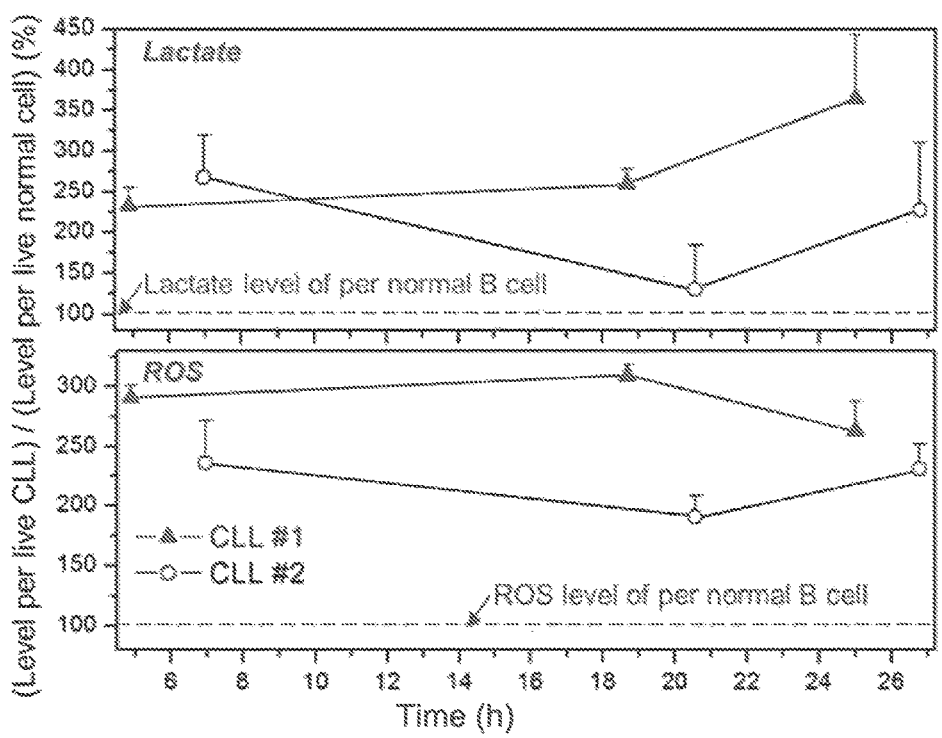
FIGS. 7A-B present metabolic levels of chronic lymphocytic leukemic (CLL) cells and normal B cells (FIG. 7A) and viability thereof (FIG. 7B). Data were means±standard deviations (SD), n=6 devices; Student's t-tests were employed; * denotes $P<0.05$, ** denotes $P<0.01$); Data obtained for a 24-hour viability observation of primary human B cells (CLL: chronic lymphoid leukemic cells; Normal: normal B cells).
Figure 7B:
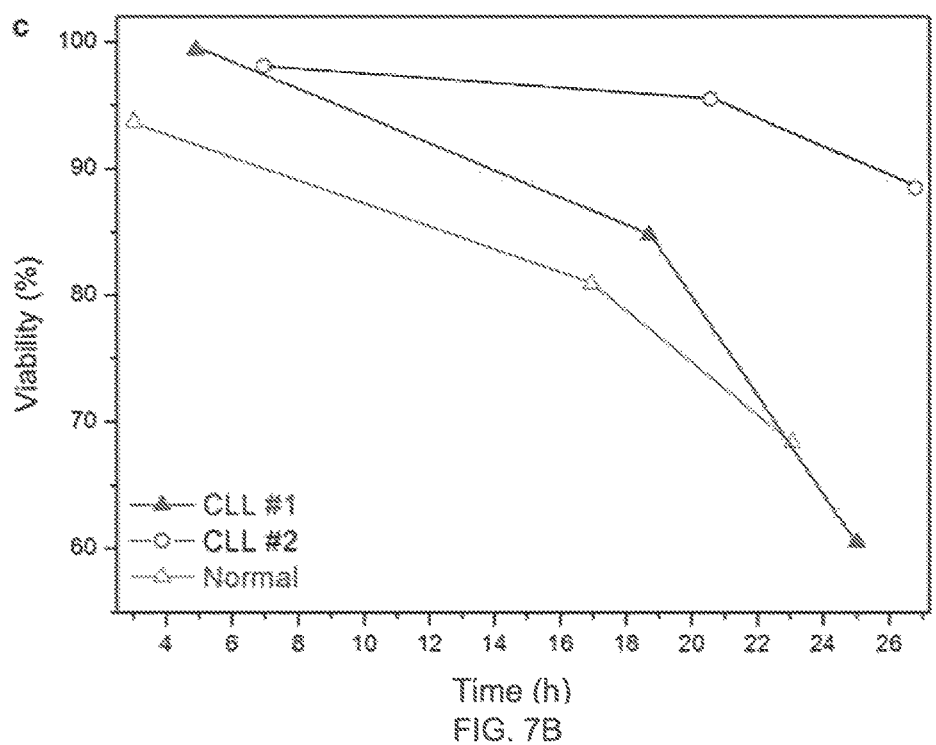

FIGS. 7A and 7B present pathological features of CLL cells (FIG. 7A) and cell viability (FIG. 7B) of the tested samples. Significantly, ROS levels and lactate levels of CLL cells were higher than those of the normal B cells.

Table 1 below presents biological parameters of the CLL cells.

TABLE 1

| CLL patient No. | Sex | Age (Yr) | WBC ($10^9$/L) | Lymphocytes (%) | Hemoglobin (g/dL) | Platelets ($10^9$/L) | Rai stage | $\beta_2$Microglobulin (mg/dL) | Cytogenetics | Previous Treatment |
|---|---|---|---|---|---|---|---|---|---|---|
| 1 | M | 78 | 18090 | 81 | 12.8 | 120000 | I | 2.3 |  | none |
| 2 | F | 76 | 97000 | 93 | 13.2 | 171000 | II |  | normal | leukeran |

Example 5

Electrically Controllable Device

A prototype redox-reactive nanowire sensor device was fabricated and operated, according to some embodiments of the present invention.

The surface of the nanowire sensor was modified covalently with redox reversible moiety, 9, 10-dihydroxyanthracene. The reversible transformation between 9, 10-dihydroxyanthracene and 9,10-anthraquinone can be ensured either by applying chemicals or voltage. The 9,10-dihydroxyanthracene/9,10-anthraquinone redox-reversible system was selected as the sensing moiety, due to the rapid oxidation of the 9,10-dihydroxyanthracene in the presence of metabolic products such as $H_2O_2$ and reactive oxygen species, via conversion to 9,10-anthraquinone. On the other hand, 9,10-anthraquinone in aqueous solution can be reversibly reduced to 9,10-dihydroxyanthracene in the presence of reductants such as N,N-diethylhydroxylamine, or by applying electric potential. Therefore, by covalently binding this redox system to SiNW FET array surface via a short linker, a redox-reactive SiNW FET nano-device was achieved 9, 10-dihydroxyanthracene tends to react with oxygen reactive species (ROS) or with $H_2O_2$. Both ROS and $H_2O_2$ are products of cellular metabolism. In addition $H_2O_2$ is a product of metabolism by enzymes from the oxidase family. Therefore by introducing a metabolite (such as, but not limited to, glucose) to specific oxidase enzyme (such as, but not limited to, glucose oxidase) a selective production of $H_2O_2$ occurs. ROS or $H_2O_2$ selectively oxidize the 9, 10-dihydroxyanthracene on the surface of the nanowire field-effect transistor (FET), as a result the charge density on the nanowire surface is changed and alters the conductivity of the device.

The reversible redox properties of the modified moiety can be used to measure, optionally and preferably continuously, metabolic activity. By controlling the electron/charge density that regulates the current on the nanowire device, the amount of moieties that can be oxidized by ROS and $H_2O_2$ (9, 10-dihydroxyanthracene population, in the present example) can be controlled. For example, by changing the gate electrode voltage the charge density on the nanowire can be regulated. In some embodiments of the present invention a constant population of 9, 10-dihydroxyanthracene is maintained on the nanowire surface by applying constant gate voltage. In these embodiments, there is an equilibrium between the gate voltage and the 9, 10-dihydroxyanthracene population on the nanowire surface. By adding ROS or $H_2O_2$ to the system this equilibrium is changed due to the presence of oxidative species. The presence of oxidative species reduce the population of 9, 10-dihydroxyanthracene on the nanowire surface resulting in a change in the conductivity of the device.

The advantage of the device of the present embodiments is that it allows a direct analysis of bio-samples on a single nanowire device, for selectively detecting specific metabolite, without the requirement of time and money consuming steps such as labeling and purification.

By operating the fabricated prototype device, the present inventors successfully demonstrated continuous sensing of metabolites in physiological solutions without preprocessing. Typically, concentration-dependent sensing of $H_2O_2$ and metabolites coveres physiological concentration ranges.

The present inventors found that for practical use, such as, but not limited to, in vivo sensing, particularly when there is a need to measure exact amounts of metabolite (for example, continuous glucose monitoring for diabetes), it is difficult, if not impossible to build a calibration curve for the sensor device while being mounted on or implanted in the living organism. The present inventors found that the electrically controlled device of the present embodiments can be self calibrated. Preferably, this is achieved using an array of nanowire FETs on the same device or chip or platform. Some of the nanowire FET devices are modified with non redox active moiety only. Because there is no specific oxidative reaction from the in vivo environment to the non redox active moiety modified nanowire surfaces, the signal that comes from the non redox active moiety modified nanowire it is define as the background. The amount of the metabolite can be determined by subtracting the background from the signals from the redox active moiety modified nanowires.

Figure 13A:
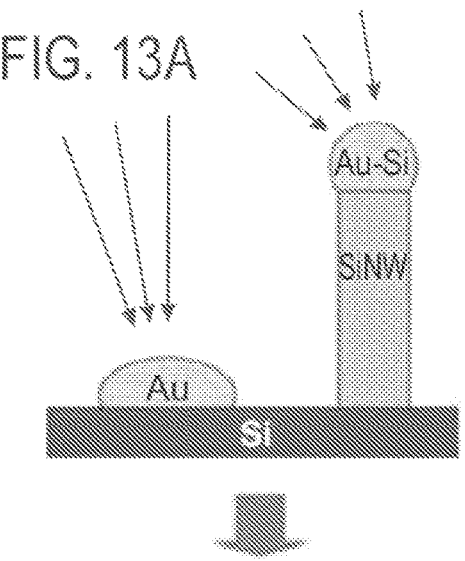
FIGS. 13A-E are schematic illustrations of a process suitable for fabricating according to some embodiments of the invention an electrically controlled sensor device, such as, but not limited to, the device shown in FIG. 12.
Figure 13B:
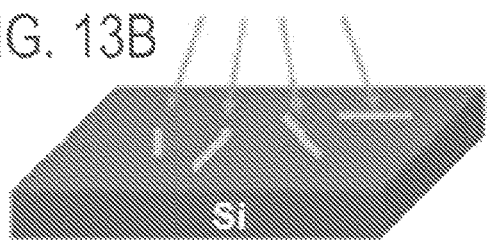
Figure 13C:
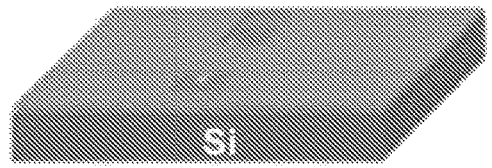
Figure 13D:
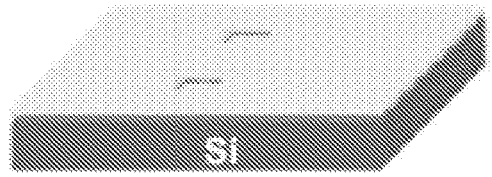
Figure 13E:
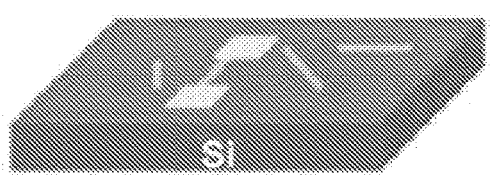

FIGS. 12 and 13A-E illustrate a fabrication process of a 20 nm diameter P-type SiNW-FET device on 3 inch silicon wafer with 600 nm oxide layer, according to some embodiments of the present invention. P-type SiNWs were synthesized by chemical vapor deposition (CVD) system (via vapor liquid solid (VLS) process) (FIG. 13A). The p-type SiNWs were deposited on silicon substrate with 600 nm oxide layer and outer metal pads (5 nm Cr and then 60 nm Au), that were fabricated in advance by lithography (FIG. 13B). The source and drain electrodes were deposited with the use of a multilayer photoresist structure consisting of 500 nm LOR5A (Microchem) and 500 nm 1805 (Shipley). After exposure and development of the electrode patterns (FIG. 13C), the contacts were metallized by e-beam and thermal evaporation of Ni (60 nm) respectively, and were then passivated with an insulating layer of Si3N4 (60 nm thick) deposited by plasma-enhanced chemical vapor deposition at 80° C. (ICP-PECVD, Axic Inc.) and a layer of 10 nm alumina (ALD deposition using a Cambridge Nanotech Savannah 200 system) (FIG. 13D). A lift-off of un-exposed photoresists layers and a thermal annealing of SiNWs and metal contacts were preformed (FIG. 13E). The separation between the source and drain electrodes for each FET was about 2 μm.

Figures 14A, 14B, 14C:
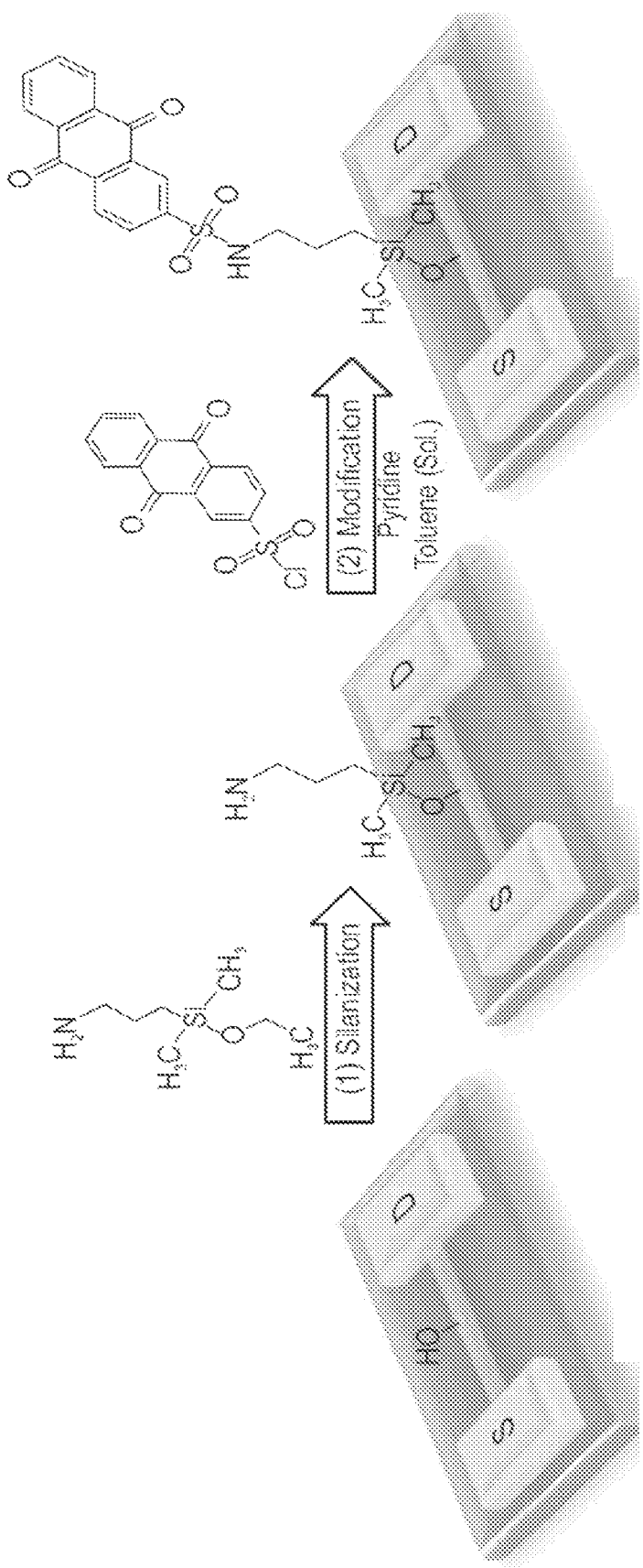
FIG. 14A-C show a modification procedure, according to some embodiments of the present invention
Figure 14D:
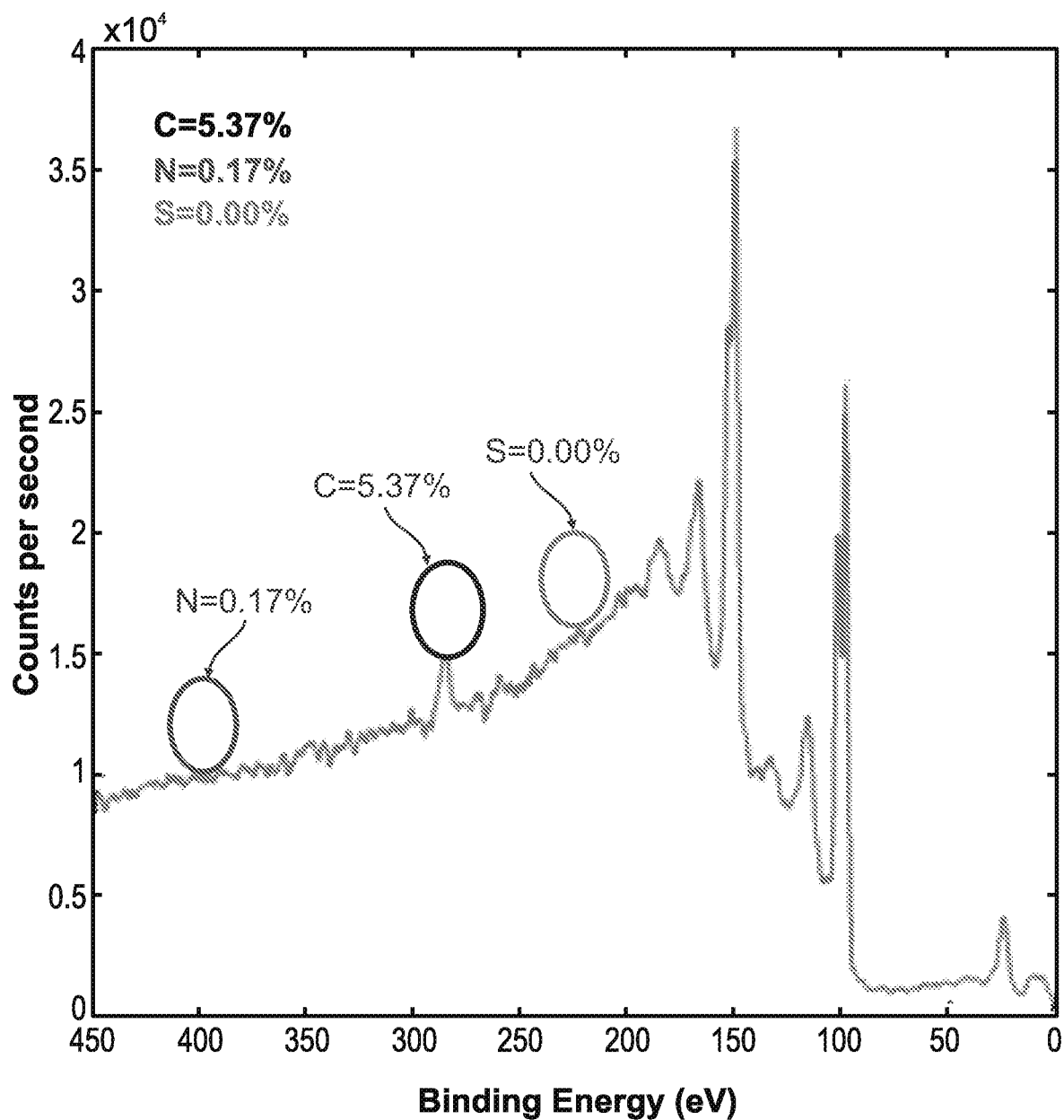
FIGS. 14D-F show XPS spectra and atomic compositions of a modified surface as obtained for each modification stage of FIGS. 14A-C, respectively.
Figure 14E:
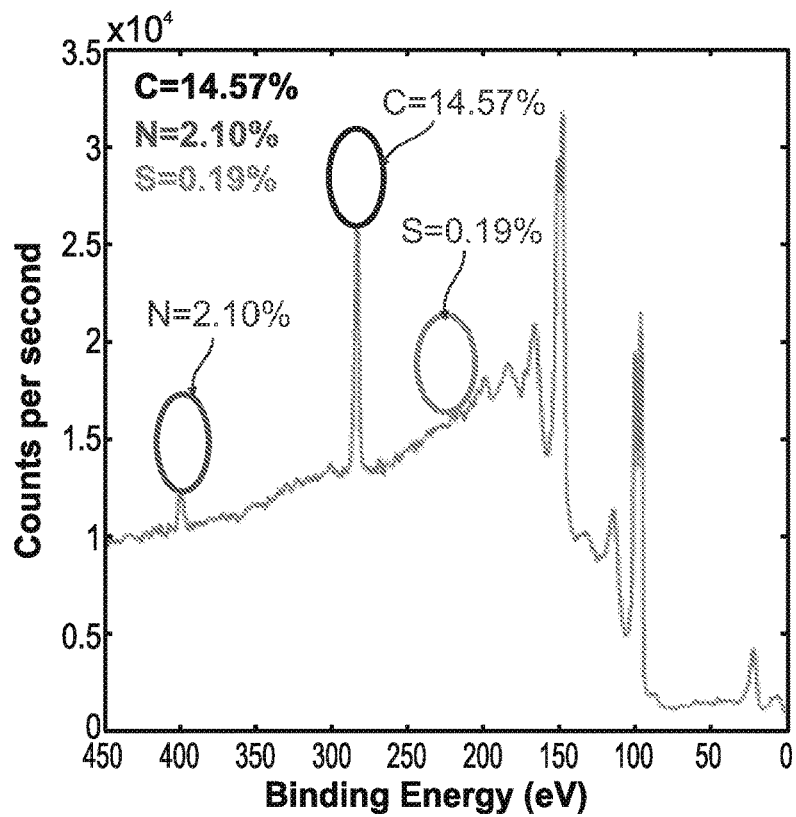
Figure 14F:
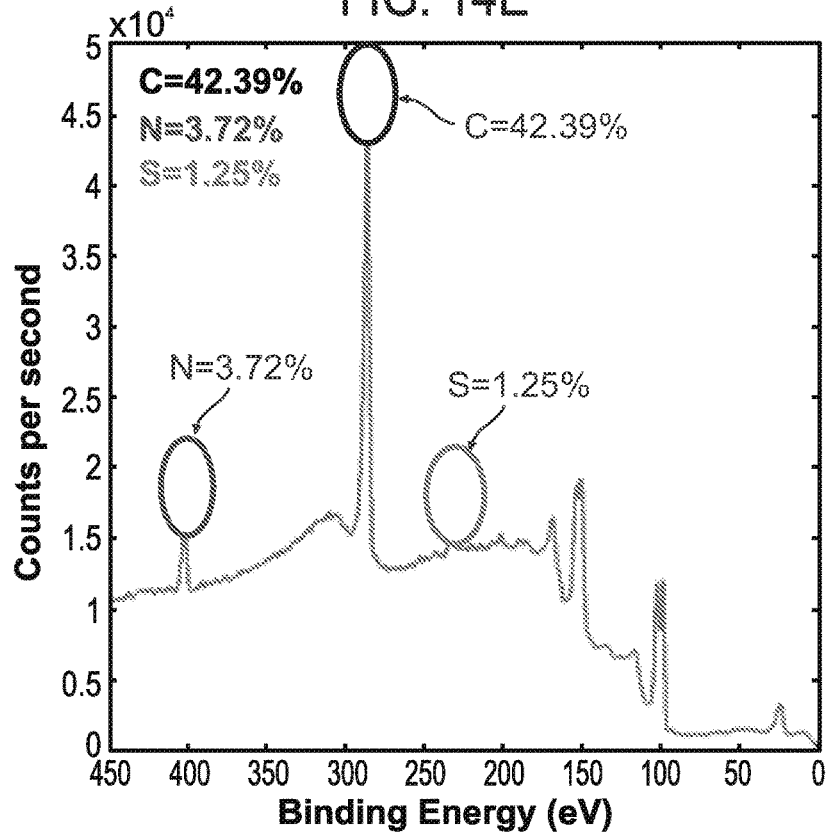

FIGS. 14A-F show surface modification (FIGS. 14A-C) and characterization of redox-reactive SiNW FET (FIGS. 14D-F). Shown in FIGS. 14A-C are Silanization of the SiNW activated surface with amine groups (FIGS. 14A to 14B), formation of the sulfonamide bond that connects 9,10-anthraquinone group to the modified surface (FIGS. 14B to 14C). Shown in FIGS. 14D-F are XPS spectra and atomic compositions of the modified surface for carbon (C), nitrogen (N) and sulfur (S). The XPS spectra of FIGS. 14D-F respectively correspond to modification stages 14A-C.

Figure 15:
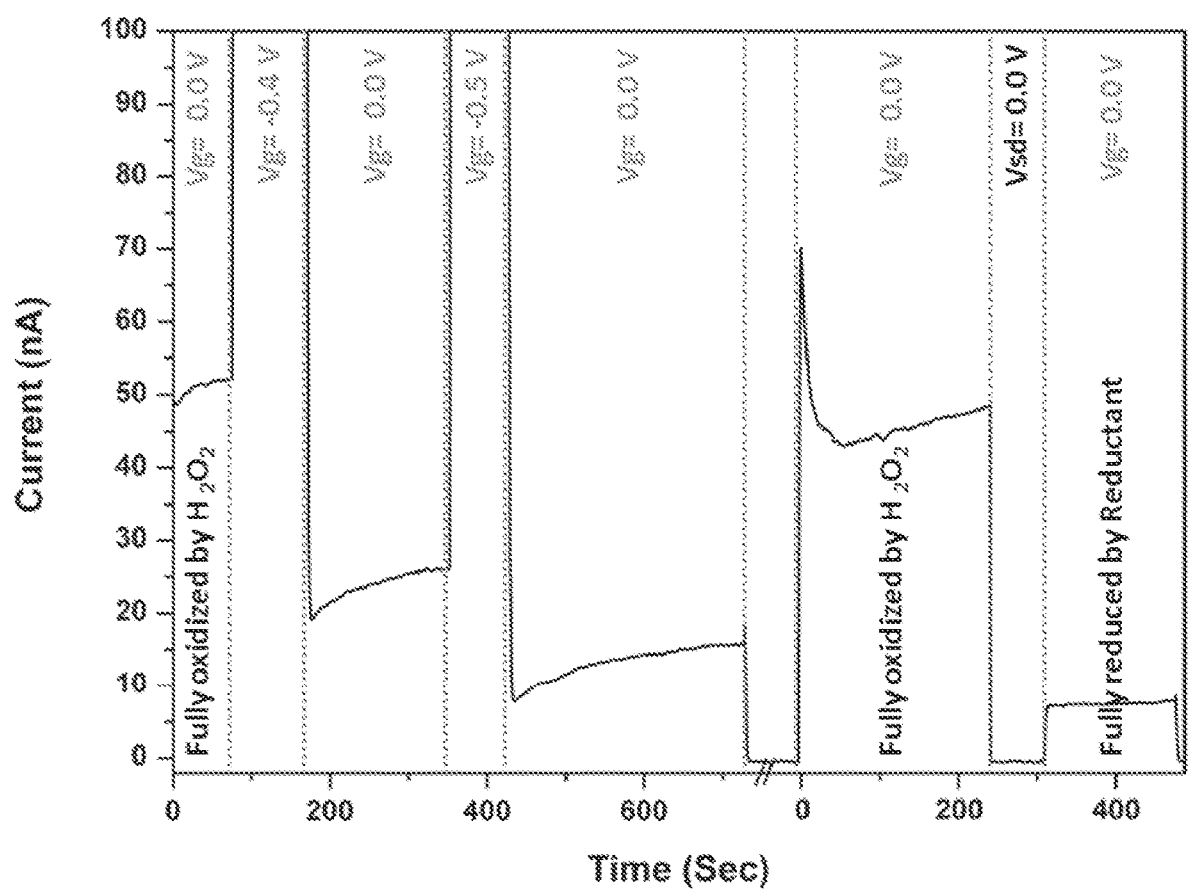
FIG. 15 shows a comparison between electrochemical reduction by gate and chemical reduction by reductant on redox active nanowire device, as obtained during experiments performed according to some embodiments of the present invention.

FIG. 15 shows a comparison between electrochemical reduction by gate and chemical reduction by reductant on redox active nanowire device. After turning on a negative gate for 2 minutes voltages there is a current drop. This phenomenon is also observed when the redox active nanowire device is reduced by a reductant. The experimental conditions were: source-drain voltage of 0.3V, measurements were done in phosphate saline buffer (155 mM pH=7.45), the nanowire device was fully oxidized by 1 mM $H_2O_2$ solution in phosphate saline buffer. The nanowire device was fully reduced by 1 vol % N, N-Diethylhydroxylamine (the reductant) in phosphate saline buffer. When there was no current on the nanowire the source-drain voltage was 0.0V.

Figure 16A:
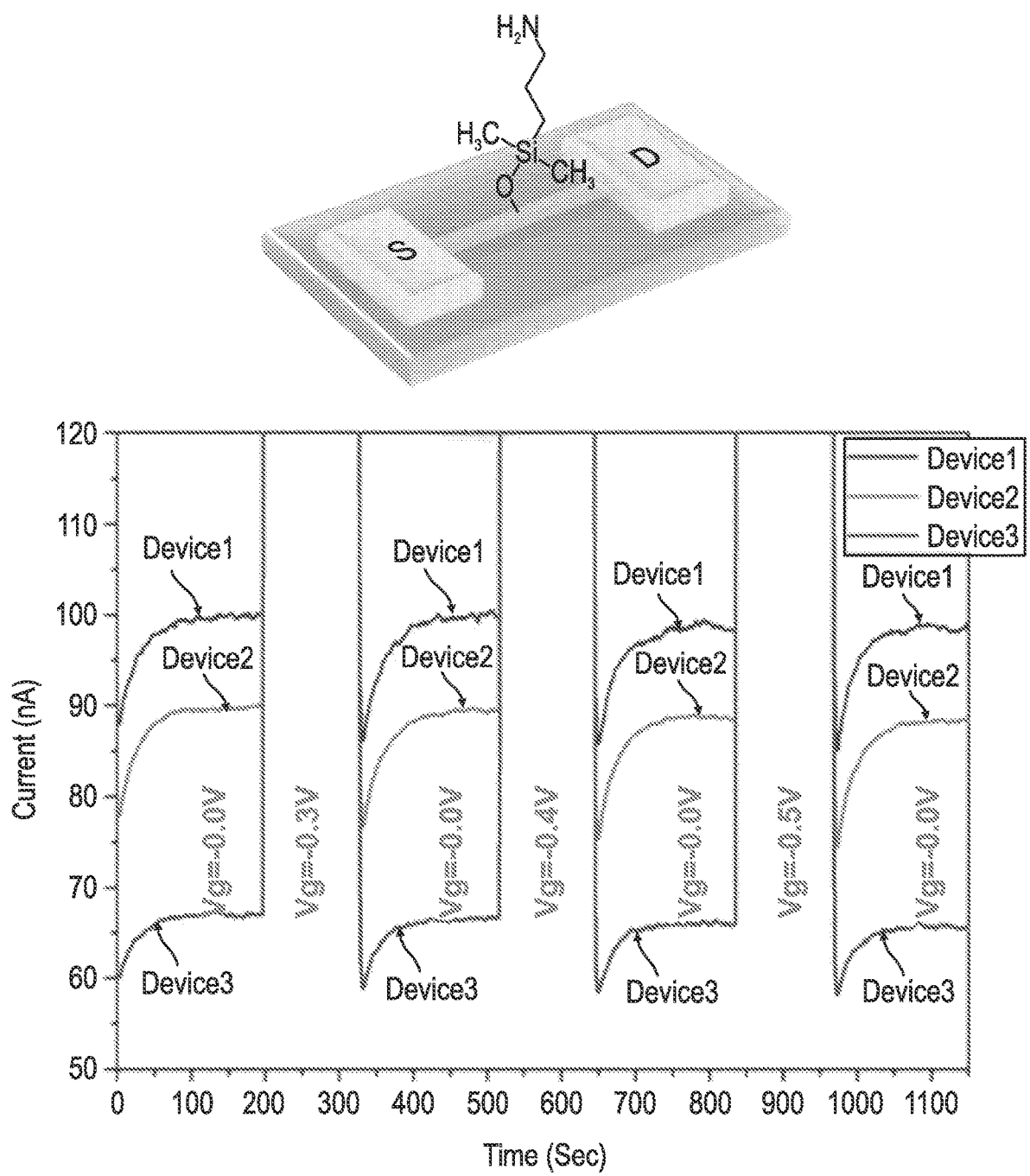
FIGS. 16A and 16B schematically show comparisons between non redox active and redox active moiety modified nanowire devices, as obtained during experiments performed according to some embodiments of the present invention.
Figure 16B:
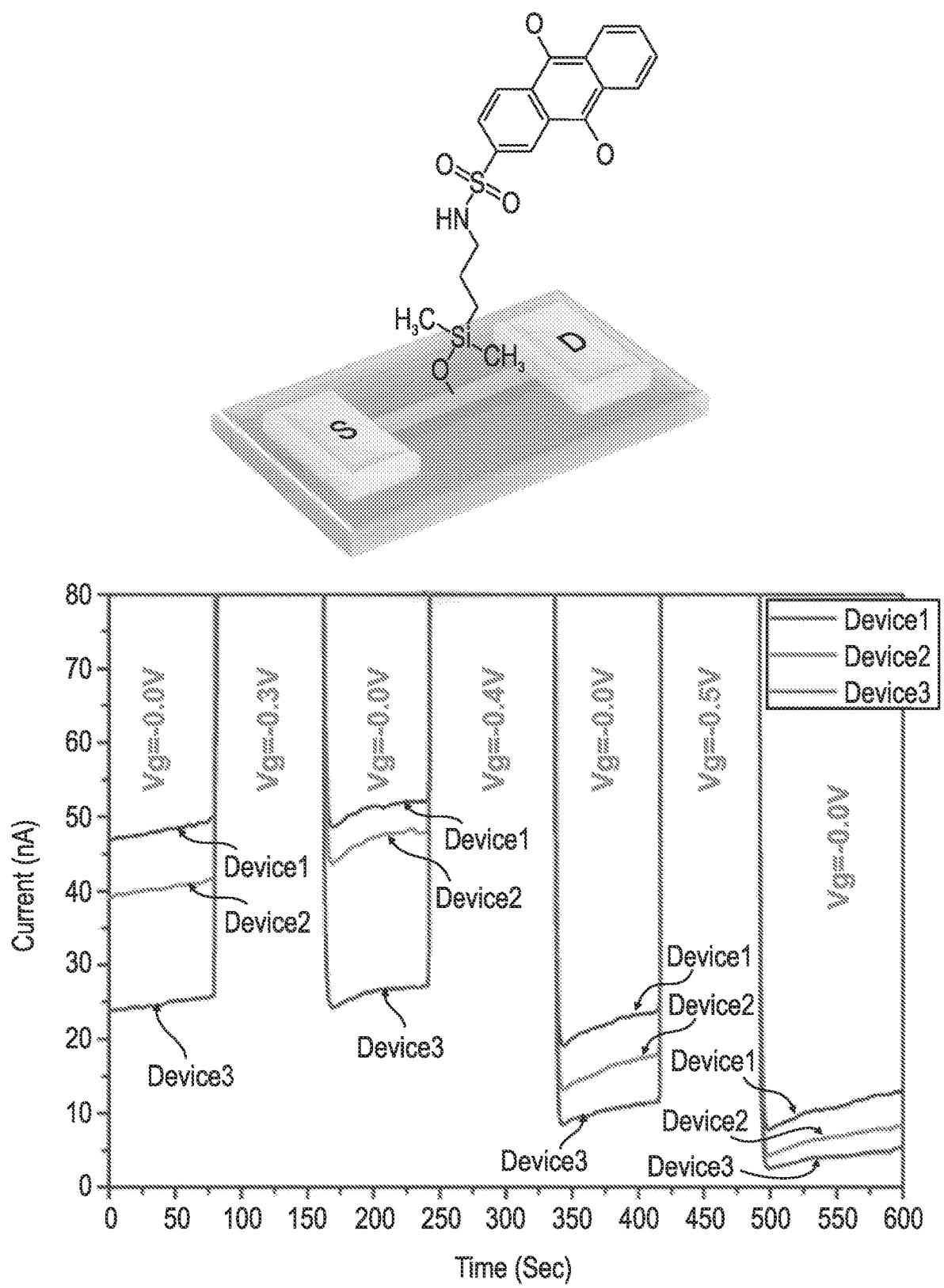

FIGS. 16A and 16B show a comparison between non redox active (FIG. 16B) and redox active (FIG. 16A) moiety modified nanowire devices. The non redox active devices were modified with (3-aminopropyl)-dimethyl-ethoxysilane only. In the case of redox active modification, after turning on a negative gate voltage for 3 minutes there was a current drop, indicating the reduction process. This phenomenon was not observed in the case of non redox active modified devices. The experimental conditions were: source-drain voltage of 0.3V, measurements were done in phosphate saline buffer (155 mM pH=7.45), before starting the measurements, the nanowire device was fully oxidized by 1 mM $H_2O_2$ solution in phosphate saline buffer.

Figure 17A:
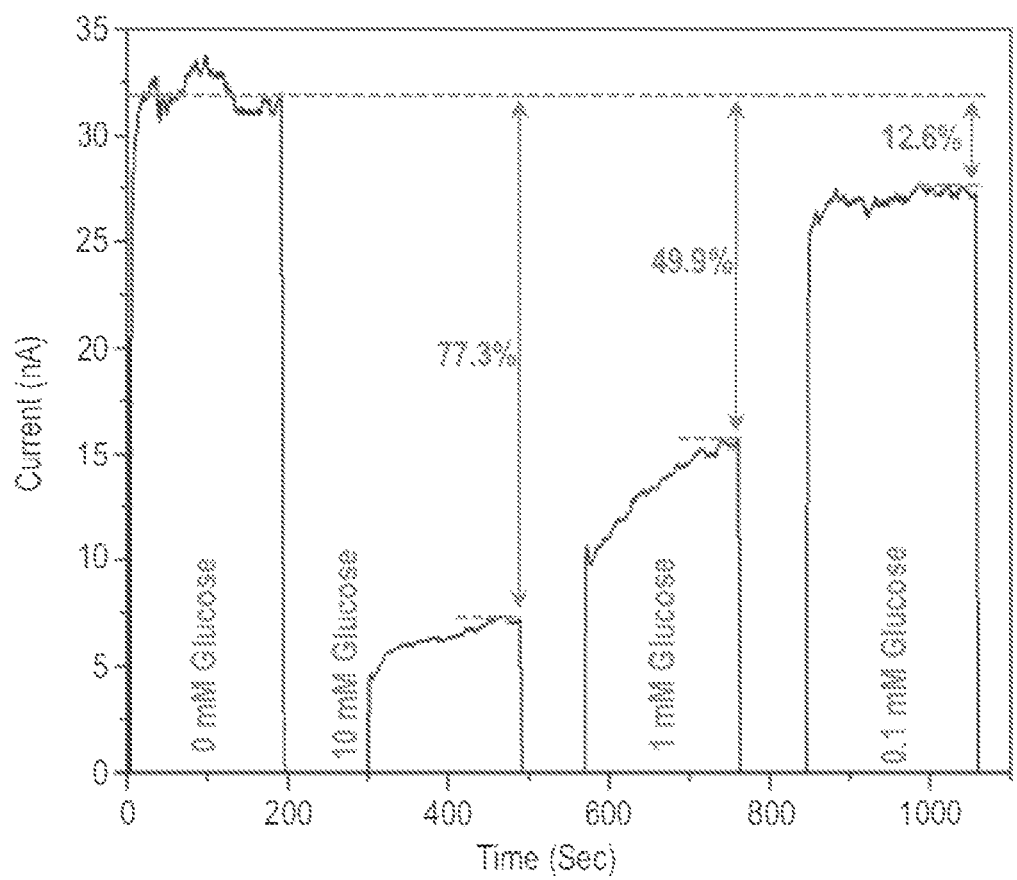
FIGS. 17A-B demonstrate sensing of glucose in Phosphate buffered saline using an exemplary redox active modified nanowire device operated during experiments performed according to some embodiments of the present invention.
Figure 17B:
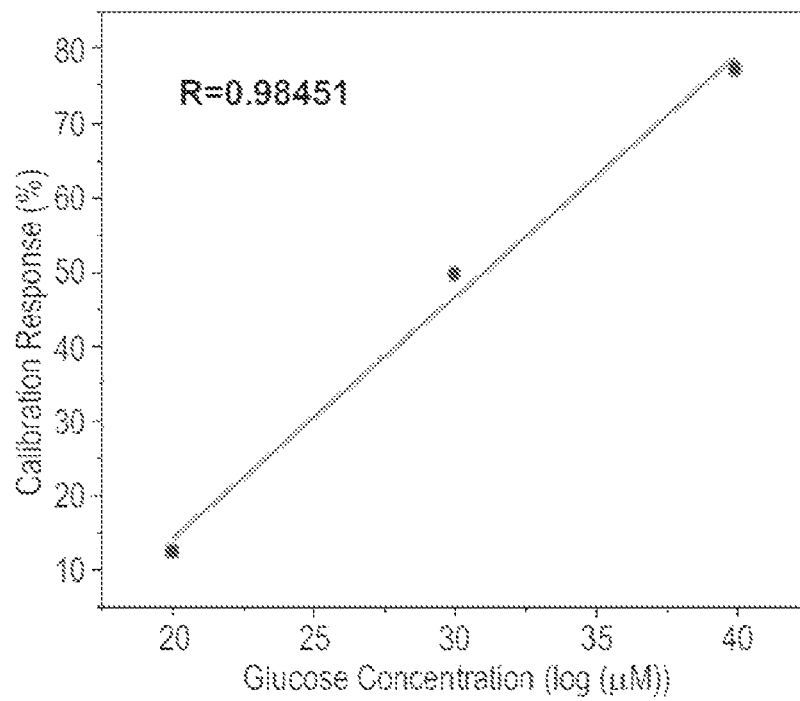

FIGS. 17A and 17B demonstrate sensing of glucose in Phosphate buffered saline using redox active modified nanowire device. Initially, glucose oxidase (50 µg/ml) was incubated 10 minutes with glucose containing sample. Then the samples were injected through tubing and PDMS channel. The signals acquired from the modified nanowire device were concentration-dependent. The experimental conditions were source-drain voltage of 0.3 V, and gate voltage of –0.9 V. Before injecting new sample (800 µl sample, rate=100 µl/second), the device was turn off (source-drain of 0 volt). The current values after 180 seconds from turning on the device were used for calibration.

Figure 18:
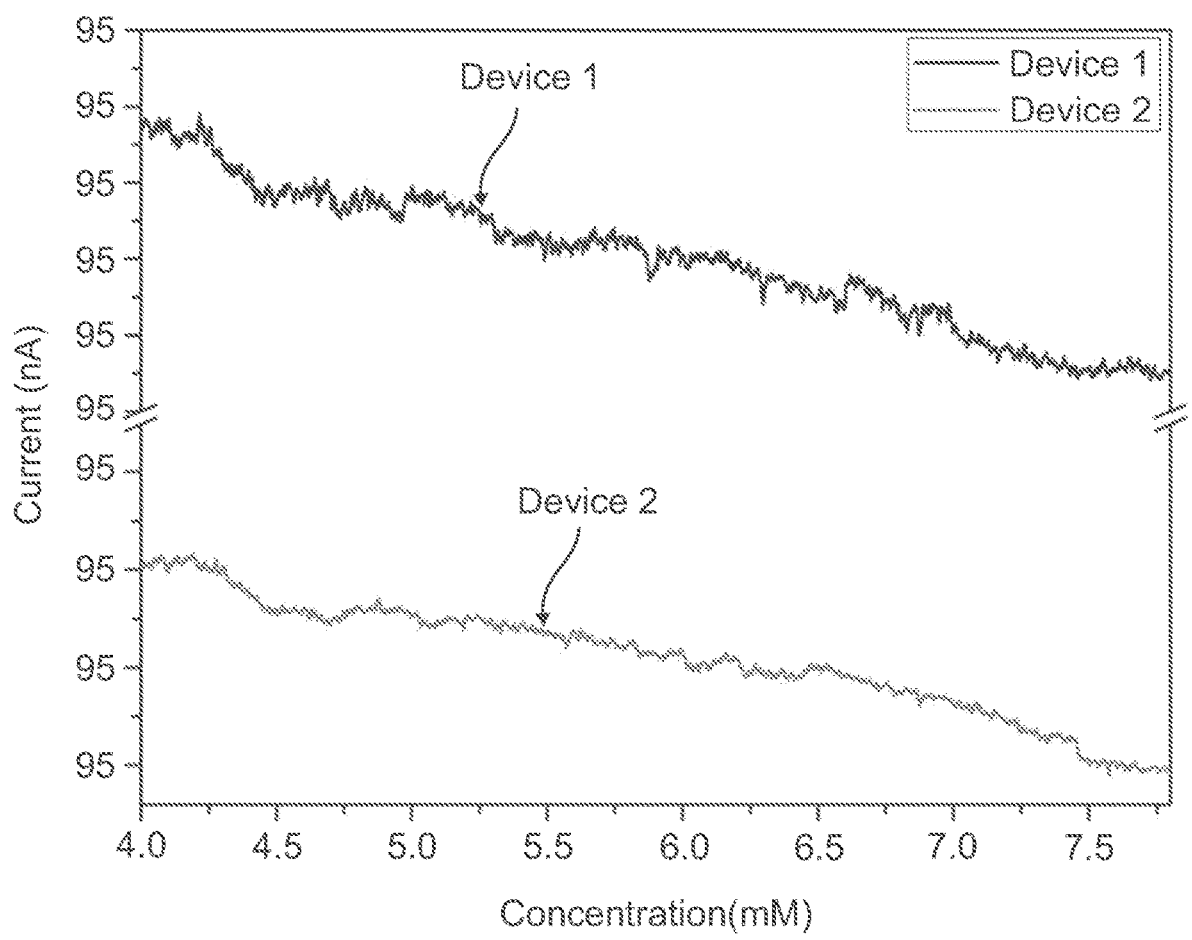
FIG. 18 shows results of continuous glucose monitoring in simulated interstitial fluid obtained in experiments performed according to some embodiments of the present invention.

FIG. 18 shows continuous glucose monitoring in simulated interstitial fluid using a redox active modified nanowire device. Initially, glucose oxidase (50 µg/ml) was incubated for 10 minutes with glucose containing sample. Then, the sample was introduced to the devices at 5 micro-liters per minute, using a fluid delivery system. Signals acquired from the modified nanowire devices were concentration-dependent and correlated. The experimental conditions were source-drain voltage of 0.3 V, and gate voltage of –0.4 V. The simulated interstitial fluid contained 25% bovine serum and 75% Phosphate buffered saline.

Example 6

A nano-device for non-invasive monitoring of excreted extra-cellular metabolites has been fabricated, according to some embodiments of the present invention. SiNW surfaces were oxidized using oxygen plasma in order to clean and activate the surface for the following silanization process. Afterwards, the chip containing the SiNW was covered with (3-aminopropyl)-dimethyl-ethoxysilane under a dry atmosphere (under Argon stream), to ensure the formation of a silane monolayer, which, due to Debye length considerations, is advantageous for sensing under physiological solution. Another consideration to use (3-aminopropyl)-dimethyl-ethoxysilane for the modification is the product's long-term stability under physiological conditions, compared to other silane-based modifications.

According to XPS measurements, modification with (3-aminopropyl)-dimethyl-ethoxysilane resulted in increased percentage of nitrogen atoms on the SiNW surface, which indicates successful binding of the amino-silane derivative. The amino-modified SiNW FET was then introduced to a solution of 9,10-anthraquinone-2-sulfochloride under dry argon atmosphere. Dry conditions were selected to prevent the decomposition of the sulfochloride group through hydrolysis. The sulfochloride group reacts with the amino groups on the SiNW FET surface to form a covalent highly stable sulfonamide bond, that enables the long-term fixation of 9,10-anthraquinone moieties to the SiNW FET surface. According to XPS measurements, following 9,10-anthraquinone-2-sulfochloride modification, there is an increase in the sulfur atoms percentage on the SiNW's surface, which indicates the successful binding of the 9,10-anthraquinone moiety.

Materials and Methods

Silicon Nanowires (SiNWs) p-Type Synthesis Via Chemical Vapor Deposition (CVD)

20 nm gold nanoparticles (Ted Pella) have catalyzed the growth of Si NWs via the vapor-liquid-solid (VLS) mechanism. These nanoparticles were first deposited on Silicon (100) growth substrates to define sites of Si NWs growth. In order to assist attachment of the gold nanoparticles to the silicon substrate, poly-L-lysine (Ted Pella) was first introduced to the silicon wafer, and served as an electrostatic binding agent. The organic materials were removed by applying 100 W and 0.200 Torr oxygen plasma for 5 min. Next, the wafer was placed in a quartz tube furnace, where silane (SiH4) and diborane (B2H6, 100 ppm in H2 balance gas) were used as reactants for the Si NWs growth process, in which boron served as a p-type dopant with a boron/silicon ratio of 1/4000. The rate of the Si NW growth was about 1 µm/min.

Silicon Nanowires Field-Effect Transistor Array Fabrication on Silicon Wafers

The SiNW-FET array was fabricated by photolithography, see FIGS. 12 and 13A-E. Following fabrication of the outer electrodes (including the gates) by photolithography and evaporation of chromium/gold (5/60 nm), respectively, the SiNWs were deposited on the wafer by dispersion in ethanol and dropping 0.5 µl drops on the oxide layer. The p-type SiNWs were deposited on a 3 inch silicon wafer, covered with 600 nm thermal oxide layer (<0.005 ohm/cm, SSP prime grade, Silicon Quest International). Source and drain electrodes of FETs were defined with a multilayer photoresist structure consisting of 500 nm LORSA (Microchem) and 500 nm S1805 (Shipley). The gap between the source and drain electrodes was 2 µm. Following exposure and development in MF319 developer, the chip was dipped in a buffered oxide etchant (hydrofluoric acid/ammonium fluoride ratio of 1/6) solution for 6 seconds, and immediately metallized by e-beam evaporation of titanium/palladium/titanium (5/60/10 nm). Subsequently, electrodes were insulated with a layer of 65 nm $Si_3N_4$, deposited by plasma-enhanced chemical vapor deposition at 80° C. (ICP-PECVD, Axic), and a layer of 10 nm alumina, made by atomic layer deposition (ALD, Savannah 200 system, Cambridge Nanotech). The chip was then subjected to lift-off in PG remover (or N-Methyl-2-pyrrolidone). The fabrication of the FET devices was ended by annealing in forming gas (hydrogen nitrogen ratio of 1/9), applied for 2 minutes at 380° C. by a rapid thermal processor (RTP).

Electrical Characterization of SiNWs Devices Using Water-Gate

Figure 19A:
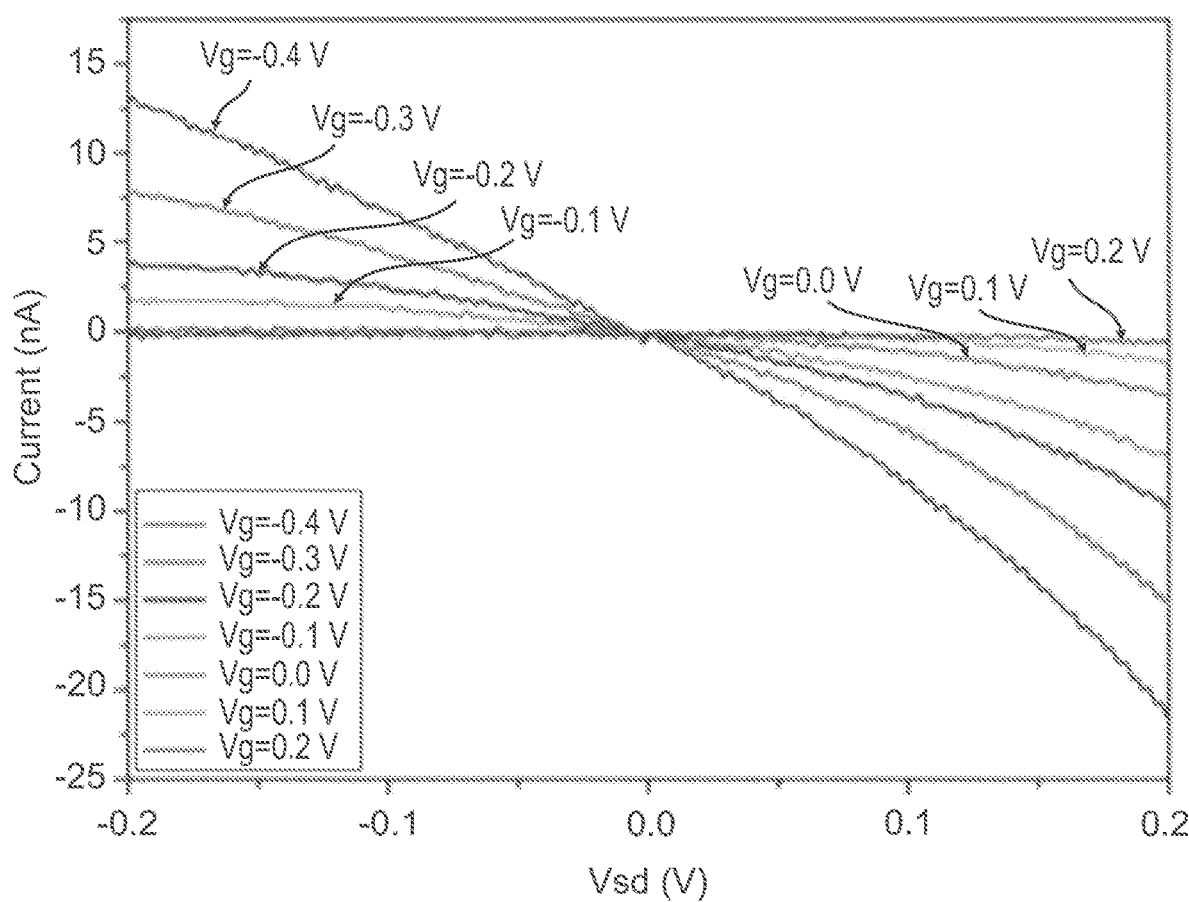
FIGS. 19A and 19B show electrical characterization of a p-type SiNW FET, obtained during experiments performed according to some embodiments of the present invention.
Figure 19B:
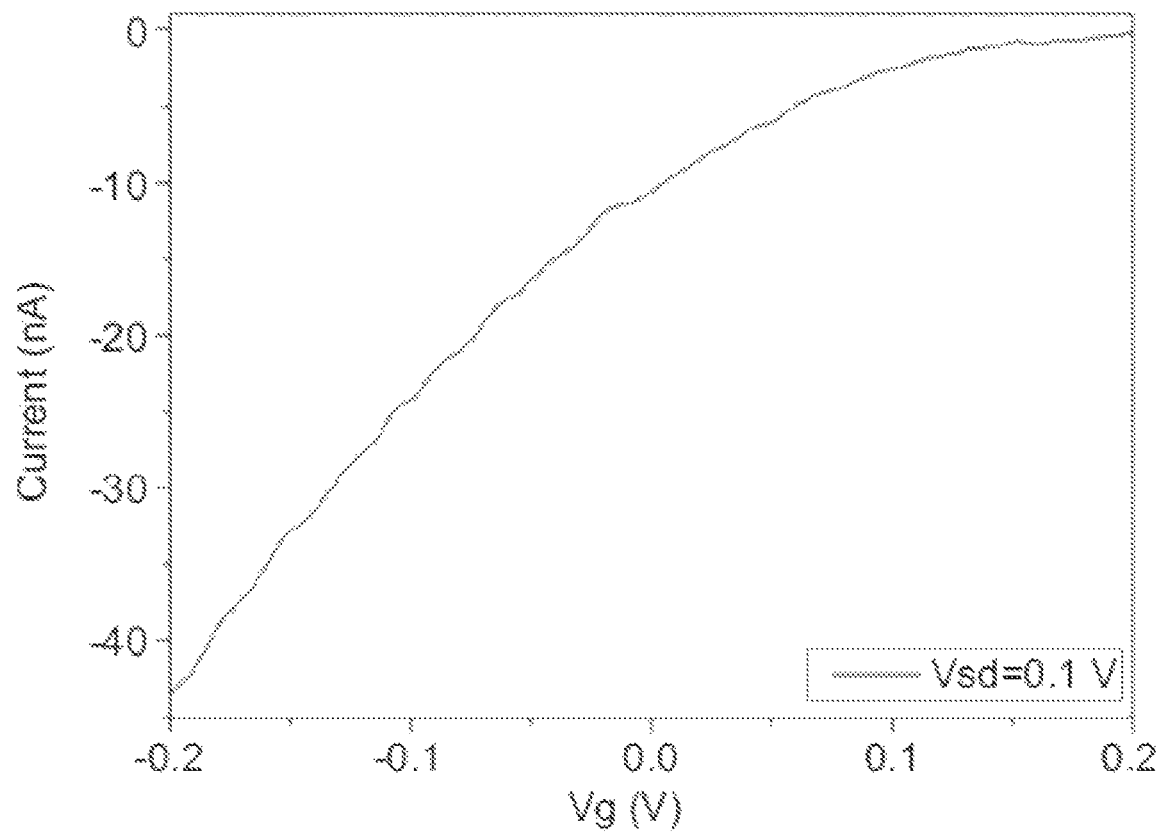

FIGS. 19A and 19B show electrical characterization of p-type SiNW FET nanodevices under water-gate configuration. FIG. 19A is a plot of source-drain current versus source-drain voltage (Vsd) at different gate voltages (Vg). FIG. 19B is a plot of source-drain current versus gate voltages (Vg) at 0.1 V source-drain voltage (Vg).

Prior to completion of the SiNW FET devices, the electrical properties of the SiNW devices on the sensor chip were characterized in deionized water by using a probe station. The characterization of the device's activity using source-voltage sweep, enabled selection of the source-drain voltage (Vsd) that allowed full scale sensitivity. Scanning the gate voltages (Vg) over fixed source voltage allowed characterizing parameters such as the carrier mobility, transconductance and threshold voltage. Based on these measurements, the best performing devices were selected and mapped for future sensing applications.

Scanning Electron Microscope Analysis

Figure 20A:
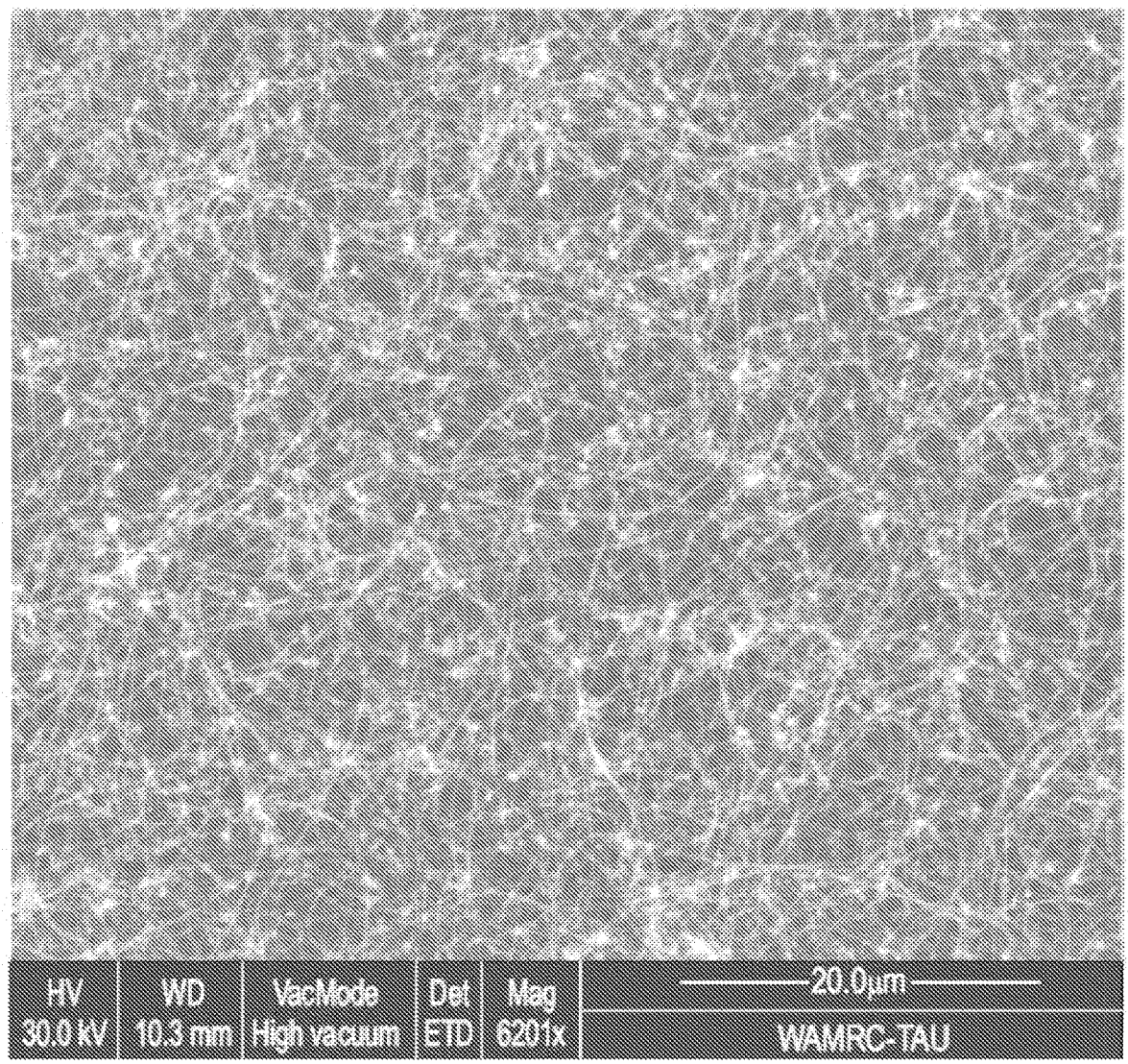
FIGS. 20A and 20B are Scanning Electron Microscope (SEM) images of the SiNWs, obtained during experiments performed according to some embodiments of the present invention.
Figure 20B:
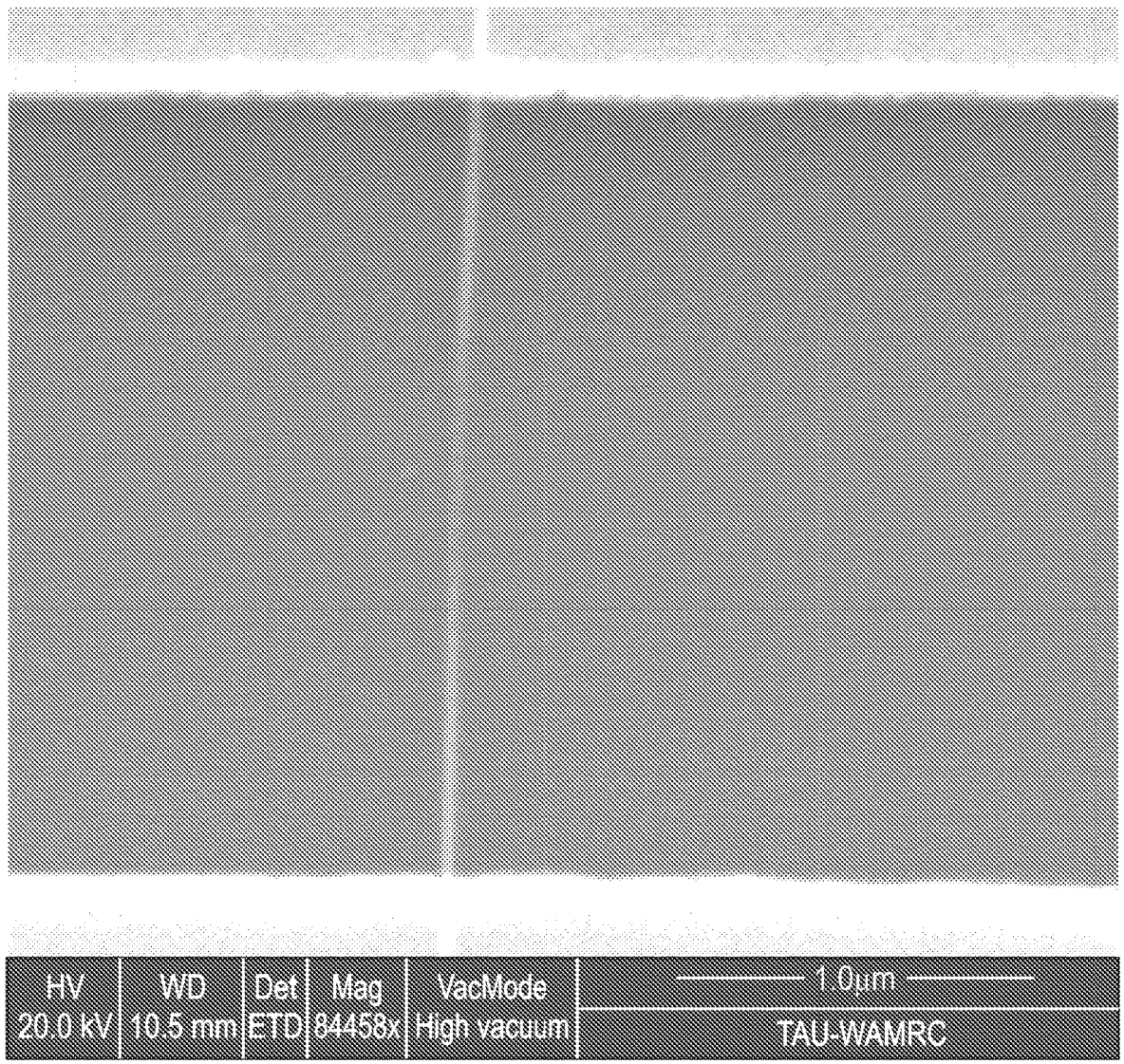

The quality of the synthesized p-type SiNWs and SiNW-devices was analyzed by using Quanta 200 FEG environmental scanning electron microscope (ESEM). FIGS. 20A and 20B are Scanning Electron Microscope (SEM) images of the SiNWs. FIG. 20A is SEM image of the synthesized 20 nm p-type SiNW via chemical vapor deposition system on silicon (100) wafer, and FIG. 20B is a SEM image of SiNW FET device consisting of SiNWs connected to source and drain electrodes. The images indicate good quality of the synthesized nanowires (FIG. 20A), and their successful assembly to FET devices (FIG. 20B).

Surface Modification

Following fabrication of the SiNW FET array, the chip was further chemically-modified with 9,10-anthraquinone-2-sulfochloride to perform sensing of cellular metabolites. The modifying agent was pre-synthesized as follows.

The sulfonate group of sodium 9,10-anthraquinone-2-sulfonate (743038, Sigma-Aldrich) was converted to sulfochloride, using oxalyl chloride (0880, Sigma-Aldrich) and N,N-dimethylformamide (227056, Sigma-Aldrich) in toluene (244511, Sigma-Aldrich). A mixture of sodium anthraquinone-2-sulfonate (5 grams, 0.0158 mol) and toluene (150 ml) was placed in 250 ml round-bottomed flask, equipped with an automatic water separator (Dean-Stark trap) and condenser, and the mixture was heated under reflux for 2 hours to dry the reaction mixture. The mixture was thereafter cooled to 60° C. and oxalyl chloride (6 ml) and N,N-dimethylformamide (2 drops, about 100 μl) were added. The resulting mixture was heated under reflux for 8 hours and a mixture of toluene and oxalyl chloride excess (30 ml) was thereafter distilled. A precipitate of sodium chloride was collected by filtration and the solvent was removed from the filtrate under reduced pressure. A solid residue was dried in vacuum overnight to give anthraquinone-2-sulfochloride (4.36 grams, 90% yield).

To conjugate the 9,10-anthraquinone-2-sulfochloride to the SiNWs surface, the FET chip was first washed with acetone (9005-68, J.T.Baker), isopropanol (9079-05, J.T.Baker), and deionized water (18 MΩ·cm) successively, followed by nitrogen drying. Then, oxygen plasma (100 W, 0.2 Torr) was applied for 15 min. The chip was covered by glass dish and inserted into a glove box (150B-G, Mbraun) under argon atmosphere (water and oxygen free) to perform the amino-silane modification. Immediately afterwards, the chip was covered with about 150 μl (3-aminopropyl)-dimethyl-ethoxysilane (APDMES; SIA0603.0, Gelest) for 60 min. Then, the chip was washed twice with about 30 ml of anhydrous toluene (244511, Sigma-Aldrich). The chip was transferred from the glove box to the clean room and washed again with isopropanol, followed by nitrogen drying. Next, the chip was placed on a hot plate at 115° C. for 25 min. The chip was then immersed in a mixture, containing 50 mg 9,10-anthraquinone-2-sulfochloride, 20 ml anhydrous toluene (244511, Sigma-Aldrich) and 1 ml anhydrous pyridine (270970, Sigma-Aldrich), in the glove box, under argon atmosphere (water and oxygen free) for 24 hours, for the formation of sulfonamide that connects the 9,10-anthraquinone group to the SiNW modified surface.

Mass Spectra Analysis

Mass spectroscopy (Autospec M250Q, Waters Corp. USA) analysis of 9,10-anthraquinone-2-sulfochloride (used for the SiNWs surface modification) was applied as a confirmation for the sulfochloride group formation.

X-Ray Photoelectron Spectroscopy Surface Chemistry Analysis

X-ray photoelectron spectroscopy (XPS) measurements were performed (Multi-Technique System 5600, PHI) in ultrahigh vacuum (2.5×10-10 Ton base pressure). The sample was irradiated by Al Kα monochromated source (1486.6 eV) and outcome electrons were analyzed by a spherical capacitor analyzer using a slit aperture of 0.8 mm. Since samples were slightly charged during measurements, this input was corrected mathematically, with $C_{1s}$ at 285 eV taken as an energy reference. All the measurements were performed at a shallow take-off angle of 25°. High resolution multiplex spectra was taken for different peaks in a low energy range window at a high resolution (Pass energy=11.75 eV, 0.05 eV/step). These measurements allow precise energy position, and peak shape determination, necessary for bonding analysis.

Fabrication of Fluid-Delivery System

PDMS was incubated with curing agent at 10:1 mass ratio for overnight at 60° C. The resulting device was then cut into rectangular pieces, at dimensions of 10×10×5 mm. Upstream polyethylene tube (PE 20, Intramedic) was 14 cm long and had 0.38 mm inner diameter. Downstream Tygon tube (S-50-HL, Tygon) was 13 cm long.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for detecting changes in an electrical property, comprising:

a sensing element comprising a transistor having a gate electrode and a semiconductor nanostructure connecting between a source electrode and a drain electrode and being modified by a functional moiety covalently attached thereto; and a voltage source connected to said gate electrode;

a controller configured for controlling a gate voltage applied by said voltage source to said gate electrode such as to reverse a redox reaction occurring when said moiety contacts a redox reactive agent; and a circuit for detecting changes in an electrical property of said nanostructure.

2. The system of claim 1, wherein said functional moiety is a redox reactive moiety.

3. The system of claim 1, wherein said functional moiety comprises at least one functional group capable of reversible change in an oxidation number or oxidation state of at least one of its atoms.

4. The system of claim 1, wherein said functional moiety comprises a quinone.

5. The system of claim 2, wherein said functional moiety comprises a quinone.

6. The system of claim 1, wherein said functional moiety comprises an aromatic quinone.

7. The system of claim 2, wherein said functional moiety comprises an aromatic quinone.

8. The system of claim 1, wherein said functional moiety or comprises a functional group elected from the group consisting of quinone, benzoquinone, anhraquinone, and phenanthrenequinone, each being substituted or unsubstituted.

9. The system of claim 2, wherein said functional moiety or comprises a functional group elected from the group consisting of quinone, benzoquinone, anhraquinone, and phenanthrenequinone, each being substituted or unsubstituted.

10. The system of claim 1, wherein said electrical property comprises electron or charge density on a surface of said nanostructure.

11. The system of claim 2, wherein said electrical property comprises electron or charge density on a surface of said nanostructure.

12. The system of claim 1, wherein said nanostructure is a nanowire.

13. The system of claim 1, wherein said semiconductor nanostructure comprises silicon.

14. The system of claim 1, wherein said sensing element comprises at least one additional transistor having a nanostructure modified by a non-redox active moiety, wherein said detector circuit is configured to subtract signals received from said nanostructure modified by said redox active moiety, from signals received from said nanostructure modified by said non-redox active moiety.

15. The system according to claim 1, being contained in a skin-attachable sticker.

16. The system according to claim 1, being contained in a housing implantable in a living body.

17. A method of sensing metabolic activity in a living organism, comprising:

contacting the living organism with a sensing element comprising a transistor having a gate electrode and a semiconductor nanostructure connecting between a source electrode and a drain electrode and being modified by a functional moiety covalently attached thereto;

detecting changes in an electrical property of said nanostructure resulting from redox reaction occurring during said contact; and applying gate voltage to said gate electrode so as to reverse said redox reaction.

18. The method according to claim 17, wherein said gate voltage is selected to maintain a generally constant population of said functional moiety on said nanostructure.

19. The system according to claim 1, wherein said gate voltage is constant.

20. The system according to claim 1, wherein said gate voltage is from about −3 volts to about +3 volts.

* * * * *